US012780824B2

(12) United States Patent
Ravi et al.

(10) Patent No.: US 12,780,824 B2
(45) Date of Patent: Nov. 3, 2026

(54) PURINE NUCLEOSIDES, THEIR INTERMEDIATES, AND METHODS OF PREPARATION THEREOF

(71) Applicants: Astrocyte Pharmaceuticals, Inc., Cambridge, MA (US); The U.S.A., as Represented by the Secretary, Department of Health and Human Services, Bethesda, MD (US)

(72) Inventors: Rama Suresh Ravi, Rockville, MD (US); Kenneth A. Jacobson, Silver Spring, MD (US); Russell Birch Poe, Groton Long Point, CT (US)

(73) Assignees: Astrocyte Pharmaceuticals, Inc., Cambridge, MA (US); The Unites States of America, as Represented by the Secretary, Department of Health and Human Services, Bethesda, MD (US)

( * ) Notice: Subject to any disclaimer, the term of this patent is extended or adjusted under 35 U.S.C. 154(b) by 335 days.

(21) Appl. No.: 18/288,318

(22) PCT Filed: Apr. 28, 2022

(86) PCT No.: PCT/US2022/071971
§ 371 (c)(1),
(2) Date: Oct. 25, 2023

(87) PCT Pub. No.: WO2022/232810
PCT Pub. Date: Nov. 3, 2022

(65) Prior Publication Data

US 2024/0368164 A1 Nov. 7, 2024

Related U.S. Application Data

(60) Provisional application No. 63/180,872, filed on Apr. 28, 2021.

(51) Int. Cl.

| | |
|---|---|
| ***C07D 473/24*** | (2006.01) |
| ***A61P 25/00*** | (2006.01) |
| ***C07D 473/18*** | (2006.01) |
| ***C07D 473/40*** | (2006.01) |

(52) U.S. Cl.
CPC ............ *C07D 473/24* (2013.01); *A61P 25/00* (2018.01); *C07D 473/18* (2013.01); *C07D 473/40* (2013.01)

(58) Field of Classification Search
CPC .. C07D 473/24; C07D 473/18; C07D 473/40; A61P 25/00
See application file for complete search history.

(56) References Cited

U.S. PATENT DOCUMENTS

| | | | |
|---|---|---|---|
| 5,773,423 | A | 6/1998 | Jacobson et al. |
| 5,776,423 | A | 7/1998 | Feeley et al. |
| 6,586,413 | B2 | 7/2003 | Liang et al. |
| 7,064,112 | B1 | 6/2006 | Fishman |
| 7,087,589 | B2 | 8/2006 | Jacobson et al. |
| 7,348,315 | B2 | 3/2008 | Liang et al. |
| 7,414,036 | B2 | 8/2008 | Sevillano et al. |
| 7,476,709 | B2 | 1/2009 | Moody et al. |
| 7,589,075 | B2 | 9/2009 | Fishman et al. |
| 7,790,735 | B2 | 9/2010 | Jacobson et al. |
| 7,825,126 | B2 | 11/2010 | Jacobson et al. |
| 7,867,983 | B2 | 1/2011 | Liang et al. |
| 8,399,018 | B2 | 3/2013 | Lichter et al. |
| 8,410,078 | B2 | 4/2013 | Liang et al. |
| 8,518,957 | B2 | 8/2013 | Jacobson et al. |
| 8,685,372 | B2 | 4/2014 | Tsien et al. |
| 8,691,775 | B2 | 4/2014 | Wurtman |
| 8,735,407 | B2 | 5/2014 | Jacobson et al. |
| 8,796,291 | B2 | 8/2014 | Jacobson et al. |
| 8,822,434 | B2 | 9/2014 | Liang et al. |
| 8,916,570 | B2 | 12/2014 | Jacobson et al. |
| 9,132,087 | B2 | 9/2015 | Lichter et al. |
| 9,132,131 | B2 | 9/2015 | Salvemini |
| 9,181,253 | B2 | 11/2015 | Jacobson et al. |
| 9,387,220 | B2 | 7/2016 | Fishman et al. |
| 9,526,739 | B2 | 12/2016 | Liang et al. |
| 9,561,209 | B2 | 2/2017 | Hughes et al. |
| 9,789,131 | B1 | 10/2017 | Korinek et al. |
| 9,963,450 | B2 | 5/2018 | Jacobson et al. |
| 10,265,338 | B2 | 4/2019 | Korinek et al. |
| 10,765,693 | B2 | 9/2020 | Poe et al. |
| 10,953,031 | B2 | 3/2021 | Korinek et al. |
| 11,324,769 | B2 | 5/2022 | Poe et al. |

(Continued)

FOREIGN PATENT DOCUMENTS

| | | | |
|---|---|---|---|
| CN | 1901915 | A | 1/2007 |
| CN | 1946732 | A | 4/2007 |

(Continued)

OTHER PUBLICATIONS

Tosh2, E J Med Chem, vol. 28, 2022, 113983, 1-18. (Year: 2022).*
Bozdemir, Neurotherapeutics, 2021, 1:2707-2721. (Year: 2021).*
Suresh, RSC Adv, 2021, vol. 11, 27369, 1-12. (Year: 2021).*
Liston, Purinergic Signalling, 2020, 16:53-559. (Year: 2020).*
Tosh, Bio& Med Chem Lett 0, 2020, 127599, 1-8. (Year: 2020).*
Melman, Bio & Med Chem Lett 1, 2008, 2813-2819. (Year: 2008).*
Tichilibon, J Med Chem, 2005, 48, 1745-1758. (Year: 2005).*
International Search Report for PCT Application No. PCT/US2023/036747, mailed by the U.S. Patent and Trademark Office on Feb. 20, 2024.

(Continued)

*Primary Examiner* — D Margaret M Seaman
(74) *Attorney, Agent, or Firm* — COOLEY LLP

(57) ABSTRACT

The present invention provides purine nucleoside analog compounds and methods of use thereof for treatment of certain injuries, disorders and conditions, for example brain injuries such as stroke or traumatic brain injuries. The present invention further provides methods of synthesizing such compounds, and intermediates useful in the synthesis of such compounds.

19 Claims, No Drawings

(56) References Cited

U.S. PATENT DOCUMENTS

| | | | | |
|---|---|---|---|---|
| 11,484,545 | B2 | 11/2022 | Korinek et al. | |
| 11,839,615 | B2 | 12/2023 | Korinek et al. | |
| 12,239,654 | B2 | 3/2025 | Korinek et al. | |
| 2003/0216412 | A1 | 11/2003 | Jacobson et al. | |
| 2009/0088403 | A1 | 4/2009 | Blakely et al. | |
| 2009/0258850 | A1 | 10/2009 | Frincke et al. | |
| 2009/0306225 | A1 | 12/2009 | Lichter et al. | |
| 2010/0047798 | A1 | 2/2010 | Feldman et al. | |
| 2010/0197914 | A1 | 8/2010 | Fairhurst | |
| 2010/0256086 | A1 | 10/2010 | Fischer | |
| 2011/0046166 | A1 | 2/2011 | Jacobson et al. | |
| 2014/0241990 | A1 | 8/2014 | Haydon et al. | |
| 2015/0087613 | A1 | 3/2015 | Salvemini | |
| 2016/0024135 | A1 | 1/2016 | Chai et al. | |
| 2017/0002007 | A1 | 1/2017 | Jacobson et al. | |
| 2018/0021363 | A1* | 1/2018 | Korinek | A61K 31/52 514/46 |
| 2019/0225615 | A1 | 7/2019 | Casale et al. | |
| 2020/0009384 | A1 | 1/2020 | Canning et al. | |
| 2020/0046751 | A1 | 2/2020 | Korinek et al. | |
| 2020/0093848 | A1 | 3/2020 | Poe et al. | |
| 2021/0030760 | A1 | 2/2021 | Korinek et al. | |
| 2021/0077518 | A1 | 3/2021 | Poe et al. | |
| 2022/0305044 | A1 | 9/2022 | Korinek et al. | |
| 2023/0165887 | A1 | 6/2023 | Korinek et al. | |

FOREIGN PATENT DOCUMENTS

| | | | |
|---|---|---|---|
| CN | 101056879 | A | 10/2007 |
| CN | 104873531 | A | 9/2015 |
| CN | 105934433 | A | 9/2016 |
| CN | 109666053 | A | 4/2019 |
| EP | 1624753 | A2 | 2/2006 |
| EP | 3856741 | A4 | 6/2022 |
| JP | 2003-519698 | A | 6/2003 |
| JP | 2005534629 | A | 11/2005 |
| JP | 2008512457 | A | 4/2008 |
| JP | 2019515920 | A | 6/2019 |
| JP | 2019522018 | A | 8/2019 |
| JP | 2022502405 | A | 1/2022 |
| WO | WO-2003051881 | A1 | 6/2003 |
| WO | WO-2004047749 | A2 | 6/2004 |
| WO | WO-2005063246 | A1 | 7/2005 |
| WO | WO-2006031505 | A1 | 3/2006 |
| WO | WO-2006091905 | A1 | 8/2006 |
| WO | WO-2007020018 | A1 | 2/2007 |
| WO | WO-2008021552 | A2 | 2/2008 |
| WO | WO-2009010871 | A2 | 1/2009 |
| WO | WO-2009018871 | A1 | 2/2009 |
| WO | WO-2010014921 | A2 | 2/2010 |
| WO | WO-2011077435 | A1 | 6/2011 |
| WO | WO-2014160502 | A1 | 10/2014 |
| WO | 2015080940 | A1 | 6/2015 |
| WO | WO-2016123672 | A1 | 8/2016 |
| WO | WO-2017185061 | A1 | 10/2017 |
| WO | 2018164513 | A1 | 9/2018 |
| WO | WO-2019157317 | A1 | 8/2019 |
| WO | WO-2020069068 | A1 | 4/2020 |
| WO | WO-2021021717 | A1 | 2/2021 |
| WO | 2022074127 | | 4/2022 |
| WO | WO-2022232810 | A1 | 11/2022 |
| WO | 2023091791 | A1 | 5/2023 |
| WO | 2024097387 | A1 | 5/2024 |
| WO | 2024144874 | A2 | 7/2024 |

OTHER PUBLICATIONS

Jacobson et al., "Methanocarba Analogues of Purine Nucleosides as Potent and Selective Adenosine Receptor Agonists," J. Med. Chem., 2000; 43:2196-2203.

Pubchem, SID 374445831, Modify Date: Jun. 23, 2018; Retrieved from the Internet: https://pubchem.ncbi.nlm.nih.gov/substance/374445831.

Tosh et al., "Structure activity relationship of novel antiviral nucleosides against Enterovirus A71," Bioorganic & Medicinal Chemistry Letters, 2020, vol. 30, 8 pages.

Tosh et al., "Structure-Based Scaffold Repurposing for G Protein-Coupled Receptors: Transformation of Adenosine Derivatives into 5HT2B/5HT2c Serotonin Receptor Antagonists," Journal of Medicinal Chemistry, 2016; 59:11006-11026.

Ando et al., "A comparative analysis of the activity of ligands acting at P2X and P2Y receptor subtypes in models of neuropathic, acute and inflammatory pain," British Journal of Pharmacology, Mar. 2010, vol. 159, No. 5, pp. 1106-1117.

Armstrong et al., "Adenosine receptor specificity in preconditioning of isolated rabbit cardiomyocytes: evidence of A3 receptor involvement," Cardiovascular Research, Jul. 1994, vol. 28, No. 7, pp. 1049-1056.

Auchampach et al., "Selective Activation of A3 Adenosine Receptors with N6-(3-lodobenzyl)Adenosine-5'-N-Methyluronamide Protects Against Myocardial Stunning and Infarction without Hemodynamic Changes in Conscious Rabbits," Circulation Research, vol. 80, Jun. 1997 (pp. 800-809).

Augustijns et al., ed., Solvent Systems and Their Selection in Pharmaceutics and Biopharmaceutics, 2007, American Association of Pharmaceutical Scientists, Springer, 2007, pp. 53-109.

Baltos et al., "Structure-Activity Analysis of Biased Agonism at the Human Adenosine A3 Receptor," Molecular Pharmacology, vol. 90, No. 1, Jul. 2016 (pp. 12-22).

Barragán-Iglesias et al., "Participation of Peripheral P2Y1, P2Y6 and P2Y11 receptors in formalin-induced inflammatory pain in rats," Pharmacology, Biochemistry and Behavior, vol. 128, Jan. 2015 (pp. 23-32).

Ben et al., "Different efficacy of adenosine and NECA derivatives at the human A3 adenosine receptor: insight into the receptor activation switch," Biochemical Pharmacology, vol. 87, No. 2, Jan. 2014 (pp. 321-331).

Beukers et al., "New, non-adenosine, high-potency agonists for the human adenosine A2B receptor with an improved selectivity profile compared to the reference agonist N-ethylcarboxamidoadenosine," Journal of Medicinal Chemistry, vol. 47, No. 15, Jul. 2004 (pp. 3707-3709).

Björklund et al., "Adenosine A1 and A3 receptors protect astrocytes from hypoxic damage," European Journal of Pharmacology, vol. 596, No Month Listed 2008 (pp. 6-13).

Borea et al., "The A3 Adenosine Receptor: History and Perspectives," Pharmacological Reviews, vo. 67, Jan. 2015 (pp. 74-102).

Bourdon et al., "(N)-methanocarba-2MeSADP (MRS2365) is a subtype-specific agonist that induces rapid desensitization of the P2Y1, receptor of human platelets," Journal of Thrombosis and Haemostasis, vol. 4, No. 4, Apr. 2006 (pp. 861-868).

Brittain, "Polymorphism in Pharmaceutical Solids," Marcel Dekker Inc., 1999; 183-226.

Byrn et al., "Pharmaceutical Solids: A Strategic Approach to Regulatory Considerations," Pharmaceutical Research, 1995, vol. 12, No. 7, pp. 945-954.

Camaioni et al., "Adenosine receptor agonists: synthesis and biological evaluation of the disatereoisomers of 2-(3-hydroxy-3-phenyl-1-propyn-1-yl)NECA," Bioorganic & Medicinal Chemistry, vol. 5, No. 12, Dec. 1997 (pp. 2267-2275).

CDC, Types of Stroke, https://web.archive.org/web/20150315064531/http://www.cdc.gov/stroke/types_of_stroke.htm; 2013.

Chen et al., "Activation of Adenosine A3 Receptors Reduces Ischemic Brain Injury in Rodents," Journal of Neuroscience Research, vol. 84, No Month Listed 2006 (pp. 1848-1855).

Choi et al., "A3 Adenosine Receptor Agonist Reduces Brain Ischemic Injury and Inhibits Inflammatory Cell Migration in Rats," The America Journal of Pathology, vol. 179, No. 4, Oct. 2011 (pp. 2042-2052).

Ciancetta et al., "Structural Probing and Molecular Modeling of the A3 Adenosine Receptor: A Focus on Agonist Binding," Molecules, vol. 22, No. 3, Mar. 2017 (17 pages).

Cosyn et al., "2-Triazole-Substituted Adenosines: A New Class of Selective A3 Adenosine Receptor Agonists, Partial Agonists, and Antagonists," The Journal of Medicinal Chemistry, vol. 49, No. 25, Dec. 2006 (pp. 7373-7383).

(56) References Cited

OTHER PUBLICATIONS

Cosyn et al., "Synthesis of hypermodified adenosine derivatives as selective adenosine A3 receptor ligands," Bioorganic & Medicinal Chemistry, vol. 14, 2006 (pp. 1403-1412) (Nov. 2005).
Cristalli et al., "2-Aralkynyl and 2-Heteroalkynyl derivatives of adenosine-5'-N-ethyluronamide as selective A2a adenosine receptor agonists," Journal of Medicinal Chemistry, vol. 38, No. 9, Apr. 1995 (pp. 1462-1472).
D'Alimonte et al., "Potentiation of temozolomide antitumor effect by purine receptor ligands able to restrain the in vitro growth of human glioblastoma stem cells," Purinergic Signalling, vol. 11, No. 3, Sep. 2015 (pp. 331-346).
Devine et al., "Synthesis and evaluation of new N6-substituted adenosine-5'-N-methylcarboxamides as A3 adenosine receptor agonists," Bioorganic & Medicinal Chemistry, vol. 18, No. 8, May 2010 (pp. 3078-3087).
Doyle et al., "Adenosine A3 Receptor Expression and Function in Mitochondria," The FASEB Journal, vol. 30, No. 1, Apr. 2016, Supplement 1266.6 (2 pages).
Fedorova et al., "Behavioral Characterization of Mice Lacking the A3 Adenosine Receptor: Sensitivity to Hypoxic Neurodegeneration," Cell Molecular Neurobiology, vol. 23, No. 3, Jun. 2003 (pp. 431-447).
Gao et al., "Allosteric modulation and functional selectivity of G protein-coupled receptors," Drug Discovery Today. Technologies, vol. 10, No. 2, No Month Listed 2013 (pp. e237-e243).
Gao et al., "Functionally biased modulation of A3 adenosine receptor agonist efficacy and potency by imidazoquinolinamine allosteric enhancers," Biochemical Pharmacology, vol. 82, No. 6, Sep. 2011 (pp. 658-668).
Gao et al., "Partial Agonists for A3 Adenosine Receptors," Current Topics in Medicinal Chemistry, vol. 4, No. 8, Apr. 2004 (pp. 855-862).
Gao et al., "Structural Determinants of A3 Adenosine Receptor Activation: Nucleoside Ligands at the Agonist/Antagonist boundary," Journal of Medicinal Chemistry, vol. 45, No. 20, Aug. 2002 (pp. 4471-4484).
Gillerman et al., "Investigations into the Origin of the Molecular Recognition of Several Adenosine Deaminase Inhibitors," J. Med. Chem., vol. 54, No. 6, 2011 (pp. 107-121).
Goadsby et al., "Adenosine A1 receptor agonists inhibit trigeminovascular nociceptive transmission," Guarantors of Brain, 2002 (pp. 1392-1401).
Gundry et al., "A Practical Guide to Approaching Biased Agonism at G Protein Coupled Receptors," Frontiers in Neuroscience, vol. 11, No. 17, Jan. 2017 (6 pages).
Hirayama, "Handbook for Preparation of Organic Compound Crystals," Maruzen Inc., Jul. 25, 2008, pp. 57-84.
International Search Report for PCT Application No. PCT/US2017/028996, mailed by the U.S. Patent and Trademark Office on Aug. 2, 2017 (10 pages).
International Search Report for PCT Application No. PCT/US2019/017265, mailed by the U.S. Patent and Trademark Office on May 7, 2019 (9 pages).
International Search Report for PCT Application No. PCT/US2019/053076, mailed by the U.S. Patent and Trademark Office on Dec. 13, 2019 (8 pages).
International Search Report for PCT Application No. PCT/US2022/071971, mailed by the U.S. Patent and Trademark Office on Aug. 24, 2022 (14 Pages).
Jacobson et al., "Historical and Current Adenosine Receptor Agonists in Preclinical and Clinical Development," Front Cell Neurosci., 2019, vol. 13, No. 124, 17 pages.
Jacobson et al., "John Daly Lecture: Structure-guided Drug Design for Adenosine and P2Y Receptors," Computational and Structural Biotechnology Journal, vol. 13, Oct. 2014 (pp. 286-298).
Jacobson et al., "Medicinal Chemistry of the A3 Adenosine Receptor: Agonists, Antagonists, and Receptor Engineering," Handbook Experimental Pharmacology, vol. 193, No Month Listed 2009 (pp. 123-159).
Jacobson et al., "P2Y nucleotide receptors: Promise of therapeutic applications," Drug Discovery Today, vol. 15, Nos. 13-14, Jul. 2010 (pp. 570-578).
Kim et al., "Three-dimensional quantitative structure-activity relationship of nucleosides acting at the A3 adenosine receptor: analysis of binding and relative efficacy," Journal of Chemical Information and Modeling, vol. 47, No. 3, May 2007 (pp. 1225-1233).
Klotz et al., "2-substituted N-ethylcarboxamidoadenosine derivatives as high-affinity agonists as human A3 adenosine receptors," Naunyn-Schmiedeberg's Archives of Pharmacology, vol. 360, No. 2, Aug. 1999 (pp. 103-108).
Koch et al., "Impaired Cognition after Stimulation of P2Y1 Receptors in the Rat Medial Prefrontal Cortex," Neuropsychopharmacology, vol. 40, No. 2, Jan. 2015 (pp. 305-314).
Kumar et al., "5'-Phosphate and 5'-Phosphonate Ester Derivatives of (N)-Methanocarba Adenosine with in Vivo Cardioprotective Activity," Journal of Medicinal Chemistry, vol. 56, No. 3, Jan. 2013 (pp. 902-914).
Kwon et al., "Blockade of Peripheral P2Y1 Receptors Prevents the Induction of Thermal Hyperalgesia via Modulation of TRPV1 Expression in Carrageenan-Induced Inflammatory Pain Rats: Involvement of p38 MAPK Phosphorylation in DRGs," Neuropharmacology, vol. 79, Dec. 2013 (pp. 368-379).
Lee et al., "Ring-Constrained (N)-Methanocarba Nucleosides as Adenosine Receptor Agonists: Independent 5'-Uronamide and 2'-Deoxy Modifications," Bioorganic & Medicinal Chemistry Letters, vol. 11, No Month Listed 2001 (pp. 1333-1337).
Lewerenz et al., "A3 Receptors in Cortical Neurons: Pharmacological Aspects and Neuroprotection during Hypoxia," Drug Development Research, vol. 58, 2003 (pp. 420-427).
Liang et al., "A physiological role of the adenosine A3 receptor: Sustained cardioprotection," The Proceedings of the National Academy of Science, U.S.A., vol. 95, No. 12, Jun. 1998 (pp. 6995-6999).
Little et al., "Endogenous adenosine A3 receptor activation selectively alleviates persisent pain states," Brain Advance Access published Nov. 19, 2015; (pp. 1-8).
Lubitz et al., "Adenosine A3 receptor stimulation and cerebral ischemia," European Journal of Pharmacology, vol. 263, No Month Listed 1994 (pp. 59-67).
Lubitz et al., "Chronic administration of adenosine A3 receptor agonist and cerebral ischemia: neuronal and glial effects," European Journal of Pharmacology, vol. 367, No Month Listed 1999 (pp. 157-163).
Lubitz et al., "Right Thing at a Wrong Time? Adenosine A3 Receptors and Cerebroprotection in Stroke," Annals New York Academy of Sciences, Neuroprotective Agents: Fifth International Conference, vol. 939, Jun. 2001 (pp. 85-96).
Mayo Clinic Staff, "Compulsive Gambling-Diagnosis", Mayo Foundation for Medical Education and Research (MFMER), (Oct. 22, 2016), p. 1, URL: https://www.mayoclinic.org/diseases-conditions/compulsive-gambling/diagnosis-treatment/drc-20355184.
Mayo Clinic Staff, "Compulsive Gambling-Symptoms", Mayo Foundation for Medical Education and Research (MFMER), (Oct. 22, 2016), p. 1, URL: https://www.mayoclinic.org/diseases-conditions/compulsive-gambling/symptoms-causes/syc-20355178.
Mañé et al., "BPTU, an allosteric antagonist of P2Y1 receptor, blocks nerve mediated inhibitory neuromuscular responses in the gastrointestinal tract of rodents," Neuropharmacology. 2016; 110(Pt A): 376-385.
Mañé et al., "Differential functional role of purinergic and nitrergic inhibitory co-transmitters in human colonic relaxation," Acta Physiologica, vol. 212, No. 4, Oct. 2014 (pp. 293-305).
Müller et al., "Recent developments in adenosine receptor ligands and their potential as novel drugs," Biochimica et Biophysica Acta, vol. 1808, vol. 5, May 2011 (pp. 1290-1308).
Nayak et al., "Synthesis and Anti-Renal Fibrosis Activity of Conformationally Locked Truncated 2-Hexynyl-N6-Substituted-(N)-Methanocarba-nucleosides as A3 Adenosine Receptor Antagonists and Partial Agonists," Journal of Medicinal Chemistry, vol. 57, No. 4, Jan. 2014 (pp. 1344-1354).
Paoletta et al., "Rational Design of Sulfonated A3 Adenosine Receptor-Selective Nucleosides as Pharmacological Tools to Study

(56) References Cited

OTHER PUBLICATIONS

Chronic Neuropathic Pain," Journal of Medicinal Chemistry, vol. 56, No. 14, Jun. 2013 (pp. 5949-5963).
Perreira et al., "Reversine' and its 2-Substituted Adenine Derivates as Potent and Selective A3 Adenosine Receptor Antagonists," The Journal of Medicinal Chemistry, vol. 48, No. 15, Jul. 2005 (pp. 4910-4918).
Pubchem, "Compound Summary for CID 69572716, SCHEMBL5803724," retrieved from <<https://pubchem.ncbi.nlm.nih.gov/compound/69572716#section=Top>> accessed on Mar. 17, 2017 (10 pages).
PubChem—CID-11623975, Create Date: Oct. 26, 2006, p. 2.
Pugliese et al., "Role of adenosine A3 receptors on CA1 hippocampal neurotransmission during oxygen-glucose deprivation episodes of different duration," Biochemical Pharmacology, vol. 74, No. 5, Sep. 2007 (pp. 768-779).
Ravi et al., "Adenine Nucleotide Analogues Locked in a Northern Methanocarba Conformation: Enhanced Stability and Potency as P2Y1 Receptor Agonists," Journal of Medicinal Chemistry, vol. 45, No. 10, May 2002 (pp. 2090-2100).
Shiniyakuhin, "Setting of the Standard and Test Method for New Pharmaceuticals," Iyakushinpatsu No. 568, May 1, 2001.
Takata, "API Form Screening and Selection in Drug Discovery Stage," Pharm Stage, vol. 6, No. 10, Jan. 15, 2007, pp. 20-25.
Tamada et al., "Calcium responses in subserosal interstitial cells of the guinea-pig proximal colon," Neurogastroenterology and motility: the official journal of the European Gastrointestinal Motility Society, vol. 26, No. 1, Jan. 2014 (pp. 115-123).
Tosh et al., "Click Modification in the N6 Region of A3 Adenosine Receptor-Selective Carbocyclic Nucleosides for Dendrimeric Tethering that Preserves Pharmacophore Recognition," Bioconjugate Chemistry, Feb. 2012, vol. 23, No. 2, pp. 232-247.
Tosh et al., "Methanocarba ring as a ribose modification in ligands of G protein-coupled purine and pyrimidine receptors: synthetic approaches," MedChemComm, vol. 2013, No. 4, Dec. 2013 (pp. 619-630).
Tosh et al., "Structural Sweet Spot for A1 Adenosine Receptor Activation by Truncated (N)-Methanocarba Nucleosides: Receptor Docking and Potent Anticonvulsant Activity," Journal of Medicinal Chemistry, Sep. 2012, vol. 55, No. 18, pp. 8075-8090.
Toti et al., "Synthesis and Evaluation of N6-Substituted Apioadenosines as Potential Adenosine A3 Receptor modulators," Bioorganic & Medicinal Chemistry Journal, Aug. 2014, vol. 22, No. 15, pp. 4257-4268.
Tracey et al., "Novel N6-substituted adenosine 5'-N-methyluronamindes with high selectivity for human adenosine A3 receptors reduce ischemic myocardial injury," American Journal of Physiology Heart and Circulatory Physiology, Dec. 2003, vol. 285, No. 6, pp. H2780-H2787.
Verzijl et al., "Functional selectivity of adenosine receptor ligands," Purinergic Signalling, vol. 7, May 2011 (pp. 171-192).
Vippagunta et al., "Crystalline solids," Adv Drug Deliv Rev. 2001; 48(1): 3-26.
Volpini et al., "Synthesis and biological evaluation of 2-alkynyl-N6-methyl-5'-N-methylcarboxamidoadenosine derivatives as potent and highly selective agonists for the human adenosine A3 receptor," Journal of Medicinal Chemistry, vol. 52, No. 23, Dec. 2009 (pp. 7897-7900).
Wan et al., "The A3 adenosine receptor agonist CP-532,903 [N6-(2,5-dichlorobenzyl)-3'-aminoadenosine-5'-N-methylcarboxamide] protects against myocardial ischemia/reperfusion injury via the sarcolemmal ATP-sensitive potassium channel," Journal of Pharmacology and Experimental Therapeutics, Jan. 2008, vol. 324, No. 1, pp. 234-243.
Warden et al., "Guidelines for the pharmacologic treatment of neurobehavioral sequelae of traumatic brain injury," Journal of Neurotrauma, vol. 23, No. 10, Oct. 2006 (pp. 1468-1501).
Wei et al., "Activation of the P2Y1 receptor induces apoptosis and inhibits proliferation of prostate cancer cells," Biochemical Pharmacology, vol. 82, No. 4, Aug. 2011 (pp. 418-425).
Wong et al., "Post exposure administration of A1 adenosine receptor agonists attenuates noise-induced hearing loss", Hearing Research, vol. 260, 2010 (pp. 81-88).
Yamano, "Approach to Crystal Polymorph in Process Research of New Drug," Journal of Synthetic Organic Chemistry, Sep. 1, 2007, vol. 65, No. 9, pp. 907-913.
Kawaguchi et al., "Drug and Crystal Polymorphism," Journal of Human Environmental Engineering, 2002, vol. 4, No. 2, pp. 310-317.
Ziganshin et al., "Characteristics of ecto-ATPase of Xenopus oocytes and the inhibitory actions of suramin on ATP breakdown," Pflugers Archiv: European journal of physiology, vol. 429, No. 3, Jan. 1995 (pp. 412-418).
Liston et al., "Nucleotide P2Y, receptor agonists are in vitro and in vivo prodrugs of A1/A3 adenosine receptor agonists . . . ," Purinergic Signalling, 2020; 16; 543-559.
PCT International Search Report from PCT/US2022/50743 dated Mar. 3, 2023.
Jacobson et al, "Historical and Current Adenosine Receptor Agonists in Preclinical and Clinical Development," Frontiers in Cellular Neuroscience, Mar. 2019, vol. 13, Article 124, p. 12, Figure 3, Formula 38.
Choi et al., "Preparative and Stereoselective Synthesis of the Versatile Intermediate for Carbocyclic Nucleosides:? Effects of the Bulky Protecting Groups to Enforce Facial Selectivity," J. Org. Chem. 2004; 69(7): 2634-2636.
Gao et al., "Allosteric modulation and functional selectivity of G protein-coupled receptors," Drug Discovery Today Technologies. 2013; 10(2): e237-e243.
Gillerman et al. "Investigations into the Origin of the Molecular Recognition of Several Adenosine Deaminase Inhibitors," J. Med. Chem. 2011; 54(1):107-121.
Jacobson et al., "Medicinal Chemistry of the A3 Adenosine Receptor: Agonists, Antagonists, and Receptor Engineering," Handbook Experimental Pharmacology, 2009; 193: 123-159.
Kenakin et al., "A simple method for quantifying functional selectivity and agonist bias," ACS Chem Neurosci. 2012; 3:193-203.
Klotz, "Adenosine receptors and their ligands," Naunyn Schmiedebergs Arch Pharmacol. 2000; 362(4-5): 382-391.
Liang et al., "A physiological role of the adenosine A3 receptor: Sustained cardioprotection," The Proceedings of the National Academy of Science, U.S.A. 1998; 95(12): 6995-6999.
Lin et al., "Ca2+ signaling, mitochondria and sensitivity to oxidative stress in aging astrocytes," Neurobiol Aging. 2007; 28(1): 99-111.
May et al., "Structure-function studies of allosteric agonism at M2 muscarinic acetylcholine receptors," Mol Pharmacol. 2007; 72:463-476.
McCall et al., "Selective Ablation of GIRK Channels in Dopamine Neurons Alters Behavioral Effects of Cocaine in Mice," Neuropsychopharmacology. 2017; 42(3): 707-715.
McCarthy et al., "Preparation of separate astroglial and oligodendroglial cell cultures from rat cerebral tissue," J Cell Biol. 1980; 85(3): 890-902.
Michel et al., "Total syntheses of a conformationally locked North-type methanocarba puromycin analogue and a dinucleotide derivative," Chemistry. 2009; 15(25):6244-57.
Stewart et al. "Determination of adenosine A1 receptor agonist and antagonist pharmacology using *Saccharomyces cerevisiae*: implications for ligand screening and functional selectivity," J Pharmacol Exp Ther. 2009; 331:277-286.
Tosh et al., "Structure-guided design of A3 adenosine receptor-selective nucleosides: combination of 2-arylethynyl and bicyclo[3.1.0]hexane sub-stitutions," J Med Chem. 2012; 55:4847-4860.
Tosh et al., "Truncated nucleosides as A3 adenosine receptor ligands: Combined 2-arylethynyl and bicyclohexane substitutions," ACS Med Chem Lett. 2012; 3:596-601.
Tosh et al., "Efficient, large-scale synthesis and preclinical studies of MRS5698, a highly selective A3 adenosine receptor agonist that protects against chronic neuropathic pain," Purinergic Signalling. 2015; 11(3): 371-387.

(56) References Cited

OTHER PUBLICATIONS

Van der Westhuizen et al., "Quanti-fication of ligand bias for clinically relevant b2-adrenergic receptor ligands: im-plications for drug taxonomy," Mol Pharmacol. 2014; 85:492-509.
Wootten et al., "Differential activation and modulation of the glucagon-like peptide-1 receptor by small molecule ligands," Mol Pharmacol. 2013; 83:822-834.
Wu et al., "Purinergic receptor-stimulated IP3-mediated Ca2+ release enhances neuroprotection by increasing astrocyte mitochondrial metabolism during aging," J Neurosci. 2007; 27(24): 6510-20.
Balbach, S., et al., "Pharmaceutical Evaluation of Early Development Candidates the 100 mg-approach", International Journal of Pharmaceutics, (May 4, 2004), 275(1-2): pp. 1-12.
Bastin, R.J., et al., "Salt Selection and Optimisation Procedures for Pharmaceutical New Chemical Entities," Organic Process Research & Development, (Sep. 2000), vol. 4, pp. 427-435.
Bischofberger, N., et al., "Adenosine A1 Receptor Agonists as Clinically Viable Agents for Treatment of Ischemic Brain Disorders," Annals of the New York Academy of Sciences, New York Academy of Sciences, US, (Jan. 1, 1997), vol. 825, pp. 23-29.
Caira, M.R., "Crystalline Polymorphism of Organic Compounds," Design of organic solids, Weber, E. et al "ED", Springer, 1998, pp. 164-208.
Fisher, E.S., et al., "Adenosine A1R/A3R Agonist AST-004 Reduces Brain Infarction In Mouse and Rat Models of Acute Ischemic Stroke," Frontiers in Stroke, (Nov. 22, 2022), vol. 1, pp. 2813-3056.
Jain, N.K., et al., "Polymorphism in Pharmacy," Indian Drugs, (1986), 23(6), pp. 315-329.
Sharpe A.L., et al., "Methamphetamine Self-Administration in Mice Decreases GIRK Channel-Mediated Currents in Midbrain Dopamine Neurons," International Journal of Neuropsychopharmacology, 2015, vol. 18, No. 5, 10 Pages.
Singhal, D., et al., "Drug Polymorphism and Dosage Form Design: a Practical Perspective," Advanced Drug Delivery Reviews, (Feb. 23, 2004), 56(3):335-347.
Zheng et al., "P2Y1R-initiated, IP3R-dependent stimulation of astrocyte mitochondrial metabolism reduces and partially reverses ischemic neuronal damage in mouse," J Cereb Blood Flow Metab. 2013; 33(4):600-11.
Zheng W., et al., "Purinergic Receptor Stimulation Reduces Cytotoxic Edema and Brain Infarcts in Mouse Induced by Photothrombosis by Energizing Glial Mitochondria," PLoS ONE, Dec. 22, 2010, vol. 5, Issue No. 12, e14401, 21 Pages.

* cited by examiner

PURINE NUCLEOSIDES, THEIR INTERMEDIATES, AND METHODS OF PREPARATION THEREOF

CROSS-REFERENCE TO RELATED APPLICATIONS

This application is a national stage filing under 35 U.S.C. § 371 of International Patent Application PCT/US2022/071971, filed Apr. 28, 2022; which claims the benefit of U.S. Provisional Application No. 63/180,872, filed on Apr. 28, 2021; the entire contents of which are incorporated herein by reference.

STATEMENT OF GOVERNMENT SUPPORT

This invention was made with government support under grant nos. ZIADK31116 and ZIADK31117 from the Intramural Research Program of NIDDK, National Institutes of Health. The government has certain rights in the present invention.

FIELD OF THE INVENTION

The present invention relates to compounds, methods for their preparation, intermediate compounds for their preparation, and methods of use of such compounds for treating, ameliorating, or promoting recovery from certain conditions of the brain, central nervous system (CNS), or cardiovascular system such as a brain injury, neurodegenerative conditions, and cardiac ischemia.

BACKGROUND OF THE INVENTION

Brain injuries are a distressingly common medical condition and one of the leading causes of morbidity and mortality worldwide. The brain is particularly susceptible to injury as neurons have a limited capacity to repair. When an individual is born, the brain already has essentially all the neurons it will have in life. Unlike other cells in the body, neurons stop reproducing shortly after birth. If these cells are injured or die, they are not replaced, often culminating in the disabling and largely irreversible degradation of a person's cognitive and sensorimotor capacity. Conditions that result in nerve cell death and damage range from ischemic episodes (e.g., stroke) and trauma, to degenerative disorders (e.g., Alzheimer's disease).

Injury to the Central Nervous System (CNS) is a substantial cause of death and disability worldwide. For example, according to the CDC approximately 1.7 million people sustain a Traumatic Brain Injury (TBI) annually, costing the U.S. economy in excess of $60 billion per year in terms of medical costs and lost productivity (Finkelstein, E; Corso, P; Miller, T, *The Incidence and Economic Burden of Injuries in the United States*, Oxford University Press: New York, 2006). Additionally, stroke is the third leading cause of death in the U.S. with an estimated incidence of 795,000 cases annually, a major cause of disability, and costing the U.S. economy over $34 billion per year (NINDS, 2014; stroke.nih.gov; and Mozaffarian D, Benjamin E J, Go A S, et al. "Heart disease and stroke statistics-2015 update: a report from the American Heart Association," *Circulation.* 2015; e29-322).

In the acute setting, there is an opportunity to treat patients within 24 hours that can limit the extent of the damage. Immediately after an ischemic or hemorrhagic stroke, the site of insult in the brain typically contains a core of tissue that is irreversibly damaged, and then also an area of viable but at-risk tissue called the penumbra. During this period, the insufficient oxygen and glucose supply to brain cells results in further secondary injury to the penumbra. The lack of oxygen and glucose decreases energy production by cell mitochondria. An immediate effect of this energy depletion is failure of the ion pumps, which by elevating extracellular potassium ($K^+$) ions, results in waves of recurrent spreading depolarizations in brain tissue. At the same time, influx of sodium ($Na^+$) ions into cells, followed by chloride ($Cl^-$) ions, results in the swelling of cells due to osmotic pressure elevation, pressuring nearby neurons and their processes, ultimately leading to lysis (cell rupture) and inflammatory responses. In general, this disruption of ion homeostasis leads to excitotoxicity, cell swelling and cell death that extends damage to adjacent tissue and expands lesions by secondary mechanisms. There is a need for effective treatments during the initial 24 hours to protect the stressed brain cells. The propagation of brain damage in stroke is similar to that observed in other forms of brain injury such as trauma and concussions.

Beyond acute treatment, effective astrocyte function plays a key role in broader neurorestoration—in the period 24-96 hours following brain insult, in the period months-years in patients with neurodegeneration such as Alzheimer's, or most generally in aged individuals. The inability of brain cells to regenerate requires the remaining intact brain tissue to reorganize in an attempt to recover any loss of function. This potential for neural reorganization is diminished in older individuals.

G-protein coupled receptors (GPCRs) have been suggested to mediate cardioprotective effects. Therefore, there is potential to treat heart and cardiovascular conditions by similar mechanisms of action via modulation of these receptors.

There is urgent and compelling unmet medical need for more effective treatments for brain injuries, CNS injuries, heart and cardiovascular diseases, and related conditions, as well as promoting neurorestoration in patients having a neurodegenerative condition such as Alzheimer's.

SUMMARY OF THE INVENTION

It has now been found that compounds of the present invention, and compositions thereof, are useful for treating, preventing ameliorating, or promoting recovery from certain injuries, diseases, or disorders of the brain, central nervous system (CNS), or cardiovascular system such as a brain injury, stroke, a neurodegenerative condition, cardiac ischemia, or an addiction or an addictive disorder. Such compounds are represented by Formula I:

I

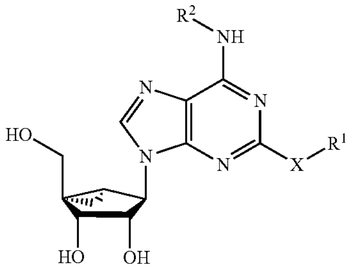

or a pharmaceutically acceptable salt thereof, wherein each variable is as defined herein.

In some embodiments, the present invention provides a method of preparing a compound of Formula I:

I

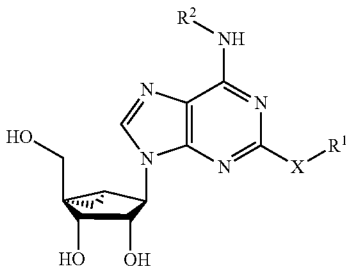

or a pharmaceutically acceptable salt thereof, wherein each variable is as defined herein.

In another aspect, the present invention provides intermediates useful in preparing a compound of Formula I.

In another aspect, the present invention provides a pharmaceutical composition comprising a compound of Formula I, or a pharmaceutically acceptable salt thereof.

Compounds of the present invention, and pharmaceutically acceptable compositions thereof, are useful for treating a variety of diseases, disorders or conditions, including those described herein.

DETAILED DESCRIPTION OF THE INVENTION

General Description of Certain Aspects of the Invention

It has now been found that compounds of the present invention, and compositions thereof, are useful for treating, preventing, ameliorating, or promoting recovery from certain injuries, diseases, or disorders of the brain, central nervous system (CNS), or cardiovascular system such as a brain injury, stroke, a neurodegenerative condition, cardiac ischemia, or an addiction or an addictive disorder. Such compounds are represented by Formula I:

I

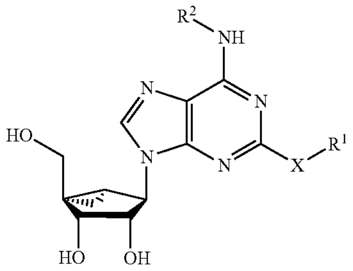

or a pharmaceutically acceptable salt thereof, wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; or X is a covalent bond when $R^1$ is a halogen; and n is 0, 1, 2, or 3.

U.S. Pat. Nos. 9,789,131 and 10,765,693, the entirety of each of which is hereby incorporated herein by reference, describe certain therapeutically beneficial compounds. Such compounds include compound I-1:

I-1

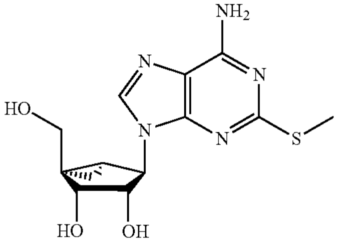

or a pharmaceutically acceptable salt thereof.

Compound I-1 is designated as MRS4322 in U.S. Pat. No. 9,789,131 and the synthesis of compound I-1 is described in detail at Example 9 of U.S. Pat. No. 9,789,131. Compound I-1 is designated as Compound A in U.S. Pat. No. 10,765,693 and its synthesis and preparation of solid forms thereof is described in detail at Example A and subsequent Examples therein.

It would be desirable to provide improved methods of synthesizing compound I-1 and additional compounds such as those of Formula I described herein, or a pharmaceutically acceptable salt thereof. Accordingly, the present invention provides methods of synthesizing such compounds and their pharmaceutically acceptable salts.

In some embodiments, the present invention provides improved methods of preparing a compound of Formula I and related compounds, wherein such methods produce the compounds in higher yield, fewer steps, milder conditions, and/or with greater generality (greater structural variation of the desired compounds). In some embodiments, the present invention provides, as described further herein, a method of preparing a compound of Formula I or a pharmaceutically acceptable salt thereof.

In another aspect, the present invention provides intermediates useful in preparing a compound of Formula I. Such intermediates include those described in detail below.

In another aspect, the present invention provides a compound of Formula I, or a pharmaceutically acceptable salt thereof, characterized in that the compound is prepared according to a method of synthesis described herein. In another aspect, the present invention provides a pharmaceutical composition comprising a compound of Formula I, or a pharmaceutically acceptable salt thereof, characterized in that the compound is prepared according to a method of synthesis described herein.

Compounds of the present invention, and pharmaceutically acceptable salts and pharmaceutical compositions thereof, are useful for treating, preventing, ameliorating, or promoting recovery from a variety of injuries, diseases, and disorders, including those described herein.

Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

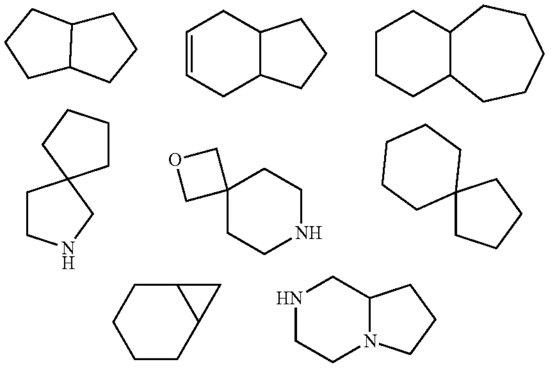

Exemplary bridged bicyclics include:

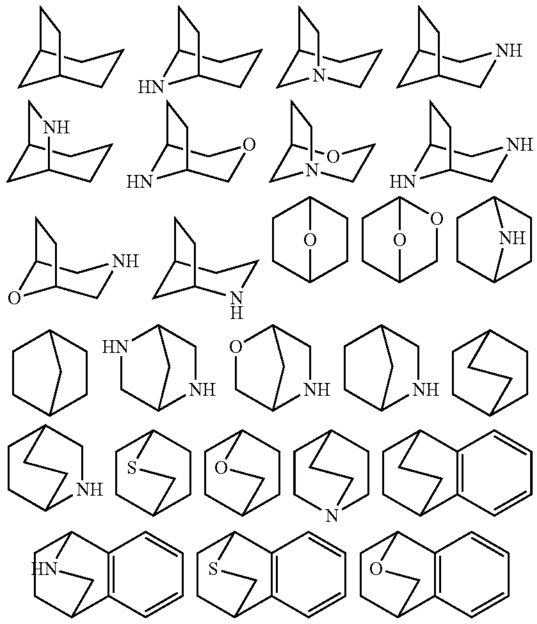

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A "substituted" alkylene chain is a polymethylene group in which one or more methylene hydrogen atoms are replaced with a substituent. Suitable substituents include those described below for a substituted aliphatic group.

The term "alkenylene" refers to a bivalent alkenyl group having at least one carbon-carbon double bond. Unless otherwise specified, the double bond may be cis or trans. In some embodiments, an alkenylene group has a single carbon-carbon double bond. In some embodiments, the double bond is cis. In some embodiments, the double bond is trans. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group having at least one carbon-carbon triple bond. A carbon-carbon triple bond may be located at an internal or terminal location in the alkynylene group, i.e., at either end or between two carbon atoms internal to the chain or carbon atoms. A substituted alkynylene chain is a polymethylene group containing at least one triple bond in which one or more hydrogen atoms are replaced with a substituent. Suitable substituents include those described below for a substituted aliphatic group. In some embodiments, the triple bond is at the terminal position and the alkynyl hydrogen is optionally replaced by a substituent.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH═CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR$—, $SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$SC(S)SR^{\circ}$, —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —($C_{1-4}$ straight or branched alkylene)O—$N(R^{\circ})_2$; or —($C_{1-4}$ straight or branched alkylene)C(O)O—$N(R^{\circ})_2$.

Each $R^{\circ}$ is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^{\circ}$ selected from ═O and ═S; or each $R^{\circ}$ is optionally substituted with a monovalent substituent independently selected from halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —($C_{1-4}$ straight or branched alkylene)$C(O)OR^{\bullet}$, or —$SSR^{\bullet}$.

Each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens; or wherein an optional substituent on a saturated carbon is a divalent substituent independently selected from ═O, ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2-3}O$—, or —$S(C(R^*_2))_{2-3}S$—, or a divalent substituent bound to vicinal substitutable carbons of an "optionally substituted" group is —$O(CR^*_2)_{2-3}O$—, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

An optional substituent on a substitutable nitrogen is independently —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^{\dagger}$ is $C_{1-4}$ aliphatic, $R^{\dagger}$ is optionally substituted with halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Description of Exemplary Embodiments

In one aspect, the present invention provides a compound of Formula I:

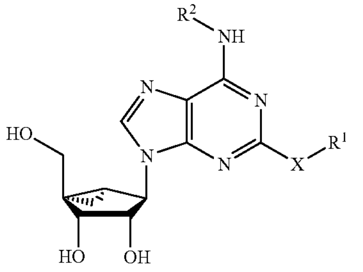

I or a pharmaceutically acceptable salt thereof, wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; or X is a covalent bond when $R^1$ is a halogen; and n is 0, 1, 2, or 3.

The definitions of variables in Formula I above encompass multiple chemical groups. The application contemplates embodiments where, for example, (i) the definition of a variable is a single chemical group selected from those chemical groups set forth above, (ii) the definition of a variable is a collection of two or more of the chemical groups selected from those set forth above, and (iii) the compound is defined by a combination of variables in which the variables are defined by (i) or (ii).

In certain embodiments, the compound is a compound of Formula I.

As defined generally above, $R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond.

In some embodiments, $R^1$ is $C_{1-8}$ alkyl substituted with n instances of $R^3$. In some embodiments, $R^1$ is —($C_{1-4}$ alkylene)-Ar substituted with n instances of $R^3$. In some embodiments, $R^1$ is —($C_{1-4}$ alkylene)-Cy substituted with n instances of $R^3$. In some embodiments, $R^1$ is $C_{2-8}$ alkenyl substituted with n instances of $R^3$. In some embodiments, $R^1$ is —($C_{2-4}$ alkenylene)-Ar substituted with n instances of $R^3$. In some embodiments, $R^1$ is —($C_{2-4}$ alkenylene)-Cy substituted with n instances of $R^3$. In some embodiments, $R^1$ is $C_{2-8}$ alkynyl substituted with n instances of $R^3$. In some embodiments, $R^1$ is —($C_{2-4}$ alkynylene)-Ar substituted with n instances of $R^3$. In some embodiments, $R^1$ is —($C_{2-4}$ alkynylene)-Cy substituted with n instances of $R^3$. In some embodiments, $R^1$ is phenyl substituted with n instances of $R^3$. In some embodiments, $R^1$ is Cy substituted with n instances of $R^3$. In some embodiments, $R^1$ is a 5-6 membered monocyclic heteroaromatic ring having 1, 2, 3, or 4 heteroatoms independently selected from nitrogen, oxygen, and sulfur; wherein said ring is substituted with n instances of $R^3$. In some embodiments, X is a covalent bond and $R^1$ is a halogen.

In some embodiments, $R^1$ is $C_{1-8}$ alkyl, —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$.

In some embodiments, $R^1$ is $C_{1-8}$ alkyl, —($C_{1-4}$ alkylene)-phenyl, —($C_{1-4}$ alkylene)-($C_{3-8}$ cycloalkyl), $C_{2-8}$ alkenyl, or $C_{2-8}$ alkynyl; each of which is substituted with n instances of $R^3$. In some embodiments, $R^1$ is $C_{1-8}$ alkyl, —($C_{1-2}$ alkylene)-phenyl, or —($C_{1-2}$ alkylene)-($C_{3-5}$ cycloalkyl); each of which is substituted with n instances of $R^3$. In some embodiments, $R^1$ is $C_{1-8}$ alkyl, —($C_{1-2}$ alkylene)-phenyl, or —($C_{1-2}$ alkylene)-($C_{3-5}$ cycloalkyl). In some embodiments, $R^1$ is —($C_{1-2}$ alkylene)-phenyl or —($C_{1-2}$ alkylene)-($C_{3-5}$ cycloalkyl).

In some embodiments, $R^1$ is $C_{1-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$.

In some embodiments, $R^1$ is $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$.

In some embodiments, $R^1$ is $C_{1-6}$ alkyl substituted with n instances of $R^3$. In some embodiments, $R^1$ is $C_{1-4}$ alkyl substituted with n instances of $R^3$. In some embodiments, $R^1$ is $C_{3-8}$ alkyl substituted with n instances of $R^3$. In some embodiments, $R^1$ is $C_{3-6}$ alkyl substituted with n instances of $R^3$. In some embodiments, $R^1$ is $C_{3-4}$ alkyl substituted with n instances of $R^3$. In some embodiments, $R^1$ is (i) $C_{1-2}$ alkyl substituted with 1, 2, or 3 instances of $R^3$, or (ii) $C_{3-8}$ alkyl substituted with n instances of $R^3$. In some embodiments, $R^1$ is $C_{1-8}$ alkyl substituted with 1, 2, or 3 instances of $R^3$. In some embodiments, $R^1$ is —($C_{1-4}$ alkylene)-phenyl substituted with n instances of $R^3$. In some embodiments, $R^1$ is —($C_{1-2}$ alkylene)-phenyl substituted with n instances of $R^3$. In some embodiments, $R^1$ is —($C_{1-4}$ alkylene)-($C_{3-8}$ cycloalkyl) substituted with n instances of $R^3$. In some embodiments, $R^1$ is —($C_{1-2}$ alkylene)-($C_{3-5}$ cycloalkyl) substituted with n instances of $R^3$. In some embodiments, $R^1$ is $C_{3-8}$ cycloalkyl substituted with n instances of $R^3$. In some embodiments, $R^1$ is $C_{3-6}$ cycloalkyl substituted with n instances of $R^3$.

In some embodiments, $R^1$ is $C_{1-8}$ alkyl. In some embodiments, $R^1$ is $C_{1-6}$ alkyl. In some embodiments, $R^1$ is $C_{1-4}$ alkyl. In some embodiments, $R^1$ is methyl or ethyl. In some embodiments, $R^1$ is methyl. In some embodiments, $R^1$ is ethyl. In some embodiments, $R^1$ is $C_{3-8}$ alkyl. In some embodiments, $R^1$ is $C_{3-6}$ alkyl. In some embodiments, $R^1$ is $C_{3-4}$ alkyl. In some embodiments, $R^1$ is —($C_{1-4}$ alkylene)-phenyl. In some embodiments, $R^1$ is —($C_{1-2}$ alkylene)-phenyl. In some embodiments, $R^1$ is —($C_{1-4}$ alkylene)-($C_{3-8}$ cycloalkyl). In some embodiments, $R^1$ is —($C_{1-2}$ alkylene)-($C_{3-5}$ cycloalkyl). In some embodiments, $R^1$ is $C_{2-8}$ alkenyl. In some embodiments, $R^1$ is $C_{2-8}$ alkynyl. In some embodiments, $R^1$ is $C_{3-8}$ cycloalkyl. In some embodiments, $R^1$ is $C_{3-6}$ cycloalkyl. In some embodiments, $R^1$ is phenyl. In some embodiments, $R^1$ is a 5-6 membered monocyclic heteroaromatic ring having 1-4 heteroatoms independently selected from nitrogen, oxygen, and sulfur.

In some embodiments, $R^1$ is (i) $C_{1-2}$ alkyl substituted with 1, 2, or 3 instances of $R^3$, or (ii) $C_{3-8}$ alkyl, —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$. In some embodiments, $R^1$ is (i) $C_{1-8}$ alkyl substituted with 1, 2, or 3 instances of $R^3$, or (ii) —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$. In some embodiments, $R^1$ is (i) $C_{1-2}$ alkyl substituted with 1, 2, or 3 instances of $R^3$, or (ii) $C_{3-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$. In some embodiments, $R^1$ is $C_{3-8}$ alkyl, —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$. In some embodiments, $R^1$ is —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$.

In some embodiments, X is a covalent bond and $R^1$ is a halogen selected from F or Cl. In some embodiments, $R^1$ is F. In some embodiments, $R^1$ is Cl.

In some embodiments, $R^1$ is selected from those depicted in Table 1, below.

As defined generally above, Ar is phenyl or a 5-6 membered monocyclic heteroaromatic ring having 1, 2, 3, or 4 heteroatoms independently selected from nitrogen, oxygen, and sulfur.

In some embodiments, Ar is phenyl. In some embodiments, Ar is a 5-6 membered monocyclic heteroaromatic ring having 1, 2, 3, or 4 heteroatoms independently selected from nitrogen, oxygen, and sulfur.

In some embodiments, Ar is selected from those depicted in Table 1, below.

As defined generally above, Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur.

In some embodiments, Cy is a 3-8 membered saturated or partially unsaturated monocyclic carbocyclic ring. In some embodiments, Cy is a 3-8 membered saturated monocyclic carbocyclic ring. In some embodiments, Cy is a 3-6 membered saturated monocyclic carbocyclic ring. In some embodiments, Cy is a 7-12 membered saturated or partially unsaturated bicyclic carbocyclic ring. In some embodiments, Cy is a 3-6-membered saturated or partially unsaturated monocyclic heterocyclic ring having 1 or 2 heteroatoms independently selected from nitrogen, oxygen, and sulfur.

In some embodiments, Cy is selected from those depicted in Table 1, below.

As defined generally above, $R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms.

In some embodiments, $R^2$ is $C_{1-4}$ alkyl or $C_{3-5}$ cycloalkyl; each of which is optionally substituted with 1, 2, or 3 deuterium or halogen atoms. In some embodiments, $R^2$ is $C_{1-4}$ alkyl optionally substituted with 1, 2, or 3 deuterium or halogen atoms. In some embodiments, $R^2$ is $C_{1-4}$ alkyl substituted with 1, 2, or 3 deuterium or halogen atoms. In some embodiments, $R^2$ is $C_{3-5}$ cycloalkyl optionally substituted with 1, 2, or 3 deuterium or halogen atoms. In some embodiments, $R^2$ is $C_{3-5}$ cycloalkyl substituted with 1, 2, or 3 deuterium or halogen atoms.

In some embodiments, $R^2$ is hydrogen, $C_{1-4}$ alkyl, or $C_{3-5}$ cycloalkyl. In some embodiments, $R^2$ is hydrogen or $C_{1-4}$ alkyl. In some embodiments, $R^2$ is $C_{1-4}$ alkyl or $C_{3-5}$ cycloalkyl. In some embodiments, $R^2$ is hydrogen. In some embodiments, $R^2$ is $C_{1-4}$ alkyl. In some embodiments, $R^2$ is methyl or ethyl. In some embodiments, $R^2$ is methyl. In some embodiments, $R^2$ is $C_{3-5}$ cycloalkyl. In some embodiments, $R^2$ is cyclopropyl.

In some embodiments, $R^2$ is selected from those depicted in Table 1, below.

As defined generally above, each $R^3$ is independently deuterium, halogen, —CN, —O—($C_{1-4}$ alkyl), —OH, —S—($C_{1-4}$ alkyl), or —SH.

In some embodiments, each $R^3$ is independently halogen, —O—($C_{1-4}$ alkyl), —OH, —S—($C_{1-4}$ alkyl), or —SH. In some embodiments, each $R^3$ is deuterium. In some embodiments, each $R^3$ is independently halogen. In some embodiments, each $R^3$ is independently fluoro or chloro. In some embodiments, $R^3$ is fluoro. In some embodiments, each $R^3$ is —CN. In some embodiments, each $R^3$ is independently —O—($C_{1-4}$ alkyl) or —OH. In some embodiments, each $R^3$ is independently —O—($C_{1-4}$ alkyl). In some embodiments, $R^3$ is —OH. In some embodiments, each $R^3$ is independently —S—($C_{1-4}$ alkyl) or —SH. In some embodiments, each $R^3$ is independently —S—($C_{1-4}$ alkyl). In some embodiments, $R^3$ is —SH.

In some embodiments, $R^3$ is selected from those depicted in Table 1, below.

As defined generally above, X is S or O; or X is a covalent bond when $R^1$ is halogen. In some embodiments, X is S. In some embodiments, X is O. In some embodiments, X is a covalent bond and $R^1$ is halogen. In some embodiments, $R^1$ is selected from those depicted in Table 1, below.

As defined generally above, n is 0, 1, 2, or 3. In some embodiments, n is 0. In some embodiments, n is 1. In some embodiments, n is 2. In some embodiments, n is 3. In some embodiments, n is 0 or 1. In some embodiments, n is 1 or 2. In some embodiments, n is 2 or 3. In some embodiments, n is 0, 1, or 2. In some embodiments, n is 1, 2, or 3. In some embodiments, n is selected from those depicted in Table 1, below.

In some embodiments, the compound of Formula I is a compound other than a compound selected from those described in U.S. Pat. No. 9,789,131. In some embodiments, the compound of Formula I is a compound other than a compound selected from the following:

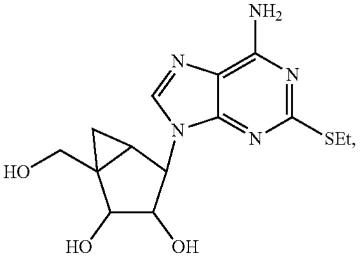

,

-continued

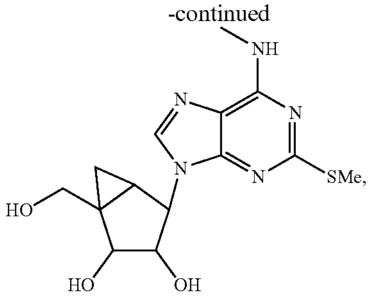

, and

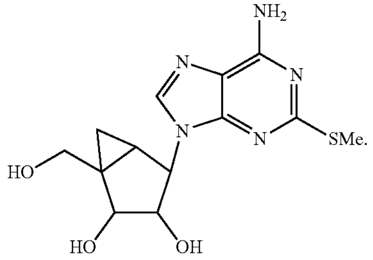

.

The description above describes multiple embodiments relating to compounds of Formula I. The patent application specifically contemplates all combinations of the embodiments.

In one aspect, the present invention provides a compound of Formula I-A:

I-A

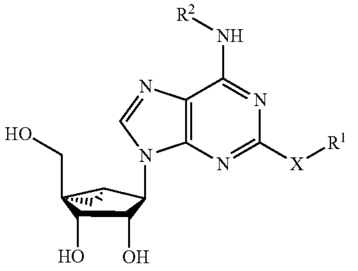

or a pharmaceutically acceptable salt thereof, wherein:

$R^1$ is (i) $C_{1-2}$ alkyl substituted with 1, 2, or 3 instances of $R^3$, or (ii) $C_{3-8}$ alkyl, —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$;

$R^2$ is hydrogen, $C_{1-4}$ alkyl, or $C_{3-5}$ cycloalkyl;

each $R^3$ is independently halogen, —O—($C_{1-4}$ alkyl), —OH, —S—($C_{1-4}$ alkyl), or —SH;

X is S or O; and n is 0, 1, 2, or 3.

In one aspect, the present invention provides a compound of Formula I-B:

I-B

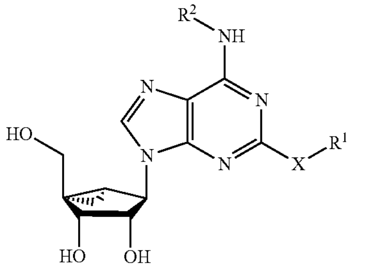

or a pharmaceutically acceptable salt thereof, wherein:

$R^1$ is a halogen;

$R^2$ is hydrogen, $C_{1-4}$ alkyl, or $C_{3-5}$ cycloalkyl; and

X is a covalent bond.

The definitions of variables in Formula I-A and I-B above encompass multiple chemical groups. The application contemplates embodiments where, for example, (i) the definition of a variable is a single chemical group selected from those chemical groups set forth above, (ii) the definition of a variable is a collection of two or more of the chemical groups selected from those set forth above, and (iii) the compound is defined by a combination of variables in which the variables are defined by (i) or (ii).

In certain embodiments, the compound is a compound of Formula I-A. In certain embodiments, the compound is a compound of Formula I-B.

As defined generally above, $R^1$ is (i) $C_{1-2}$ alkyl substituted with 1, 2, or 3 instances of $R^3$, or (ii) $C_{3-8}$ alkyl, —($C_{1-4}$ alkylene)-phenyl, —($C_{1-4}$ alkylene)-($C_{3-8}$ cycloalkyl), $C_{2-8}$ alkenyl, $C_{2-9}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$.

In some embodiments, $R^1$ is (i) $C_{1-2}$ alkyl substituted with 1, 2, or 3 instances of $R^3$, or (ii) $C_{3-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$.

In some embodiments, $R^1$ is $C_{1-2}$ alkyl substituted with 1, 2, or 3 instances of $R^3$. In some embodiments, $R^1$ is $C_{3-8}$ alkyl, —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$.

In some embodiments, $R^1$ is —($C_{1-4}$ alkylene)-phenyl, —($C_{1-4}$ alkylene)-($C_{3-8}$ cycloalkyl), $C_{2-8}$ alkenyl, or $C_{2-8}$ alkynyl; each of which is substituted with n instances of $R^3$. In some embodiments, $R^1$ is —($C_{1-2}$ alkylene)-phenyl or —($C_{1-2}$ alkylene)-($C_{3-5}$ cycloalkyl); each of which is substituted with n instances of $R^3$. In some embodiments, $R^1$ is —($C_{1-2}$ alkylene)-phenyl or —($C_{1-2}$ alkylene)-($C_{3-5}$ cycloalkyl).

In some embodiments, $R^1$ is $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$.

In some embodiments, $R^1$ is $C_{3-8}$ alkyl substituted with n instances of $R^3$. In some embodiments, $R^1$ is $C_{3-6}$ alkyl substituted with n instances of $R^3$. In some embodiments, $R^1$ is $C_3$. 4 alkyl substituted with n instances of $R^3$. In some embodiments, $R^1$ is —($C_{1-4}$ alkylene)-phenyl substituted with n instances of $R^3$. In some embodiments, $R^1$ is —($C_{1-2}$ alkylene)-phenyl substituted with n instances of $R^3$. In some embodiments, $R^1$ is —($C_{1-4}$ alkylene)-($C_{3-8}$ cycloalkyl) substituted with n instances of $R^3$. In some embodiments, $R^1$ is —($C_{1-2}$ alkylene)-($C_{3-5}$ cycloalkyl) substituted with n instances of $R^3$. In some embodiments, $R^1$ is $C_{2-8}$ alkenyl substituted with n instances of $R^3$. In some embodiments, $R^1$ is $C_{2-8}$ alkynyl substituted with n instances of $R^3$. In some embodiments, $R^1$ is $C_{3-8}$ cycloalkyl substituted with n instances of $R^3$. In some embodiments, $R^1$ is $C_{3-6}$ cycloalkyl substituted with n instances of $R^3$. In some embodiments, $R^1$ is phenyl substituted with n instances of $R^3$. In some embodiments, $R^1$ is a 5-6 membered monocyclic heteroaromatic ring having 1-4 heteroatoms independently selected from nitrogen, oxygen, and sulfur; wherein said ring is substituted with n instances of $R^3$.

In some embodiments, $R^1$ is $C_{3-8}$ alkyl. In some embodiments, $R^1$ is $C_{3-6}$ alkyl. In some embodiments, $R^1$ is $C_{3-4}$ alkyl. In some embodiments, $R^1$ is —($C_{1-4}$ alkylene)-phenyl. In some embodiments, $R^1$ is —($C_{1-2}$ alkylene)-phenyl. In some embodiments, $R^1$ is —($C_{1-4}$ alkylene)-($C_{3-8}$ cycloalkyl). In some embodiments, $R^1$ is —($C_{1-2}$ alkylene)-($C_{3-5}$ cycloalkyl). In some embodiments, $R^1$ is $C_{2-8}$ alkenyl. In some embodiments, $R^1$ is $C_{2-8}$ alkynyl. In some embodiments, $R^1$ is $C_{3-8}$ cycloalkyl. In some embodiments, $R^1$ is $C_{3-6}$ cycloalkyl. In some embodiments, $R^1$ is phenyl. In some embodiments, $R^1$ is a 5-6 membered monocyclic heteroaromatic ring having 1-4 heteroatoms independently selected from nitrogen, oxygen, and sulfur.

In some embodiments, $R^1$ is (i) $C_{1-8}$ alkyl substituted with 1, 2, or 3 instances of $R^3$, or (ii) —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$. In some embodiments, $R^1$ is $C_{3-8}$ alkyl, —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$. In some embodiments, $R^1$ is —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$.

In some embodiments, $R^1$ is selected from those depicted in compounds I-3 through I-21 in Table 1, below.

As defined generally above, $R^2$ is hydrogen, $C_{1-4}$ alkyl, or $C_{3-5}$ cycloalkyl.

In some embodiments, $R^2$ is hydrogen or $C_{1-4}$ alkyl. In some embodiments, $R^2$ is $C_{1-4}$ alkyl or $C_{3-5}$ cycloalkyl. In some embodiments, $R^2$ is hydrogen. In some embodiments, $R^2$ is $C_{1-4}$ alkyl. In some embodiments, $R^2$ is methyl or ethyl. In some embodiments, $R^2$ is methyl. In some embodiments, $R^2$ is $C_{3-5}$ cycloalkyl. In some embodiments, $R^2$ is cyclopropyl.

In some embodiments, $R^2$ is selected from those depicted in Table 1, below.

As defined generally above, each $R^3$ is independently halogen, —O—($C_{1-4}$ alkyl), —OH, —S—($C_{1-4}$ alkyl), or —SH.

In some embodiments, each $R^3$ is independently halogen. In some embodiments, each $R^3$ is independently fluoro or chloro. In some embodiments, $R^3$ is fluoro. In some embodiments, each $R^3$ is independently —O—($C_{1-4}$ alkyl) or —OH. In some embodiments, each $R^3$ is independently —O—($C_{1-4}$ alkyl). In some embodiments, $R^3$ is —OH. In some embodiments, each $R^3$ is independently —S—($C_{1-4}$ alkyl) or —SH. In some embodiments, each $R^3$ is independently —S—($C_{1-4}$ alkyl). In some embodiments, $R^3$ is —SH.

In some embodiments, $R^3$ is selected from those depicted in Table 1, below.

As defined generally above, X is S or O. In some embodiments, X is S. In some embodiments, X is O. In some embodiments, $R^1$ is selected from those depicted in Table 1, below.

As defined generally above, n is 0, 1, 2, or 3. In some embodiments, n is 0. In some embodiments, n is 1. In some embodiments, n is 2. In some embodiments, n is 3. In some embodiments, n is 0 or 1. In some embodiments, n is 1 or 2. In some embodiments, n is 2 or 3. In some embodiments, n is 0, 1, or 2. In some embodiments, n is 1, 2, or 3. In some embodiments, n is selected from those depicted in Table 1, below.

The description above describes multiple embodiments relating to compounds of Formula I-A. The patent application specifically contemplates all combinations of the embodiments.

In some embodiments, the present invention provides a compound selected from one of those in Table 1, or a pharmaceutically acceptable salt thereof. In some embodiments, the present invention provides a compound selected from I-3 through I-21 in Table 1, or a pharmaceutically acceptable salt thereof.

As defined generally above for Formula I-B, $R^1$ is a halogen. In some embodiments, $R^1$ is F. In some embodiments, $R^1$ is Cl. In some embodiments, $R^1$ is Br. In some embodiments, $R^1$ is I.

As defined generally above for Formula I-B, $R^2$ is hydrogen, $C_{1-4}$ alkyl, or $C_{3-5}$ cycloalkyl.

In some embodiments, $R^2$ is hydrogen or $C_{1-4}$ alkyl. In some embodiments, $R^2$ is $C_{1-4}$ alkyl or $C_{3-5}$ cycloalkyl. In some embodiments, $R^2$ is hydrogen. In some embodiments, $R^2$ is $C_{1-4}$ alkyl. In some embodiments, $R^2$ is methyl or ethyl. In some embodiments, $R^2$ is methyl. In some embodiments, $R^2$ is $C_{3-5}$ cycloalkyl. In some embodiments, $R^2$ is cyclopropyl.

In some embodiments, the compound of Formula I-B is:

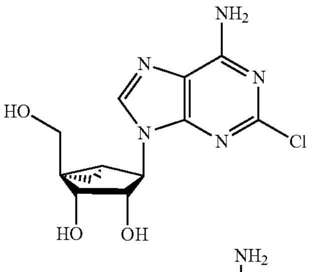

or

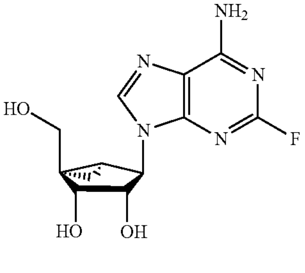

or a pharmaceutically acceptable salt thereof.

In some embodiments, the compound of Formula I-B is other than

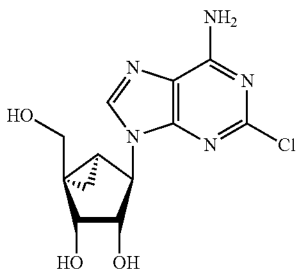

or a pharmaceutically acceptable salt thereof.

In another aspect, the present invention provides a compound selected from one of those in Table 1, or a pharmaceutically acceptable salt thereof. In another aspect, the present invention provides a mono-, di-, or tri-phosphate of a compound of Formula I, I-A, or I-B, such as a compound depicted in Table 1, or a pharmaceutically acceptable salt thereof, or a prodrug thereof. In some embodiments, the prodrug of the mono-, di-, or tri-phosphate is a corresponding mono-, di-, or tri-phosphate ester such as an alkyl or phenyl ester thereof. Exemplary prodrugs of phosphates are described in U.S. Pat. No. 9,724,360, the contents of which are hereby incorporated by reference.

TABLE 1

Exemplary Compounds of the Present Invention

| Compound # | Structure |
|---|---|
| I-1 | 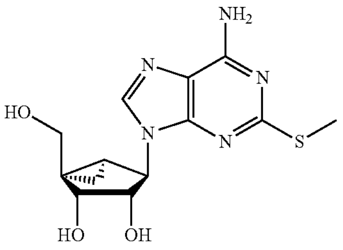 |
| I-2 | 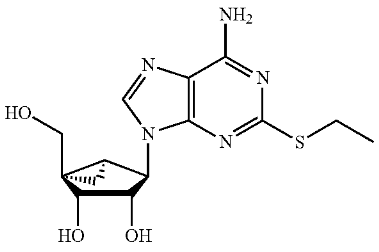 |
| I-3 | 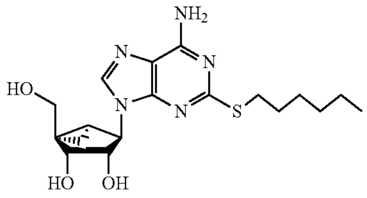 |

TABLE 1-continued
| Exemplary Compounds of the Present Invention | |
| --- | --- |
| Compound # | Structure |
| I-4 | 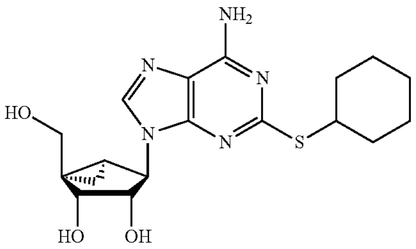 |
| I-5 | 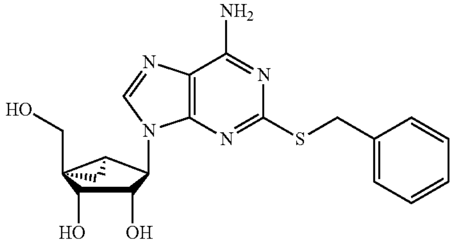 |
| I-6 | 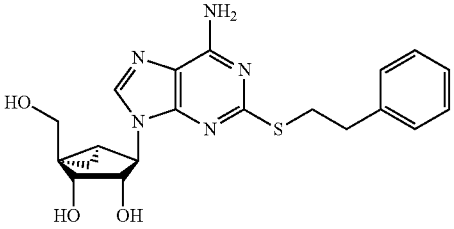 |
| I-7 | 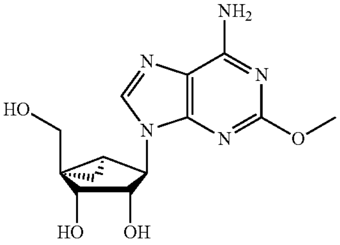 |
| I-8 | 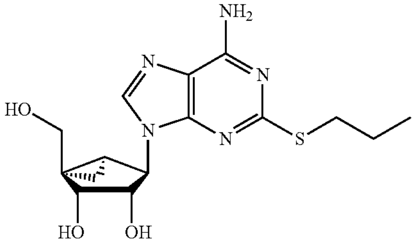 |
| I-9 | 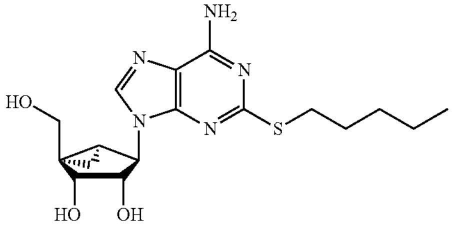 |
TABLE 1-continued
| Exemplary Compounds of the Present Invention | |
| --- | --- |
| Compound # | Structure |
| I-10 | 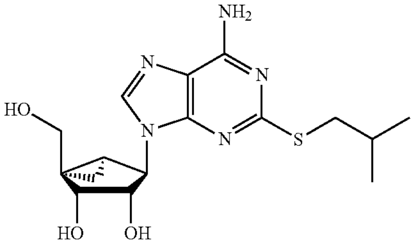 |
| I-11 | 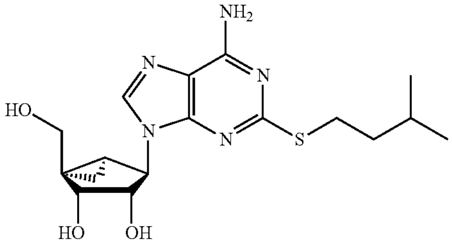 |
| I-12 | 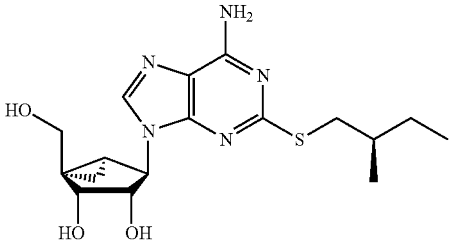 |
| I-13 | 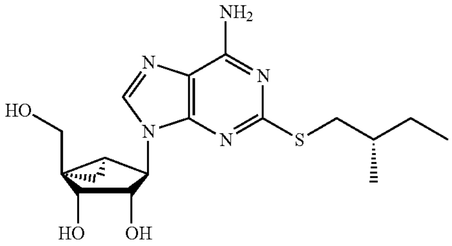 |
| I-14 | 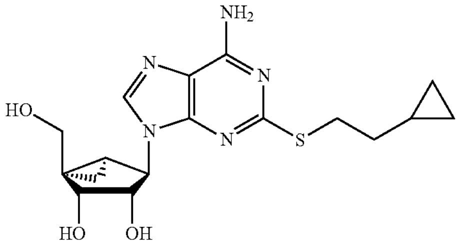 |
| I-15 | 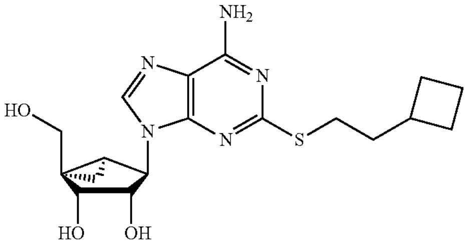 |

TABLE 1-continued

| Exemplary Compounds of the Present Invention | |
|---|---|
| Compound # | Structure |
| I-16 | 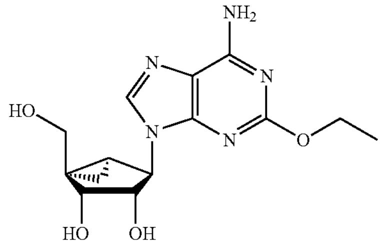 |
| I-17 | 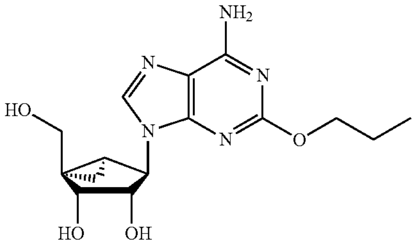 |
| I-18 | 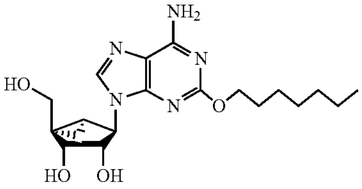 |
| I-19 | 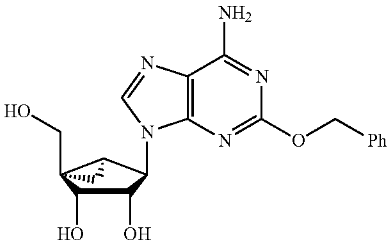 |
| I-20 | 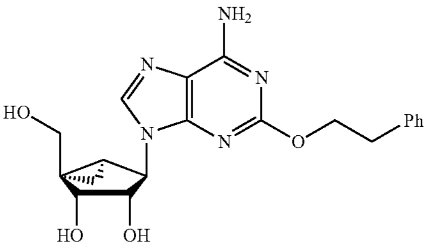 |

TABLE 1-continued

| Exemplary Compounds of the Present Invention | |
|---|---|
| Compound # | Structure |
| I-21 | 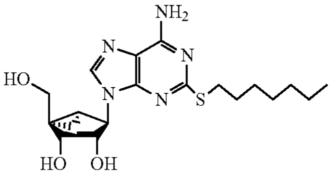 |
| I-22 | 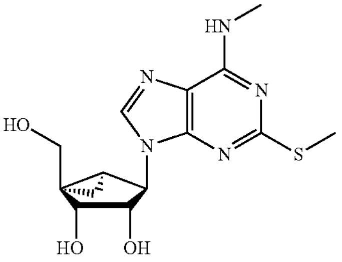 |
| I-23 | 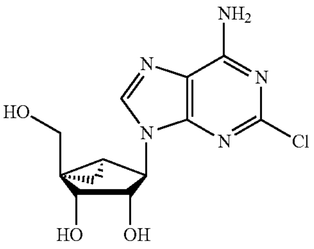 |
| I-24 | 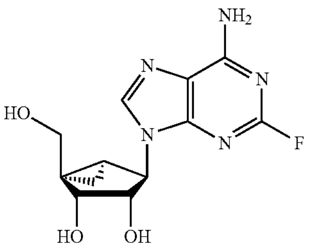 |

Exemplary Methods of Synthesis

As described above, the present invention provides methods of synthesizing compounds of Formula I, I-A, or I-B and pharmaceutically acceptable salts thereof. In some embodiments, the present compounds are generally prepared according to Scheme I set forth below:

Scheme I

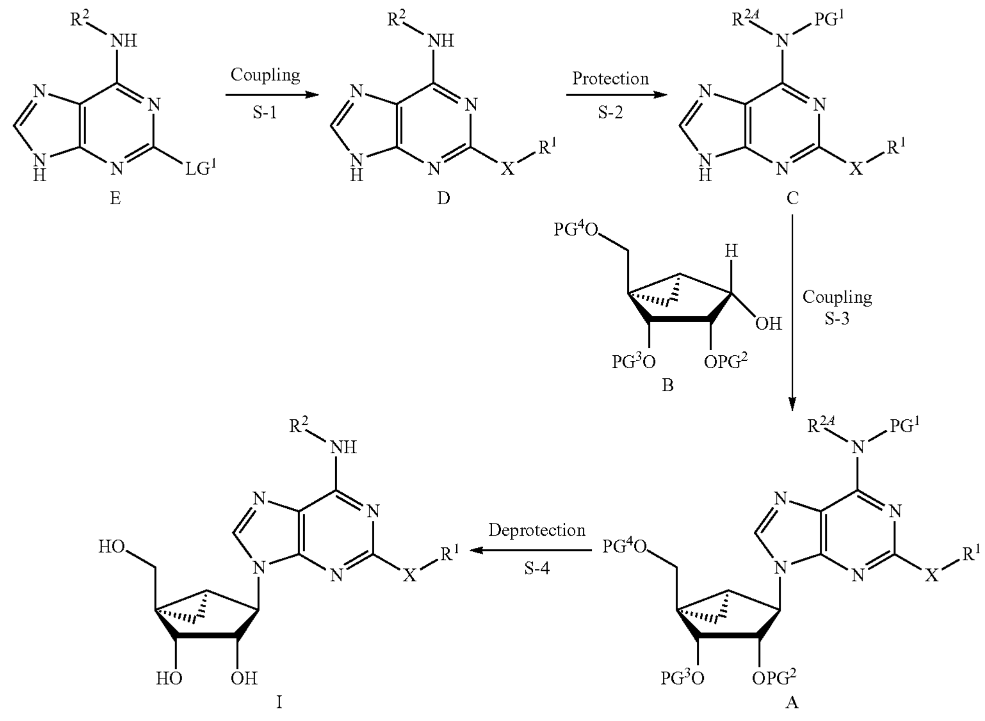

In Scheme I above, each of X, $R^1$, $R^2$, $R^{2A}$, $PG^1$, $PG^2$, $PG^3$, and $PG^4$ is as defined and described in embodiments herein, both singly and in combination.

General principles of organic chemistry and synthesis, well known in the art, are described in, for example, "Organic Chemistry", Thomas Sorrell, University Science Books, Sausalito: 1999; "March's Advanced Organic Chemistry", $5^{th}$ Ed., Ed.: Smith, M. B. and March, J., John Wiley & Sons, New York: 2001; and "Comprehensive Organic Synthesis", $2^{nd}$ Ed., Ed.: Knochel, P. and Molander, G. A., Elsevier, Amsterdam: 2014; the entire contents of each of which are hereby incorporated by reference.

In one aspect, the present invention provides methods for preparing N-protected adenine 2-thioether and 2-ether nucleobases of formula C according to the steps depicted in Scheme I, above. At step S-1, a thiol or alcohol of formula $R^1$—X—H is coupled with an adenine nucleobase of formula E. In some embodiments, the coupling is conducted in the presence of a suitable base. Alternatively, the corresponding thiol or alcohol metal salt of formula $R^1$—X-M (wherein M is a metal atom, such as sodium or potassium), is coupled with an adenine nucleobase of formula E.

The $LG^1$ group of formula E is a suitable leaving group. Suitable leaving groups are well known in the art, as described in, for example, the references described above. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyl (mesyl), tosyl, triflate, nitrophenylsulfonyl (nosyl), and bromo-phenylsulfonyl (brosyl). In certain embodiments, $LG^1$ is chloro, fluoro, or triflate. In certain embodiments, $LG^1$ is chloro. In some embodiments, when —X—$R^1$ is halogen in Formula I or I-B above, step S-1 is omitted ($LG^1$ is halogen, e.g., chloro, and does not need to undergo any chemical transformation).

At step S-2, adenine 2-halo, 2-thioether, or 2-ether nucleobase D is protected to afford N-protected adenine 2-halo, 2-thioether or 2-ether nucleobases of formula C.

The $PG^1$ group of formulae C and A is a suitable amino protecting group. Suitable amino protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable amino protecting groups, taken with the —N($R^{2A}$)— moiety to which it is attached, include, but are not limited to, aralkylamines, carbamates, allyl amines, amides, and the like. Examples of $PG^1$ groups of formulae C and A include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like. In some embodiments, $PG^1$ is an acid-labile amino protecting group. In some embodiments, $PG^1$ taken with the —N($R^{2A}$)— moiety to which it is attached is an acid-labile carbamate. In some embodiments, $PG^1$ is BOC.

One of ordinary skill in the art will recognize that when $R^2$ in nucleobase D is hydrogen, $R^{2A}$ in nucleobase C may be hydrogen (from addition of a single protecting group to nucleobase D) or a suitable amino protecting group (from addition of a second protecting group to nucleobase D), depending on the reaction conditions (for example, the stoichiometry of nucleobase D relative to protecting group reagents). Accordingly, in some embodiments, $R^{2A}$ is hydrogen. In other embodiments, $R^{2A}$ is a suitable amino protecting group. In some embodiments, $R^{2A}$ is an acid-labile amino protecting group. In some embodiments, $R^{2A}$ taken with the —N($PG^1$)- moiety to which it is attached is an acid-labile carbamate. In some embodiments, $R^{2A}$ is BOC. In some embodiments, $PG^1$ and $R^{2A}$ are each BOC. In other embodiments, $R^{2A}$ and $PG^1$ are taken together to form a suitable bivalent nitrogen protecting group, such as phthalimide or tetramethylsuccinimide. In some embodiments, $R^{2A}$ and $PG^1$ are taken together with the nitrogen to which they are attached to form phthalimide.

At step S-3, an N-protected adenine 2-halo, 2-thioether or 2-ether nucleobase of formula C undergoes coupling with protected (N)-methanocarba sugar analogue B to afford (N)-methanocarba nucleoside analogue A. In some embodiments, the coupling is conducted under Mitsunobu-type conditions.

Each of the $PG^2$, $PG^3$, and $PG^4$ groups of formulae B and A is independently a suitable hydroxyl protecting group. Suitable hydroxyl protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. In certain embodiments, each of $PG^2$, $PG^3$, and $PG^4$, taken with the oxygen atom to which it is bound, is independently selected from esters, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, or carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl) ethoxymethyl, and tetrahydropyranyl ethers. Examples of arylalkyl ethers include benzyl, p-methoxybenzyl (MPM), 3,4-dimethoxybenzyl, o-nitrobenzyl, p-nitrobenzyl, p-halobenzyl, 2,6-dichlorobenzyl, p-cyanobenzyl, trityl, 2- and 4-picolyl.

In some embodiments, each of $PG^2$, $PG^3$, and $PG^4$ is independently an acid-labile hydroxyl protecting group.

In some embodiments, $PG^4$ taken with the oxygen atom to which it is bound is a silyl ether or arylalkyl ether. In some embodiments, $PG^4$ taken with the oxygen atom to which it is bound is an acid-labile silyl ether or acid-labile arylalkyl ether. In some embodiments, $PG^4$ is trityl or substituted trityl. In some embodiments, $PG^4$ is trityl, monomethoxy trityl, or dimethoxy trityl. In some embodiments, $PG^4$ is trityl. In some embodiments, $PG^4$ taken with the oxygen atom to which it is bound is a silyl ether. In some embodiments, $PG^4$ taken with the oxygen atom to which it is bound is an acid-labile silyl ether. In some embodiments, $PG^4$ is triethylsilyl, t-butyldimethylsilyl, t-butyldiphenylsilyl, or triisopropylsilyl. In some embodiments, $PG^4$ is t-butyldimethylsilyl.

In some embodiments, $PG^2$ and $PG^3$ are taken together with the oxygen atoms to which they are bound to form a diol protecting group, such as a cyclic acetal or ketal. Such groups include methylene, ethylidene, benzylidene, isopropylidene, cyclohexylidene, and cyclopentylidene, a silylene derivative such as di-t-butylsilylene and a 1,1,3,3-tetraisopropyldisiloxanylidene derivative, a cyclic carbonate, and a cyclic boronate. In some embodiments, $PG^2$ and $PG^3$ are taken together with the oxygen atoms to which they are bound to form a cyclic ketal. In some embodiments, $PG^2$ and $PG^3$ are taken together with the oxygen atoms to which they are bound to form an acetonide, cyclohexylidene, or cyclopentylidene. In some embodiments, $PG^2$ and $PG^3$ are taken together with the oxygen atoms to which they are bound to form an acetonide.

At step S-4, the (N)-methanocarba nucleoside analogue A is deprotected to provide a compound of Formula I, I-A, or I-B. One of ordinary skill in the art will recognize that the conditions required to deprotect each of $PG^1$, $PG^2$, $PG^3$, and $PG^4$ may be the same or different. When more than one set of conditions is required to remove all four of $PG^1$, $PG^2$, $PG^3$, and $PG^4$ the deprotection steps may be carried out with, or without, isolation of intermediates where one or more, but not all, of $PG^1$, $PG^2$, $PG^3$, and $PG^4$ have been deprotected.

In certain embodiments, all four of $PG^1$, $PG^2$, $PG^3$, and $PG^4$ are removed by acid hydrolysis. It will be appreciated that upon acidic deprotection of compound A, a salt of Formula I, I-A, or I-B is formed. For example, when acidic deprotection of compound A is conducted with hydrochloric acid, then the compound of Formula I, I-A, or I-B would be formed as the hydrochloric acid salt. Similarly, when acidic deprotection of compound A is conducted with trifluoroacetic acid, then the compound of Formula I, I-A, or I-B would be formed as the trifluoroacetic acid salt. One of ordinary skill in the art would recognize that a wide variety of acids are useful for removing protecting groups that are acid-labile, and therefore a wide variety of salt forms of a compound of Formula I, I-A, or I-B are contemplated.

Furthermore, it will be appreciated that the free base of Formula I, I-A, or I-B may be obtained by treating the various salt forms of a compound of Formula I, I-A, or I-B with any of a wide variety of suitable bases. Suitable bases include metal carbonates, metal alkoxides, metal hydroxides, and basic resins. For example, in some embodiments, the base is sodium carbonate. In some embodiments, the base is sodium hydroxide. In some embodiments, the base is Amberlite resin.

According to one aspect, the present invention provides a method of preparing a compound of Formula I:

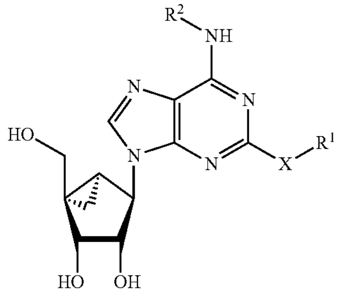

or a pharmaceutically acceptable salt thereof, wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; and n is 0, 1, 2, or 3;

comprising the steps of:

(a) providing a compound of Formula A:

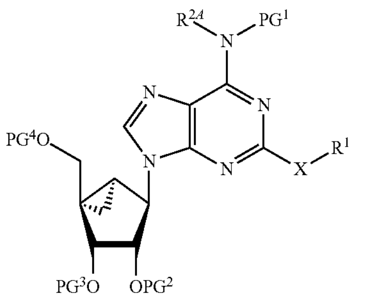

wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^{2A}$ is a suitable amino protecting group or $R^2$; or $R^{2A}$ and $PG^1$ are taken together to form a suitable bivalent nitrogen protecting group;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; or X is a covalent bond when $R^1$ is a halogen;

n is 0, 1, 2, or 3;

$PG^1$ is a suitable amino protecting group or is taken together with $R^{2A}$ to form a suitable bivalent nitrogen protecting group; and each of $PG^2$, $PG^3$, and $PG^4$ is independently a suitable hydroxyl protecting group; and (b) deprotecting said compound of Formula A to form said compound of Formula I.

In some embodiments, each of $R^1$, $R^2$, $R^3$, Ar, Cy, X, and n is as defined in the description of compounds of Formula I, above, and described in embodiments herein, both singly and in combination. In some embodiments, the compound of Formula I is a compound of Formula I-A, wherein each of $R^2$, $R^3$, X, and n is as defined in the description of compounds of Formula I-A, above, and described in embodiments herein, both singly and in combination. In some embodiments, the compound of Formula I is a compound of Formula I-B, wherein each of $R^1$, $R^2$, X, and n is as defined in the description of compounds of Formula I-B, above, and described in embodiments herein, both singly and in combination.

For example, in some embodiments, $R^1$ is $C_{1-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$. In some embodiments, $R^1$ is $C_{1-8}$ alkyl substituted with n instances of $R^3$. In some embodiments, $R^1$ is $C_{1-8}$ alkyl. In some embodiments, $R^1$ is methyl or ethyl. In some embodiments, $R^1$ is methyl. In some embodiments, $R^1$ is ethyl. In some embodiments, $R^1$ is halogen and X is a covalent bond.

In some embodiments, $R^2$ is hydrogen, $C_{1-4}$ alkyl, or $C_{3-5}$ cycloalkyl. In some embodiments, $R^2$ is hydrogen.

In some embodiments, X is S. In some embodiments, X is O. In some embodiments, X is a covalent bond and $R^1$ is halogen, such as F or Cl.

In some embodiments, n is 0.

In some embodiments, the compound of Formula I is

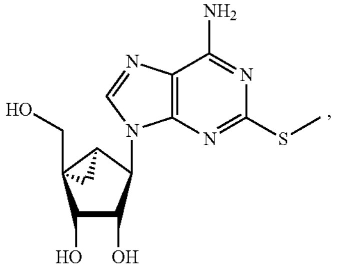

or a pharmaceutically acceptable salt thereof. In some embodiments, the compound of Formula I is

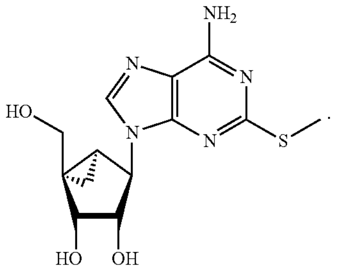

In some embodiments, the compound of Formula I is

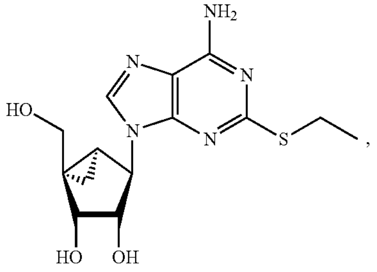

or a pharmaceutically acceptable salt thereof. In some embodiments, the compound of Formula I is

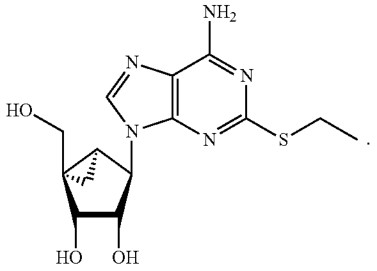

As defined generally above, $R^{2A}$ is a suitable amino protecting group or $R^2$; or $R^{2A}$ and $PG^1$ are taken together to form a suitable bivalent nitrogen protecting group.

In some embodiments, $R^{2A}$ is a suitable amino protecting group or $R^2$. In some embodiments, $R^{2A}$ is an acid-labile amino protecting group, hydrogen, $C_{1-4}$ alkyl, or $C_{3-5}$ cycloalkyl. In some embodiments, $R^{2A}$ is BOC or hydrogen.

In some embodiments, $R^{2A}$ is a suitable amino protecting group. In some embodiments, $R^{2A}$ is an acid-labile amino protecting group. In some embodiments, $R^{2A}$ taken with the —N($PG^1$)- moiety to which it is attached is an acid-labile carbamate. In some embodiments, $R^{2A}$ is BOC.

In some embodiments, $R^{2A}$ is $R^2$. In some embodiments, $R^{2A}$ is hydrogen, $C_{1-4}$ alkyl, or $C_{3-5}$ cycloalkyl. In some embodiments, $R^{2A}$ is hydrogen. In some embodiments, $R^{2A}$ is $C_{1-4}$ alkyl. In some embodiments, $R^{2A}$ is $C_{3-5}$ cycloalkyl.

In some embodiments, $R^{2A}$ and $PG^1$ are taken together to form a suitable bivalent nitrogen protecting group. In some embodiments, $R^{2A}$ and $PG^1$ are taken together with the nitrogen to which they are attached to form phthalimide. In some embodiments, $R^{2A}$ and $PG^1$ are taken together with the nitrogen to which they are attached to form tetramethylsuccinimide. In some embodiments, $PG^1$ and $R^{2A}$ are each BOC.

As defined generally above, $PG^1$ is a suitable amino protecting group or is taken together with $R^{2A}$ to form a suitable bivalent nitrogen protecting group. Suitable amino protecting groups, taken with the —N($R^{2A}$)— moiety to which it is attached, include, but are not limited to, aralkylamines, carbamates, allyl amines, amides, and the like. Examples of $PG^1$ groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like. In some embodiments, $PG^1$ is an acid-labile amino protecting group.

In some embodiments, $PG^1$ taken with the —N($R^{2A}$)— moiety to which it is attached is a carbamate. In some embodiments, $PG^1$ taken with the —N($R^{2A}$)— moiety to which it is attached is an acid-labile carbamate. In some embodiments, $PG^1$ is BOC.

As defined generally above, each of $PG^2$, $PG^3$, and $PG^4$ is independently a suitable hydroxyl protecting group. Suitable hydroxyl protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. In certain embodiments, each of $PG^2$, $PG^3$, and $PG^4$, taken with the oxygen atom to which it is bound, is independently selected from esters, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, or carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl) ethoxymethyl, and tetrahydropyranyl ethers. Examples of arylalkyl ethers include benzyl, p-methoxybenzyl (MPM), 3,4-dimethoxybenzyl, o-nitrobenzyl, p-nitrobenzyl, p-halobenzyl, 2,6-dichlorobenzyl, p-cyanobenzyl, trityl, 2- and 4-picolyl.

In some embodiments, each of $PG^2$, $PG^3$, and $PG^4$ is independently an acid-labile hydroxyl protecting group.

In some embodiments, $PG^2$ and $PG^3$ are taken together with the oxygen atoms to which they are bound to form a diol protecting group, such as a cyclic acetal or ketal. Such groups include methylene, ethylidene, benzylidene, isopropylidene, cyclohexylidene, and cyclopentylidene, a silylene derivative such as di-t-butylsilylene and a 1,1,3,3-tetraisopropyldisiloxanylidene derivative, a cyclic carbonate, and a cyclic boronate. In some embodiments, $PG^2$ and $PG^3$ are taken together with the oxygen atoms to which they are bound to form a cyclic ketal. In some embodiments, $PG^2$ and $PG^3$ are taken together with the oxygen atoms to which they are bound to form an acetonide, cyclohexylidene, or cyclopentylidene. In some embodiments, $PG^2$ and $PG^3$ are taken together with the oxygen atoms to which they are bound to form an acetonide.

In some embodiments, $PG^4$ taken with the oxygen atom to which it is bound is a silyl ether or arylalkyl ether. In some embodiments, $PG^4$ taken with the oxygen atom to which it is bound is an acid-labile silyl ether or acid-labile arylalkyl ether. In some embodiments, $PG^4$ is trityl or substituted trityl. In some embodiments, $PG^4$ is trityl, monomethoxy trityl, or dimethoxy trityl. In some embodiments, $PG^4$ is trityl. In some embodiments, $PG^4$ taken with the oxygen atom to which it is bound is a silyl ether. In some embodiments, $PG^4$ taken with the oxygen atom to which it is bound is an acid-labile silyl ether. In some embodiments, $PG^4$ is triethylsilyl, t-butyldimethylsilyl, t-butyldiphenylsilyl, or triisopropylsilyl. In some embodiments, $PG^4$ is t-butyldimethylsilyl.

One of ordinary skill in the art will recognize that the conditions required to deprotect each of $PG^1$, $PG^2$, $PG^3$, and $PG^4$ may be the same or different. When more than one set of conditions is required to remove all four of $PG^1$, $PG^2$, $PG^3$, and $PG^4$ the deprotection steps may be carried out with, or without, isolation of intermediates where one or more, but not all, of $PG^1$, $PG^2$, $PG^3$, and $PG^4$ have been deprotected.

In some embodiments, the deprotection at step (b) is achieved by treating said compound of Formula A with a suitable acid. Such suitable acids are well known in the art and include inorganic acids, e.g. hydrochloric acid, hydrobromic acid, phosphoric acid, nitric acid, sulfuric acid or perchloric acid, or organic acids, e.g. acetic acid, haloacetic acids, benzoic acids, alkyl sulfonic acids or aryl sulfonic acids. In some embodiments, the deprotection at step (b) is achieved by treating said compound of Formula A with hydrochloric acid. In some embodiments, the deprotection at step (b) is achieved by treating said compound of Formula A with trifluoroacetic acid.

It will be appreciated that upon acidic deprotection of the compound of Formula A, a salt of the compound of Formula I is formed. For example, when acidic deprotection of compound A is conducted with hydrochloric acid, then the compound of Formula I would be formed as the hydrochloric acid salt. Similarly, when acidic deprotection of compound A is conducted with trifluoroacetic acid, then the compound of Formula I would be formed as the trifluoroacetic acid salt. One of ordinary skill in the art would recognize that a wide variety of acids are useful for removing protecting groups that are acid-labile, and therefore a wide variety of salt forms of a compound of Formula I are contemplated.

In some embodiments, the deprotection at step (b) with a suitable acid is conducted in a suitable solvent. Examples of suitable solvents for use during deprotection step (b) include polar solvents such as alkyl alcohols, such as $C_1$ to $C_4$ alcohols (e.g. ethanol, methanol, 2-propanol), water, ethers (such as dioxane or tetrahydrofuran), and combinations thereof. In certain embodiments, the suitable solvent is a $C_1$ to $C_4$ alcohol (such as methanol, ethanol, or 2-propanol), water, or combinations thereof. In certain embodiments, the suitable solvent is methanol, water, or a combination thereof.

In some embodiments, the method further comprises the step of (c) treating a salt of the compound of Formula I with a suitable base to form the free-base compound of Formula I. Suitable bases include metal carbonates, metal alkoxides, metal hydroxides, and basic resins. For example, in some embodiments, the base is sodium carbonate. In some embodiments, the base is sodium hydroxide. In some embodiments, the base is an Amberlite resin. In some embodiments, the base is Amberlite resin-93.

In some embodiments, step (c) is conducted in a suitable solvent. Examples of solvents suitable for use during free base formation at step (c) include polar solvents such as alkyl alcohols, such as $C_1$ to $C_4$ alcohols (e.g. ethanol, methanol, 2-propanol), water, ethers (such as dioxane or tetrahydrofuran), and combinations thereof. In certain embodiments, the suitable solvent is a $C_1$ to $C_4$ alcohol (such as methanol, ethanol, or 2-propanol), water, or combinations thereof. In certain embodiments, the suitable solvent is methanol, water, or a combination thereof.

In another aspect, the present invention provides a method of preparing a compound of Formula A:

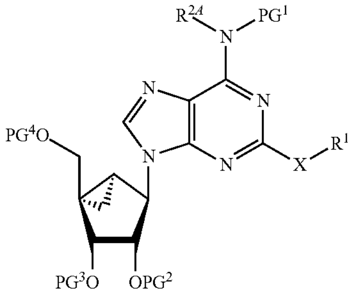

wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^{2A}$ is a suitable amino protecting group or $R^2$; or $R^{2A}$ and $PG^1$ are taken together to form a suitable bivalent nitrogen protecting group;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; or X is a covalent bond when $R^1$ is a halogen;

n is 0, 1, 2, or 3;

$PG^1$ is a suitable amino protecting group or is taken together with $R^{2A}$ to form a suitable bivalent nitrogen protecting group; and each of $PG^2$, $PG^3$, and $PG^4$ is independently a suitable hydroxyl protecting group;

comprising the steps of:

(a) providing a compound of Formula C:

C

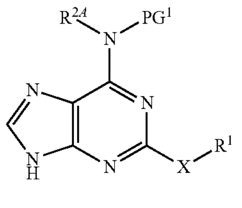

wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^{2A}$ is a suitable amino protecting group or $R^2$; or $R^{2A}$ and $PG^1$ are taken together to form a suitable bivalent nitrogen protecting group;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; or X is a covalent bond when $R^1$ is a halogen;

n is 0, 1, 2, or 3; and $PG^1$ is a suitable amino protecting group or is taken together with $R^{2A}$ to form a suitable bivalent nitrogen protecting group; and (b) coupling said compound of Formula C with a compound of Formula B:

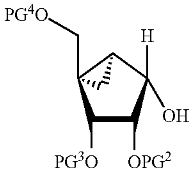

wherein each of $PG^2$, $PG^3$, and $PG^4$ is independently a suitable hydroxyl protecting group; to form said compound of Formula A.

In some embodiments, each of $R^1$, $R^2$, $R^3$, Ar, Cy, X, and n is as defined in the description of compounds of Formula I, above, and described in embodiments herein, both singly and in combination. In some embodiments, each of $R^2$, $R^3$, X, and n is as defined in the description of compounds of Formula I-A, above, and described in embodiments herein, both singly and in combination. In some embodiments, each of $R^1$, $R^2$, $R^3$, X, and n is as defined in the description of compounds of Formula I-B, above, and described in embodiments herein, both singly and in combination. In some embodiments, each of $R^1$, $R^2$, $R^{2A}$, $R^3$, $PG^1$, $PG^2$, $PG^3$, $PG^4$, Ar, Cy, X, and n is as defined in the description of methods of preparing compounds of Formula I, above, and described in embodiments herein, both singly and in combination.

Compounds of Formula B may be prepared according to strategies and procedures well known in the art, for example, as described in Choi, Y.; Moon, H. R.; Yoshimura, Y.; Marquez, V. E. "Recent advances in the synthesis of conformationally locked nucleosides and their success in probing the critical question of conformational preferences by their biological targets." *Nucleosides Nucleotides Nucleic Acids* 2003, Vol. 22, pp. 547-557; Michel B Y, Strazewski P "Total syntheses of a conformationally locked north-type methanocarba puromycin analogue and a dinucleotide derivative." Chem. Eur. J 2009, Vol. 15, pp. 6244-6257; and Tosh, D. K.; Padia, J.; Salvemini, D.; Jacobson, K. A. "Efficient, large-scale synthesis and preclinical studies of MRS5698, a highly selective $A_3$ adenosine receptor agonist that protects against chronic neuropathic pain." *Purinergic Signalling* 2015, Vol. 11, pp. 371-387; the entire contents of each of which are hereby incorporated by reference.

In some embodiments, the coupling at step (b) is achieved under Mitsunobu-type conditions. Various modifications of Mitsunobu conditions are well known in the art, for example, as described in "March's Advanced Organic Chemistry", $5^{th}$ Ed., Ed.: Smith, M. B. and March, J., John Wiley & Sons, New York: 2001; Downey, A. M. et al. "Direct One-Pot Synthesis of Nucleosides from Unprotected or 5-O-Monoprotected D-Ribose," *Org. Lett.* (2015) Vol. 17, pp. 4604-4607; and references therein; the entire contents of each of which are hereby incorporated by reference.

In some embodiments, the coupling at step (b) is achieved in the presence of a suitable phosphine and a suitable azodicarboxylate reagent. Such suitable phosphines are well known in the art and include aryl and alkyl phosphines. In some embodiments, the suitable phosphine is triphenyl phosphine or tributyl phosphine. In some embodiments, the suitable phosphine is triphenyl phosphine. Suitable azodicarboxylate reagents are well known in the art and include dialkyl azodicarboxylates that are unsubstituted (for example, diethyl, di-isopropyl, or di-t-butyl azodicarboxylate) or substituted (for example, di-2-methoxyethyl or di-p-nitrobenzyl azodicarboxylate). In some embodiments, the suitable azodicarboxylate is diethyl azodicarboxylate (DEAD) or di-isopropyl azodicarboxylate (DIAD). In some embodiments, the suitable azodicarboxylate is di-isopropyl azodicarboxylate.

In some embodiments, step (b) is conducted in a suitable solvent. Examples of suitable solvents include polar aprotic solvents such as ethers (such as tetrahydrofuran, dioxane, or methyl t-butyl ether), amide solvents (such as dimethylformamide or dimethylacetamide), and nitriles (such as acetonitrile). In some embodiments, the suitable solvent is an ether. In some embodiments, the suitable solvent is tetrahydrofuran.

In some embodiments, step (b) is conducted in the presence of a suitable base. Examples of suitable bases include organic bases (such as DBU), metal hydrides (such as sodium hydride), and metal carbonates (such as cesium or sodium carbonate).

In some embodiments, the compound of Formula A is provided substantially free of a compound of Formula F:

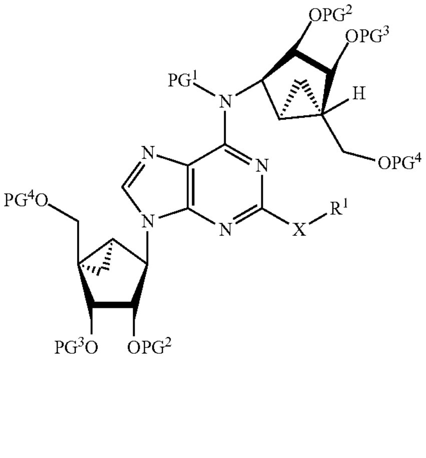

wherein each of $R^1$, $R^3$, $PG^1$, $PG^2$, $PG^3$, $PG^4$, Ar, Cy, X, and n is as defined in the description of methods of preparing compounds of Formula I, above, and described in embodiments herein, both singly and in combination. In some embodiments, the compound of Formula A is provided containing less than 0.05 molar equivalents of a compound of Formula F. In some embodiments, the compound of Formula A is provided containing less than 0.01 molar equivalents of a compound of Formula F. In some embodiments, the compound of Formula A is provided containing less than 0.005 molar equivalents of a compound of Formula F. In some embodiments, the compound of Formula A is provided containing less than 0.001 molar equivalents of a compound of Formula F. Compounds of Formula F may be detected in a sample of compound of Formula A using any appropriate analytical technique, for example, chromatography (such as high performance liquid chromatography, HPLC) with an appropriate detection method (such as ultraviolet absorption or mass spectrometry) or nuclear magnetic resonance spectroscopy.

In another aspect, the present invention provides a method of preparing a compound of Formula C:

C

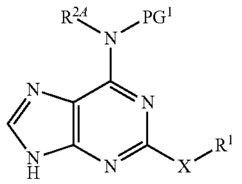

wherein:

- $R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;
- Ar is phenyl or a 5-6 membered monocyclic heteroaromatic ring having 1, 2, 3, or 4 heteroatoms independently selected from nitrogen, oxygen, and sulfur;
- Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;
- $R^{2A}$ is a suitable amino protecting group or $R^2$; or $R^{2A}$ and $PG^1$ are taken together to form a suitable bivalent nitrogen protecting group;
- $R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;
- each $R^3$ is independently deuterium, halogen, —CN, —O—($C_{1-4}$ alkyl), —OH, —S—($C_{1-4}$ alkyl), or —SH;
- X is S or O; or X is a covalent bond when $R^1$ is a halogen;
- n is 0, 1, 2, or 3; and
- $PG^1$ is a suitable amino protecting group or is taken together with $R^{2A}$ to form a suitable bivalent nitrogen protecting group;

comprising the steps of:

(a) providing a compound of Formula D:

D

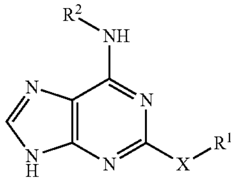

wherein:

- $R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;
- Ar is phenyl or a 5-6 membered monocyclic heteroaromatic ring having 1, 2, 3, or 4 heteroatoms independently selected from nitrogen, oxygen, and sulfur;
- Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;
- $R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;
- each $R^3$ is independently deuterium, halogen, —CN, —O—($C_{1-4}$ alkyl), —OH, —S—($C_{1-4}$ alkyl), or —SH;
- X is S or O; or X is a covalent bond when $R^1$ is a halogen; and
- n is 0, 1, 2, or 3;

and (b) protecting said compound of Formula D to form said compound of Formula C.

In some embodiments, each of $R^1$, $R^2$, $R^3$, Ar, Cy, X, and n is as defined in the description of compounds of Formula I, above, and described in embodiments herein, both singly and in combination. In some embodiments, each of $R^2$, $R^3$, X, and n is as defined in the description of compounds of Formula I-A, above, and described in embodiments herein, both singly and in combination. In some embodiments, each of $R^1$, $R^2$, $R^3$, X, and n is as defined in the description of compounds of Formula I-B, above, and described in embodiments herein, both singly and in combination. In some embodiments, each of $R^1$, $R^2$, $R^{2A}$, $R^3$, $PG^1$, Ar, Cy, X, and n is as defined in the description of methods of preparing compounds of Formula I, above, and described in embodiments herein, both singly and in combination.

In some embodiments, the protection at step (b) is achieved by treating said compound of Formula D with a suitable dicarbonate. Suitable dicarbonates are well known in the art, and afford compounds of Formula C, wherein $PG^1$ taken with the —N($R^{2A}$)— moiety to which it is attached is a carbamate. In some embodiments, the suitable dicarbonate afford compounds of Formula C, wherein $PG^1$ taken with the —N($R^{2A}$)— moiety to which it is attached is an acid-labile carbamate. In some embodiments, the suitable dicarbonate is $BOC_2O$.

In some embodiments, greater than 2.0 molar equivalents of suitable dicarbonate is used relative to the compound of Formula D. In some embodiments, greater than 3.0 molar equivalents of suitable dicarbonate is used relative to the compound of Formula D. In some embodiments, greater than 4.0 molar equivalents of suitable dicarbonate is used relative to the compound of Formula D. In some embodiments, about 4.0 molar equivalents of suitable dicarbonate is used relative to the compound of Formula D.

In some embodiments, step (b) is conducted in the presence of a suitable base. Examples of suitable bases are well known in the art, and include pyridine, substituted pyridines, and alkyl amines (such as triethylamine or di-isopropylethylamine). In some embodiments, the suitable base is pyridine or a substituted pyridine. In some embodiments, the suitable base in N,N-dimethylaminopyridine. In some embodiments, less than 1.0 molar equivalents of the suitable base is used relative to the compound of Formula D. In some embodiments, 0.1 to 0.3 molar equivalents of the suitable base is used relative to the compound of Formula D. In some embodiments, about 0.2 molar equivalents of the suitable base is used relative to the compound of Formula D. In some embodiments, greater than or equal to 1.0 molar equivalents of the suitable base is used relative to the compound of Formula D. In some embodiments, about 2.0 molar equivalents of the suitable base is used relative to the compound of Formula D, optionally wherein the suitable base is N,N-dimethylaminopyridine (DMAP).

In some embodiments, step (b) is conducted in a suitable solvent. Examples of suitable solvents are well known in the art and include polar aprotic solvents. In some embodiments, the suitable solvent is an ether, such as tetrahydrofuran or methyl t-butyl ether. In some embodiments, the suitable solvent is tetrahydrofuran.

In some embodiments, the product from treating said compound of Formula D with a suitable dicarbonate is isolated, and then further treated with a suitable base and a suitable solvent, to form said compound of Formula C.

In some embodiments, the suitable base is an aqueous basic solution. In some embodiments, the suitable base is an aqueous hydroxide, carbonate, or bicarbonate solution. In some embodiments, the suitable base is aqueous NaOH. In some embodiments, the suitable base is aqueous KOH. In some embodiments, the suitable base is aqueous $NH_4OH$. In some embodiments, the suitable base is aqueous $NaHCO_3$. In some embodiments, the suitable base is aqueous $KHCO_3$. In some embodiments, the suitable base is aqueous $Na_2CO_3$. In some embodiments, the suitable base is aqueous $K_2CO_3$.

In some embodiments, the suitable solvent includes polar solvents such as alkyl alcohols, such as $C_1$ to $C_4$ alcohols (e.g. ethanol, methanol, 2-propanol), water, ethers (such as dioxane or tetrahydrofuran), and combinations thereof. In some embodiments, the suitable solvent is a $C_1$ to $C_4$ alcohol (such as methanol, ethanol, 2-propanol), water, or combinations thereof. In some embodiments, the suitable solvent is methanol, water, or a combination thereof. In some embodiments, the suitable solvent is methanol. In some embodiments, the suitable solvent is tetrahydrofuran.

In some embodiments, the protection at step (b) is achieved by treating said compound of Formula D with a suitable reagent that forms a suitable bivalent nitrogen protecting group. Suitable reagents that form a suitable bivalent nitrogen protecting group are well known in the art, and afford compounds of Formula C, wherein $R^{2A}$ and $PG^1$ are taken together to form a suitable bivalent nitrogen protecting group. In some embodiments, the suitable reagent is a diacid anhydride. In some embodiments, the suitable reagent is phthalic anhydride. In some embodiments, the suitable reagent is phthaloyl chloride. In some embodiments, the suitable reagent is tetramethylsuccinic anhydride.

In another aspect, the present invention provides a method of preparing a compound of Formula D:

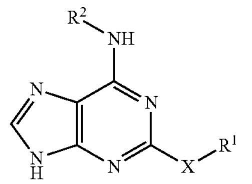

D wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; and n is 0, 1, 2, or 3;

comprising the steps of:

(a) providing a compound of Formula E:

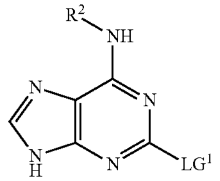

E wherein:

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms; and $LG^1$ is a suitable leaving group;

and (b) coupling said compound of Formula E to form said compound of Formula D.

In some embodiments, each of $R^1$, $R^2$, $R^3$, Ar, Cy, X, and n is as defined in the description of compounds of Formula I, above, and described in embodiments herein, both singly and in combination. In some embodiments, each of $R^2$, $R^3$, X, and n is as defined in the description of compounds of Formula I-A, above, and described in embodiments herein, both singly and in combination. In some embodiments, each of $R^1$, $R^2$, $R^3$, Ar, Cy, X, and n is as defined in the description of methods of preparing compounds of Formula I, above, and described in embodiments herein, both singly and in combination.

As defined generally above, $LG^1$ is a suitable leaving group. Suitable leaving groups are well known in the art, as described in, for example, "Organic Chemistry", Thomas Sorrell, University Science Books, Sausalito: 1999; "March's Advanced Organic Chemistry", $5^{th}$ Ed., Ed.: Smith, M. B. and March, J., John Wiley & Sons, New York: 2001; and "Comprehensive Organic Synthesis", $2^{nd}$ Ed., Ed.: Knochel, P. and Molander, G. A., Elsevier, Amsterdam: 2014. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyl (mesyl), tosyl, triflate, nitro-phenylsulfonyl (nosyl), and bromo-phenylsulfonyl (brosyl). In certain embodiments, $LG^1$ is chloro, fluoro, or triflate. In certain embodiments, $LG^1$ is chloro.

In some embodiments, the coupling at step (b) is achieved by treating said compound of Formula E with a thiol or alcohol of formula $R^1$—X—H. In some embodiments, the coupling is conducted in the presence of a suitable base. Suitable bases include metal carbonates, metal alkoxides, metal hydroxides, metal hydrides, and organic bases. For example, in some embodiments, the base is cesium carbonate. In some embodiments, the base is sodium carbonate. In some embodiments, the base is sodium hydroxide. In some embodiments, the base is sodium hydride.

In some embodiments, the coupling at step (b) is achieved by treating said compound of Formula E with a thiol or alcohol metal salt of formula $R^1$—X-M, wherein M is a metal atom. In some embodiments, M is sodium. In some embodiments, M is potassium.

In some embodiments, step (b) is conducted in a suitable solvent. Examples of suitable solvents include polar solvents such as amide solvents (such as dimethylformamide or dimethylacetamide), ethers (such as tetrahydrofuran, dioxane, or methyl t-butyl ether), and alcohols, such as $C_1$ to $C_4$ alcohols (e.g. ethanol, methanol, 2-propanol). In some embodiments, the suitable solvent is an amide solvent. In some embodiments, the suitable solvent is dimethylformamide.

Exemplary Synthetic Intermediates

As described above, the present invention provides intermediates useful in preparing a compound of Formula I and pharmaceutically acceptable salts thereof. In one aspect, the present invention provides a compound of Formula A:

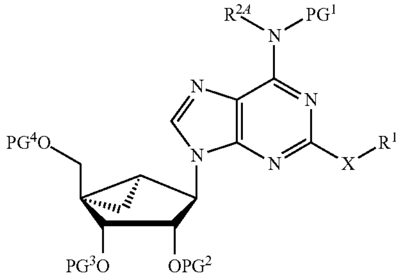

A wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^{2A}$ is a suitable amino protecting group or $R^2$; or $R^{2A}$ and $PG^1$ are taken together to form a suitable bivalent nitrogen protecting group;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; or X is a covalent bond when $R^1$ is a halogen;

n is 0, 1, 2, or 3;

$PG^1$ is a suitable amino protecting group or is taken together with $R^{2A}$ to form a suitable bivalent nitrogen protecting group; and each of $PG^2$, $PG^3$, and $PG^4$ is independently a suitable hydroxyl protecting group.

In some embodiments, each of $R^1$, $R^2$, $R^3$, Ar, Cy, X, and n is as defined in the description of compounds of Formula I, above, and described in embodiments herein, both singly and in combination. In some embodiments, each of $R^2$, $R^3$, X, and n is as defined in the description of compounds of Formula I-A, above, and described in embodiments herein, both singly and in combination. In some embodiments, each of $R^1$, $R^2$, $R^3$, X, and n is as defined in the description of compounds of Formula I-B, above, and described in embodiments herein, both singly and in combination. In some embodiments, each of $R^1$, $R^2$, $R^{2A}$, $R^3$, $PG^1$, $PG^2$, $PG^3$, $PG^4$, Ar, Cy, X, and n is as defined in the description of methods of preparing compounds of Formula I, above, and described in embodiments herein, both singly and in combination.

For example, in some embodiments, $R^1$ is $C_{1-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$. In some embodiments, $R^1$ is $C_{1-8}$ alkyl substituted with n instances of $R^3$. In some embodiments, $R^1$ is $C_{1-8}$ alkyl. In some embodiments, $R^1$ is methyl or ethyl. In some embodiments, $R^1$ is methyl. In some embodiments, $R^1$ is ethyl. In some embodiments, $R^1$ is halogen and X is a covalent bond.

In some embodiments, $R^2$ is hydrogen, $C_{1-4}$ alkyl, or $C_{3-5}$ cycloalkyl. In some embodiments, $R^2$ is hydrogen.

In some embodiments, X is S. In some embodiments, X is O. In some embodiments, X is a covalent bond and $R^1$ is a halogen, such as F or Cl.

In some embodiments, n is 0.

In some embodiments, $R^{2A}$ taken with the —N($PG^1$)-moiety to which it is attached is an acid-labile carbamate. In some embodiments, $R^{2A}$ is BOC. In some embodiments, $R^{2A}$ is $R^2$. In some embodiments, $R^{2A}$ is hydrogen.

In some embodiments, $PG^1$ taken with the —N($R^{2A}$)— moiety to which it is attached is an acid-labile carbamate. In some embodiments, $PG^1$ is BOC. In some embodiments, $PG^1$ and $R^{2A}$ are each BOC.

In some embodiments, $PG^2$ and $PG^3$ are taken together with the oxygen atoms to which they are bound to form a cyclic ketal. In some embodiments, $PG^2$ and $PG^3$ are taken together with the oxygen atoms to which they are bound to form an acetonide.

In some embodiments, $PG^4$ taken with the oxygen atom to which it is bound is a silyl ether or arylalkyl ether. In some embodiments, $PG^4$ is trityl or substituted trityl. In some embodiments, $PG^4$ is trityl.

In another aspect, the present invention provides a compound of Formula C:

C

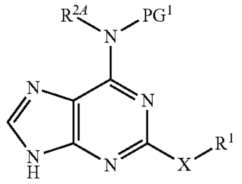

wherein:

- $R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;
- Ar is phenyl or a 5-6 membered monocyclic heteroaromatic ring having 1, 2, 3, or 4 heteroatoms independently selected from nitrogen, oxygen, and sulfur;
- Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;
- $R^{2A}$ is a suitable amino protecting group or $R^2$; or $R^{2A}$ and $PG^1$ are taken together to form a suitable bivalent nitrogen protecting group;
- $R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;
- each $R^3$ is independently deuterium, halogen, —CN, —O—($C_{1-4}$ alkyl), —OH, —S—($C_{1-4}$ alkyl), or —SH;
- X is S or O; or X is a covalent bond when $R^1$ is a halogen;
- n is 0, 1, 2, or 3; and
- $PG^1$ is a suitable amino protecting group or is taken together with $R^{2A}$ to form a suitable bivalent nitrogen protecting group.

In some embodiments, each of $R^1$, $R^2$, $R^3$, Ar, Cy, X, and n is as defined in the description of compounds of Formula I, above, and described in embodiments herein, both singly and in combination. In some embodiments, each of $R^2$, $R^3$, X, and n is as defined in the description of compounds of Formula I-A, above, and described in embodiments herein, both singly and in combination. In some embodiments, each of $R^1$, $R^2$, $R^{2A}$, $R^3$, $PG^1$, Ar, Cy, X, and n is as defined in the description of methods of preparing compounds of Formula I, above, and described in embodiments herein, both singly and in combination.

For example, in some embodiments, $R^1$ is $C_{1-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$. In some embodiments, $R^1$ is $C_{1-8}$ alkyl substituted with n instances of $R^3$. In some embodiments, $R^1$ is $C_{1-8}$ alkyl. In some embodiments, $R^1$ is $C_{3-8}$ alkyl. In some embodiments, $R^1$ is methyl or ethyl. In some embodiments, $R^1$ is methyl. In some embodiments, $R^1$ is ethyl.

In some embodiments, $R^2$ is hydrogen, $C_{1-4}$ alkyl, or $C_{3-5}$ cycloalkyl. In some embodiments, $R^2$ is hydrogen.

In some embodiments, X is S. In some embodiments, X is O.

In some embodiments, n is 0.

In some embodiments, $R^{2A}$ taken with the —N($PG^1$)- moiety to which it is attached is an acid-labile carbamate. In some embodiments, $R^{2A}$ is BOC. In some embodiments, $R^{2A}$ is $R^2$. In some embodiments, $R^{2A}$ is hydrogen.

In some embodiments, $PG^1$ taken with the —N($R^{2A}$)— moiety to which it is attached is an acid-labile carbamate. In some embodiments, $PG^1$ is BOC. In some embodiments, $PG^1$ and $R^{2A}$ are each BOC.

In another aspect, the present invention provides a compound of Formula D:

D

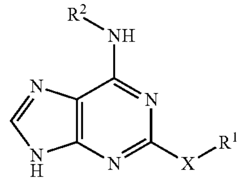

wherein:

- $R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$;
- Ar is phenyl or a 5-6 membered monocyclic heteroaromatic ring having 1, 2, 3, or 4 heteroatoms independently selected from nitrogen, oxygen, and sulfur;
- Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;
- $R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;
- each $R^3$ is independently deuterium, halogen, —CN, —O—($C_{1-4}$ alkyl), —OH, —S—($C_{1-4}$ alkyl), or —SH;
- X is S or O; and
- n is 0, 1, 2, or 3.

In some embodiments, each of $R^1$, $R^2$, $R^3$, Ar, Cy, X, and n is as defined in the description of compounds of Formula I, above, and described in embodiments herein, both singly and in combination. In some embodiments, each of $R^2$, $R^3$, X, and n is as defined in the description of compounds of Formula I-A, above, and described in embodiments herein, both singly and in combination. In some embodiments, each of $R^1$, $R^2$, $R^3$, Ar, Cy, X, and n is as defined in the description of methods of preparing compounds of Formula I, above, and described in embodiments herein, both singly and in combination.

For example, in some embodiments, $R^1$ is $C_{1-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$. In some embodiments, $R^1$ is $C_{1-8}$ alkyl substituted with n instances of $R^3$. In some embodiments, $R^1$ is $C_{1-8}$ alkyl. In some embodiments, $R^1$ is $C_{3-8}$ alkyl. In some embodiments, $R^1$ is methyl or ethyl. In some embodiments, $R^1$ is methyl. In some embodiments, $R^1$ is ethyl.

In some embodiments, $R^2$ is hydrogen, $C_{1-4}$ alkyl, or $C_{3-5}$ cycloalkyl. In some embodiments, $R^2$ is hydrogen.

In some embodiments, X is S. In some embodiments, X is O.

In some embodiments, n is 0.

Exemplary Methods of Treatment

In some embodiments, the present invention provides a method of inhibiting or preventing the accumulation of cAMP in a patient comprising administering to said patient a compound described herein, or a pharmaceutically acceptable salt thereof or composition comprising the same.

In some embodiments, the present invention provides a method of treating an injury, disease, or condition selected from traumatic brain injury (TBI), concussion, stroke, partial or total spinal cord transection, malnutrition, toxic neuropathies, meningoencephalopathies, neurodegeneration caused by a genetic disorder, age-related neurodegeneration, vascular disease, Alzheimer's Disease (AD), Parkinson's Disease (PD), Huntington's Disease (HD), Multiple Sclerosis (MS), amyotrophic lateral sclerosis (ALS), chronic traumatic encephalopathy (CTE), cardiovascular disease, autoimmune diseases, allergic diseases, transplant rejection, graft-versus-host disease, intraocular hypertension, glaucoma, odor sensitivity, an olfactory disorder, type 2 diabetes and/or pain control, respiratory diseases, deficits in CNS function, deficits in learning, deficits in cognition, otic disorders, Meniere's disease, endolymphatic hydrops, progressive hearing loss, dizziness, vertigo, tinnitus, collateral brain damage associated with radiation cancer therapy, migraine treatment, sleep disorders in the elderly, epilepsy, schizophrenia, symptoms experienced by recovering alcoholics, damage to neurons or nerves of the peripheral nervous system during surgery, gastrointestinal conditions, pain mediated by the CNS, migraine, collateral brain damage associated with radiation cancer therapy, depression, mood or behavioral changes, dementia, erratic behavior, suicidality, tremors, Huntington's chorea, loss of coordination of movement, deafness, impaired speech, dry eyes, hypomimia, attention deficit, memory loss, cognitive difficulties, vertigo, dysarthria, dysphagia, ocular abnormalities or disorientation, or addiction; comprising administering to a patient a compound described herein, or a pharmaceutically acceptable salt thereof or a composition comprising the same. In some embodiments, the present invention provides a method of treating an injury, disease, or condition selected from traumatic brain injury (TBI), stroke, a neurodegenerative condition, or a heart or cardiovascular disease, comprising administering to a patient in need thereof an effective amount of a compound described herein, or a pharmaceutically acceptable salt thereof or composition comprising the same.

In some embodiments, the compound acts as an agonist of an $A_3$ adenosine receptor ($A_3R$). In some embodiments, the compound is a partial agonist. In some embodiments, the compound is a biased agonist. In some embodiments, the compound acts by dual agonism at an $A_3$ adenosine receptor and an $A_1$ adenosine receptor ($A_1R$). In some embodiments, the compound acts as an agonist of an $A_1$ adenosine receptor ($A_1R$). In some embodiments, the compound is a partial agonist. In some embodiments, the compound is a biased agonist.

In some embodiments, the present invention provides a method of treating an injury, disease, or condition selected from traumatic brain injury (TBI), stroke, a neurodegenerative condition, or a heart or cardiovascular disease, comprising administering to a patient in need thereof an effective amount of compound described herein, or a pharmaceutically acceptable salt thereof or composition comprising the same.

In some embodiments, the present invention provides a method of treating a brain or central nervous system (CNS) injury or condition selected from traumatic brain injury (TBI) or stroke, comprising administering to a patient in need thereof an effective amount of a compound described herein, or a pharmaceutically acceptable salt thereof or composition comprising the same.

In some embodiments, the present invention provides a method of treating or ameliorating a traumatic brain injury (TBI), radiation damage, stroke, migraine headache, a heart or cardiovascular disease, or neurodegenerative disorder, comprising administering to a patient in need thereof an effective amount of a compound described herein, or a pharmaceutically acceptable salt thereof or composition comprising the same.

In some embodiments, the present invention provides a method of treating or ameliorating a traumatic brain injury (TBI), radiation damage, stroke, migraine headache, a heart or cardiovascular disease, or neurodegenerative disorder, comprising administering to a patient in need thereof an effective amount of a compound described herein, or a pharmaceutically acceptable salt thereof or composition comprising the same.

In some embodiments, the present invention provides a method of treating an injury, disease, or condition selected from traumatic brain injury (TBI), stroke, a neurodegenerative condition, or a heart or cardiovascular disease comprising administering to a patient in need thereof an effective amount of a compound described herein, or a pharmaceutically acceptable salt thereof or composition comprising the same.

In some embodiments, the injury, disease, or condition is TBI.

In some embodiments, the TBI is selected from concussion, blast injury, combat-related injury, or a mild, moderate or severe blow to the head.

In some embodiments, the injury, disease, or condition is a stroke selected from ischemic stroke, hemorrhagic stroke, subarachnoid hemorrhage, cerebral vasospasm, or transient ischemic attacks (TIA).

In some embodiments, neuroprotection or neurorestoration is increased in the patient as compared with an untreated patient.

In some embodiments, the neurodegenerative disease is selected from Alzheimer's Disease (AD), Parkinson's Disease (PD), Huntington's Disease (HD), Multiple Sclerosis (MS), amyotrophic lateral sclerosis (ALS), chronic traumatic encephalopathy (CTE), or a neurodegenerative condition caused by a virus, alcoholism, tumor, toxin, or repetitive brain injuries.

In some embodiments, the neurodegenerative disease is Parkinson's Disease.

In some embodiments, the injury, disease, or condition is Alzheimer's Disease, migraine, brain surgery, or a neurological side effect associated with cancer chemotherapy.

In some embodiments, the recovery period after the TBI, stroke, cardiac ischemia, or myocardial infarction is decreased as compared with an untreated patient.

In some embodiments, the heart or cardiovascular disease is selected from cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis.

In some embodiments, the heart or cardiovascular disease is cardiac ischemia or myocardial infarction.

In some embodiments, the compound or composition is administered chronically to treat stroke, cardiac ischemia, or myocardial infarction during the time period after the injury has occurred as it resolves.

In some embodiments, the present invention provides a method of increasing neuroprotection or neurorestoration in a patient in need thereof who has suffered a TBI or stroke, comprising administering to the patient an effective amount of a compound described herein, or a pharmaceutically acceptable salt thereof or composition comprising the same.

In some embodiments, the compound or pharmaceutically acceptable salt thereof is administered orally, intravenously, or parenterally.

In some embodiments, the compound or composition is administered within 24 hours of the TBI or stroke.

In some embodiments, the compound or composition is administered within 8 hours of the TBI or stroke.

In some embodiments, the compound or composition is administered at least during the first 8-48 hours following the TBI or stroke.

In some embodiments, the present invention provides a method of treating a heart or cardiovascular disease comprising administering to a patient in need thereof an effective amount of a compound described herein, or a pharmaceutically acceptable salt thereof or composition comprising the same.

In some embodiments, the patient has suffered a cardiac ischemia or myocardial infarction.

In some embodiments, the compound or composition increases cardioprotection or regeneration of damaged heart tissue in the patient.

In some embodiments, the compound or composition decreases the recovery period after the cardiac ischemia or myocardial infarction in the patient as compared with an untreated patient.

In some embodiments, the present invention provides a method of treating an injury, disease, disorder, or condition selected from:

(i) brain damage caused by radiation or collateral brain damage associated with radiation cancer therapy or migraine treatment;
(ii) migraine headache;
(iii) a condition associated with a brain injury or a neurodegenerative condition; or
(iv) an autoimmune disease or condition, glaucoma, an otic disorder, progressive hearing loss, tinnitus, epilepsy, or pain (e.g., pain mediated by the CNS, neuropathic pain, inflammatory pain, or acute pain);

comprising administering to a patient in need thereof an effective amount of a compound described herein, or a pharmaceutically acceptable salt thereof or composition comprising the same.

In some embodiments, the compound or composition increases neuroprotection or neurorestoration in the patient as compared with an untreated patient.

In some embodiments, the condition associated with a brain injury or a neurodegenerative condition is selected from epilepsy, migraine, collateral brain damage associated with radiation cancer therapy, depression, mood or behavioral changes, dementia, erratic behavior, suicidality, tremors, Huntington's chorea, loss of coordination of movement, deafness, impaired speech, dry eyes, hypomimia, attention deficit, memory loss, cognitive difficulties or deficit in cognition, deficit in CNS function, deficit in learning, vertigo, dysarthria, dysphagia, ocular abnormalities, or disorientation.

In some embodiments, the present invention provides a method of increasing cardioprotection or regeneration of damaged heart tissue in a patient in need thereof who has suffered a cardiac ischemia or myocardial infarction, comprising administering to the patient an effective amount of a compound described herein, or a pharmaceutically acceptable salt thereof or composition comprising the same.

It has been surprisingly found that certain purine nucleoside mono-, di-, and tri-phosphates, such as phosphates of nucleosides disclosed herein, are dephosphorylated in vivo and exist primarily as the nucleoside, i.e., they are not substantially phosphorylated in vivo. Without wishing to be bound by theory, it is believed that such dephosphorylation is effected by ectonucleotidases, enzymes responsible for the dephosphorylation of nucleotides that are present both on the surface of cell membranes and circulating in blood and plasma (See Ziganshin et al. Pflugers Arch. (1995) 429:412-418). It is often extremely difficult to predict which nucleotide analogs will be substrates for ectonucleotidases and will thus be expected to be dephosphorylated in vivo. In some embodiments, the dephosphorylated compound is responsible for the therapeutic efficacy. Thus, in some embodiments the corresponding, phosphorylated mono-, di-, or tri-phosphate, or a phosphate ester such as an alkyl or phenyl ester thereof, is a prodrug or precursor to the agent responsible for the therapeutic effect.

In some embodiments, compounds of the present invention are able to cross the blood-brain barrier (BBB). The term "blood-brain barrier" or "BBB", as used herein, refers to the BBB proper as well as to the blood-spinal barrier. The blood-brain barrier, which consists of the endothelium of the brain vessels, the basal membrane and neuroglial cells, acts to limit penetration of substances into the brain. In some embodiments, the brain/plasma ratio of total drug is at least approximately 0.01 after administration (e.g. oral or intravenous administration) to a patient. In some embodiments, the brain/plasma ratio of total drug is at least approximately 0.03. In some embodiments, the brain/plasma ratio of total drug is at least approximately 0.06. In some embodiments, the brain/plasma ratio of total drug is at least approximately 0.1. In some embodiments, the brain/plasma ratio of total drug is at least approximately 0.2.

Prototypical adenosine $A_3$ agonists such as Cl-IB-IMECA and MRS5698 are low-solubility, lipophilic compounds with cLogP values typically >2. This lipophilicity is a major factor contributing to these compounds' high plasma protein binding, high brain binding and resulting low free fraction of drug available to interact with the $A_3$ receptor in the brain. In some embodiments, for example neurological and neurodegenerative conditions, the physicochemical properties of compounds of the present invention are substantially different; these and related compounds are hydrophilic compounds with cLogP<0, resulting in high solubility, low plasma and brain binding and high unbound drug concentrations available to interact with the $A_3$ receptor.

Accordingly, in some embodiments the compound has a cLogP less than about 0.8, about 0.7, about 0.6, about 0.5, about 0.4, about 0.3, about 0.2, about 0.1, about 0.05, about 0.01, or about 0.005. In some embodiments, the compound has a cLogP less than about 0, such as less than about −0.1, −0.2, −0.3, −0.4, −0.5, −0.6, −0.7, −0.8, or −0.9 or less. In some embodiments, the compound has an unbound fraction in plasma of about 0.5 to 0.9. In some embodiments, the compound has an unbound fraction in plasma of about 0.6 to 0.85, 0.7 to 0.8, or about 0.75. In some embodiments, the compound has an unbound fraction in brain of at least about 0.02, or at least about 0.03, 0.04, 0.05, 0.06, 0.07, 0.08, 0.09, 0.1, 0.12, 0.15, or 0.17 or greater. In some embodiments, the compound has an unbound fraction in plasma of about 0.6 to 0.85, 0.7 to 0.8, or about 0.75 and/or at least 0.08 unbound fraction in brain.

Uses of Compounds and Pharmaceutically Acceptable Compositions Thereof

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent, delay or lessen the severity of their recurrence.

Brain, CNS, Cardiovascular, and Other Injuries and Conditions

In some embodiments, the present invention provides a new approach to preventing and/or treating brain damage associated with acute brain trauma as well as longer term diseases of the brain and CNS and heart and cardiovascular diseases and conditions. In one aspect, the present invention provides methods of treating such injuries, diseases, and conditions by utilizing neuroprotective and neurorestorative effects mediated by astrocytes, which are now understood as the key natural caretaker cell of neurons, as well as the astrocyte mitochondria, which supply a significant portion of the brain's energy. In another aspect, the present invention provides methods of treating such injuries, diseases, and conditions by cardioprotective and regenerative effects mediated by $A_3R$ receptors. Regarding neuroprotective and neurorestorative effects, without wishing to be bound by theory, it is believed that selective enhancement of astrocyte energy metabolism mediated by $A_3R$ and/or $P2Y_1$ receptors promotes astrocyte caretaker functions, such as their neuroprotective and neurorestorative functions, in turn enhancing the resistance of neurons and other cells to both acute injury and long term stress. In some cases, it may be advantageous to achieve biased, i.e., selective or preferential, of one or more pathways mediated by $A_3R$ and/or $P2Y_1$ and/or $A_1R$ receptors wherein one or more undesired pathways are not activated, or activated to a lesser degree. In addition to or as an alternative to astrocytes, neuroprotective or neurorestorative function of glia, microglia, neurons, endothelium cells and other brain and/or CNS cell types may be activated. Accordingly, in one aspect, the present invention provides compounds and methods of use thereof for treating, ameliorating, or promoting recovery from certain conditions of the brain or central nervous system (CNS) such as brain injuries, for example by increasing neuroprotection and/or neurorestorative effects mediated by astrocytes, glia, microglia, neurons, endothelium cells or other cells of the brain and/or CNS, comprising administering to a patient in need thereof an effective amount of a compound described herein, or a pharmaceutically acceptable salt thereof or composition comprising the same.

Astrocytes play key roles in supporting and protecting neurons and they critically affect the outcome of brain injuries that cause brain damage, such as ischemic injuries. The central role astrocyte mitochondria themselves play in these brain functions is less well appreciated. For example, inhibition of astrocyte mitochondria increases swelling and leads to necrotic cell death. Neurons are permanently injured by recurrent spreading depolarizations only if astrocyte mitochondrial function fails, and astrocyte mitochondria are required for reduction of pathophysiological elevations of extracellular $K^+$, which initiate spreading depolarizations. Activation of purinergic receptors on astrocytes results in increased mitochondrial $Ca^{2+}$ that enhances mitochondrial citric acid cycle function and increases respiration and ATP production. Accordingly, in one aspect, the present invention relates to the discovery that activation of astrocyte purinergic receptors enhances brain cell survival signalling pathways, enabling both astrocyte and neuronal viability during oxidative stress. Furthermore, activated astrocytes generate and supply reduced glutathione, a key antioxidant that aids in the resistance of both astrocytes and neurons to oxidative stress. Thus, in one aspect, the present invention provides a method of modulating astrocyte purinergic receptors to promote survival and viability of one or more cell types in the brain of a patient after oxidative stress, such as oxidative stress caused by a brain injury, ischemia-reperfusion or a neurodegenerative condition, comprising administering to a patient in need thereof a compound described herein, or a pharmaceutically acceptable salt thereof or composition comprising the same.

In some embodiments, activation of astrocytes is achieved through contacting with a disclosed compound one or more purinergic receptors such as adenosine receptors (ARs), for example those associated with or expressed by astrocytes, thus modulating the activity of the one or more receptors. In some embodiments, through effects on adenosine receptors such as $A_1$, $A_{2A}$, $A_{2B}$ and $A_3$ on astrocytes, the compound activates astrocytes to treat one or more disclosed diseases or conditions. In some embodiments, after administration to a patient in need thereof, a disclosed compound influences one or more astrocyte functions. In some embodiments, the astrocyte function is selected from glutamate uptake, reactive gliosis, swelling, or release of neurotrophic and neurotoxic factors that act to ameliorate metabolic stress and its consequences. In some embodiments, the compound is an AR agonist. In some embodiments, the purinergic receptor is an $A_3$ adenosine receptor ($A_3R$). In some embodiments, the compound is an $A_3R$ agonist. In some embodiments, the compound is a partial agonist or biased agonist or biased partial agonist, at an $A_3$ receptor ($A_3R$), such as a human $A_3$ receptor ($hA_3R$). In some embodiments, the compound acts as an agonist of an $A_1$ adenosine receptor ($A_1R$). In some embodiments, the compound is a biased agonist at an $A_1$ and/or $A_3$ receptor. In some embodiments, the compound acts by dual agonism at an $A_3R$ and an $A_1R$.

P2Y receptors are G-protein-coupled receptors and different subtypes of these receptors have important roles in processes such as synaptic communication, cellular differentiation, ion flux, vasodilation, blood brain barrier permeability, platelet aggregation and neuromodulation. Characterized members of the purinergic P2Y receptor family include the mammalian $P2Y_1$, $P2Y_{11}$, $P2Y_{12}$ and $P2Y_{13}$ receptors, which bind to adenine nucleotides; the $P2Y_4$, $P2Y_6$, and $P2Y_{14}$ receptors, that bind to uracil nucleotides; and the $P2Y_2$ and rodent $P2Y_4$ receptors, which have mixed selectivity. In some embodiments, activation of astrocytes is achieved through contacting with a disclosed compound one or more purinergic receptors such as P2Y receptors, for example those associated with or expressed by astrocytes, thus modulating the activity of the one or more receptors. In some embodiments, through effects on P2Y receptors such as $P2Y_1$, $P2Y_{11}$, $P2Y_{12}$ and $P2Y_{13}$ receptors associated with or expressed by astrocytes, the compound activates astrocytes to treat one or more disclosed diseases or conditions. In some embodiments, the P2Y receptor is a $P2Y_1$ receptor. In some embodiments, the $P2Y_1$ receptor is located on intracellular mitochondrial membranes. In some embodiments, the compound is a P2Y agonist. In some embodiments, the compound is a $P2Y_1$ agonist, e.g. at a human $P2Y_1$ receptor. In some embodiments, the compound is a biased agonist, partial agonist, or biased partial agonist at a $P2Y_1$ receptor, such as a human $P2Y_1$ receptor. In some embodiments, the compound is a biased antagonist at a $P2Y_1$ receptor.

In another aspect, the present invention provides a method of treating or ameliorating a brain injury, disease, or condition, such as a brain injury resulting from a TBI or progressive neurodegenerative disorder, in a patient in need thereof, comprising administering to the patient an effective amount of a compound described herein, or a pharmaceutically acceptable salt thereof or composition comprising the same. In some embodiments, the subject has suffered a TBI, concussion, stroke, partial or total spinal cord transection, or malnutrition. In other embodiments, the subject has suffered toxic neuropathies, meningoencephalopathies, neurodegeneration caused by a genetic disorder, age-related neurodegeneration, or a vascular disease; or another disease disclosed in U.S. Pat. No. 8,691,775, which is hereby incorporated by reference. In some embodiments, the present invention provides a method of treating or ameliorating a brain injury, disease, or condition, such as a brain injury resulting from a TBI or progressive neurodegenerative disorder, in a patient in need thereof, comprising administering to the patient an effective amount of a compound described herein, or a pharmaceutically acceptable salt thereof or composition comprising the same, wherein the compound is an $A_3R$ agonist. In other embodiments, the present invention provides a method of treating or ameliorating a brain injury, disease, or condition, such as a brain injury resulting from a TBI or progressive neurodegenerative disorder, in a patient in need thereof, comprising administering to the patient an effective amount of a compound described herein, or a pharmaceutically acceptable salt thereof or composition comprising the same, wherein the compound is a $P2Y_1$ agonist. In other embodiments, the present invention provides a method of treating or ameliorating a brain injury, disease, or condition, such as a brain injury resulting from a TBI or progressive neurodegenerative disorder, in a patient in need thereof, comprising administering to the patient an effective amount of a compound described herein, or a pharmaceutically acceptable salt thereof or composition comprising the same, wherein the compound is an $A_1$ agonist. In some embodiments, the compound is a biased agonist, partial agonist, or biased partial agonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is one of those depicted in Table 1, or a pharmaceutically acceptable composition comprising the same.

In another aspect, the present invention provides a method of promoting or increasing neuroprotection, neurorestoration, or neuroregeneration in a patient suffering from a disease or condition, comprising administering to the patient an effective amount of a compound described herein, or a pharmaceutically acceptable salt thereof or composition comprising the same. In some embodiments, the patient is suffering from a neurodegenerative disease or condition. In some embodiments, the patient has suffered a TBI.

In another aspect, the present invention provides a method of promoting astrocyte-mediated neuroprotection or neurorestoration in a patient in need thereof, comprising administering to the patient an effective amount of a disclosed compound. In some embodiments, the present invention provides a method of promoting astrocyte-mediated neuroprotection or neurorestoration in a patient in need thereof, comprising administering to the patient an effective amount of a compound described herein, or a pharmaceutically acceptable salt thereof or composition comprising the same, wherein the compound is an $A_3R$ agonist. In some embodiments, the present invention provides a method of promoting astrocyte-mediated neuroprotection or neurorestoration in a patient in need thereof, comprising administering to the patient an effective amount of a compound described herein, or a pharmaceutically acceptable salt thereof or composition comprising the same, wherein the compound is an $A_1R$ agonist. In other embodiments, the present invention provides a method of promoting astrocyte-mediated neuroprotection or neurorestoration in a patient in need thereof, comprising administering to the patient an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is one of those described in Table 1, or a pharmaceutically acceptable salt thereof or composition comprising the same.

In another aspect, the present invention provides a method of promoting survival of neurons, glial cells, endothelial cells or other brain cells, such as those in an ischemic penumbra in a patient in need thereof, comprising administering to the patient an effective amount of a compound described herein, or a pharmaceutically acceptable salt thereof or composition comprising the same. In some embodiments, the present invention provides a method of promoting survival of neurons, glial cells, or other brain cells, such as those in an ischemic penumbra in a patient in need thereof, comprising administering to the patient an effective amount of a compound described herein, or a pharmaceutically acceptable salt thereof or composition comprising the same, wherein the compound is an $A_3R$ agonist. In some embodiments, the present invention provides a method of promoting survival of neurons, glial cells, or other brain cells, such as those in an ischemic penumbra in a patient in need thereof, comprising administering to the patient an effective amount of a compound described herein, or a pharmaceutically acceptable salt thereof or composition comprising the same, wherein the compound is an $A_1R$ agonist. In some embodiments, the present invention provides a method of promoting survival of neurons, glial cells, endothelial cells or other brain cells, such as those in an ischemic penumbra in a patient in need thereof, comprising administering to the patient an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is one of those described in Table 1, or a pharmaceutically acceptable salt thereof or composition comprising the same.

In further embodiments, the patient has or is at risk of acquiring a brain injury such as those below. Accordingly, methods of treating the conditions discussed below are also provided.

Traumatic Brain Injuries

Traumatic brain injuries (TBI) are a distressingly common medical condition and are predicted to become the third major cause of global morbidity and mortality by 2020. There are no approved treatments for TBI, and most TBI patients are discharged from the hospital with no pharmacological treatment (Witt 2006). Repetitive TBI such as concussions can trigger age-associated neurodegeneration that results in a range of symptoms and disabilities over decades (McKee 2013). TBIs can happen through sports-related injuries, motor vehicle accidents, falls, explosive impacts, physical assaults, etc. Injuries range widely in their complexity and severity, from “mild” concussions with brief alterations in mental status, cognitive difficulties, or loss of consciousness to “severe” with prolonged periods of unconsciousness and/or amnesia after the injury. In the U.S., approximately 1.7 million people have an injury resulting in a TBI annually and seek medical intervention (USCSF and CDC), and the CDC estimates that 1.6 to 3.8 million additional concussion incidents occur in sports and other recreational pursuits annually that do not present to hospital or emergency departments. (CDC; Langlois 2006) Approximately 5-10% of athletes will receive a concussion each sport season. (Sports Concussion Institute 2012) Football is the sport with the highest concussion risk for males (75% chance for concussion), while soccer has the highest concussion risk for females (50% chance for concussion). TBI is the leading cause of death and disability in children and young adults (CDC) and the most commonly received military-related injury; approximately 20% of U.S. Service Members deployed since 2003 have sustained at least one TBI. (Chronic Effects of Neurotrauma Consortium (CENC); Warden 2006; Scholten 2012; Taylor 2012; Gavett 2011; Guskiewicz 2005; Omalu 2005) Total TBI-related indirect and direct medical costs are estimated at $77 billion annually (UCSF and CDC). At least 5 million Americans require ongoing daily support in performing activities as a result of TBI (CDC and Thurman 1999).

Activation of astrocytes according to the present invention represents a new treatment option for such conditions. Accordingly, provided herein in one aspect is a method of treating TBI or promoting recovery from TBI, comprising administering to a patient in need thereof an effective amount of a compound described herein, or a pharmaceutically acceptable salt thereof or composition comprising the same. In some embodiments, the TBI is selected from traumatic injuries to the brain (such as concussion, blast injury, combat-related injury) or spinal cord (such as partial or total spinal cord transection). In some embodiments, the TBI results from a mild, moderate, or severe blow to the head, comprises an open or closed head wound, or results from a penetrating or non-penetrating blow to the head. In some embodiments, the present invention provides a method of treating TBI or promoting recovery from TBI, comprising administering to a patient in need thereof an effective amount of a compound described herein, or a pharmaceutically acceptable salt thereof or composition comprising the same, wherein the compound is an $A_3R$ agonist. In some embodiments, the present invention provides a method of treating TBI or promoting recovery from TBI, comprising administering to a patient in need thereof an effective amount of a compound described herein, or a pharmaceutically acceptable salt thereof or composition comprising the same, wherein the compound is an $A_1R$ agonist. In some embodiments, the present invention provides a method of treating TBI or promoting recovery from TBI, comprising administering to a patient in need thereof an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is one of those described in Table 1, or a pharmaceutically acceptable composition comprising the same.

Stroke

A stroke occurs when a blood vessel that transports oxygen and nutrients to the brain is disrupted due to an ischemic blockage or from the hemorrhagic rupture of a blood vessel in the brain, causing neurons, glia and endothelial cells in the disrupted region of the brain to die. The outcome of the stroke depends upon the location and breadth of damage, and the impacts of that damage are observed in the body functions regulated by the damaged brain region. Strokes can cause unilateral or bilateral paralysis, speech and language disabilities, memory loss, behavioural changes, and even death. Stroke is the fourth leading cause of death in the United States and is a major cause of adult disability. Each year, ~800,000 people experience a new or recurrent stroke. Each day, over 2000 Americans will have a stroke, resulting in death in over 400 of these incidents. Stroke accounted for ~1 of every 19 deaths in the United States in 2010. An estimated 6.8 million Americans ≥20 years of age have had a stroke. (AHA and Go 2014) As of 2010, the annual direct and indirect cost of stroke was estimated at $36.5 billion. Within minutes of a stroke, the lack of blood flow will permanently damage a core of brain tissue. Between this damaged core and normal brain tissue is a region of tissue known as the penumbra—tissue that is under gradated stress from lessened blood flow and some disruption of energy metabolism. Over the first 24-48 hours following a stroke incident, the stress on neuronal and glia cells in the penumbra resolves either with some recovery or further cell death.

In one aspect, the present invention provides a method of neuroprotective therapy in a stroke patient, comprising administering to a patient in need thereof an effective amount of a compound described herein, or a pharmaceutically acceptable salt thereof or composition comprising the same. In some embodiments, such therapy salvages as much of the penumbra as possible, and/or limits further acute tissue damage, and/or promotes neuron recovery. In another aspect is provided a method of treating stroke or promoting recovery from stroke, comprising administering to a patient in need thereof an effective amount of a compound described herein, or a pharmaceutically acceptable salt thereof or composition comprising the same. In another aspect is provided a method of promoting or increasing neuroprotection, neuroregeneration, or neurorestoration in a patient who has suffered a stroke, comprising administering to the patient an effective amount of a compound described herein, or a pharmaceutically acceptable salt thereof or composition comprising the same. In another aspect is provided a method of treating stroke or promoting recovery from stroke, comprising administering to a patient in need thereof an effective amount of a compound described herein, or a pharmaceutically acceptable salt thereof or composition comprising the same, wherein the compound is an $A_3R$ agonist. In another aspect is provided a method of treating stroke or promoting recovery from stroke, comprising administering to a patient in need thereof an effective amount of a compound described herein, or a pharmaceutically acceptable salt thereof or composition comprising the same, wherein the compound is an $A_1R$ agonist. In some embodiments, the present invention provides a method of treating stroke or promoting recovery from stroke, comprising administering to a patient in need thereof an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is one of those described in Table 1, or a pharmaceutically acceptable salt thereof or composition comprising the same.

In some embodiments, the stroke is selected from selected from ischemic stroke, hemorrhagic stroke, subarachnoid hemorrhage, cerebral vasospasm, or transient ischemic attacks (TIA). In some embodiments, the stroke is ischemic. In some embodiments, the stroke is hemorrhagic. In some embodiments, the compound is administered within 48 hours of the stroke. In some embodiments, the compound is administered within 24 hours of the stroke. In some embodiments, the compound is administered within 16 hours of the stroke. In some embodiments, the compound is administered within 8, 4, 2, or 1 hours of the stroke. In some embodiments, the compound is administered for at least the first 1-72 hours following the stroke. In some embodiments, the compound is administered for at least the first 8-52 hours following the stroke. In some embodiments, the compound is administered for at least the first 8-48 hours following the stroke. In some embodiments, the compound is administered for at least the first 24-48 hours following the stroke. In some embodiments, the compound is administered chronically to treat the stroke as it occurs. In some embodiments, the compound is administered chronically to treat Transient Ischemic Attacks (TIA).

In some embodiments, the compound is administered chronically to treat ischemic stroke, hemorrhagic stroke, a subarachnoid hemorrhage, cerebral vasospasm, transient ischemic attacks (TIA), or treat a patient who is at an increased risk for a stroke, such as a patient who has had a stroke in the past and is at risk for a further stroke, such as a patient over the age of 40, 45, 50, 55, 60, 65, 70, 75, or 80 years of age.

In some embodiments, the compound treats an ischemia-reperfusion injury caused by the stroke.

Neurodegenerative Diseases

Neurodegenerative diseases are incurable, progressive, and ultimately debilitating syndromes resulting from the progressive degeneration and/or death of neurons in the brain and spinal cord. Neurodegeneration results in movement (ataxias) and/or cognitive function (dementias) disorders, and includes a spectrum of diseases such as Alzheimer's Disease (AD), Parkinson's Disease (PD), Huntington's Disease (HD), Multiple Sclerosis (MS), amyotrophic lateral sclerosis (ALS), and chronic traumatic encephalopathy (CTE). While many neurodegenerative diseases are principally genetic in origin, other causes can include viruses, alcoholism, tumors or toxins, and as is now clear, repetitive brain injuries.

Neurons accumulate cellular damage over time due to the foregoing factors, which is generally considered the reason why many neurodegenerative diseases associated with prolonged cellular stress, such as Alzheimer's disease and Parkinson's disease, occur in aged individuals. Dementias represent the predominant outcome of neurodegenerative diseases with AD representing approximately 60-70% of cases. (Kandale 2013) As discussed above, activation of neuroprotective and neurorestorative mechanisms can ameliorate the progression of one or more neurodegenerative diseases. Accordingly, in one aspect the present invention provides a method of treating a neurodegenerative disease or promoting recovery from a neurodegenerative disease, comprising administering to a patient in need thereof an effective amount of a compound described herein, or a pharmaceutically acceptable salt thereof or composition comprising the same.

In one aspect, the present invention provides a method of promoting neuroprotection or neurorestoration in a patient suffering from a neurodegenerative disease, comprising administering to the patient an effective amount of a compound described herein, or a pharmaceutically acceptable salt thereof or composition comprising the same. In some embodiments is provided a method of promoting neuroprotection or neurorestoration in a patient suffering from a neurodegenerative disease, comprising administering to the patient an effective amount of a compound described herein, or a pharmaceutically acceptable salt thereof or composition comprising the same, wherein the compound is an $A_3R$ agonist. In some embodiments is provided a method of promoting neuroprotection or neurorestoration in a patient suffering from a neurodegenerative disease, comprising administering to the patient an effective amount of a compound described herein, or a pharmaceutically acceptable salt thereof or composition comprising the same, wherein the compound is an $A_1R$ agonist. In other embodiments is provided a method of promoting neuroprotection or neurorestoration in a patient suffering from a neurodegenerative disease, comprising administering to the patient an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is a compound described in Table 1, or a pharmaceutically acceptable salt thereof or a composition comprising the same.

Alzheimer's Disease (AD)

An estimated 5.2 million Americans of all ages had AD in 2014; 11% of the population age 65 and older have AD. (Alzheimer's Association) By 2050, the number of people age 65 and older with AD is projected to nearly triple to a projected 13.8 million. In the U.S., the cost of providing care for AD patients is about $214 billion per year; 70% of this cost is covered by Medicare and Medicaid. The current trends would project these costs to grow to $1.2 trillion per year by 2050.

Activation of astrocytes and promoting neuroprotection and neurorestoration according to the present invention represents a new treatment option for AD. Accordingly, provided herein in one aspect is a method of treating AD or promoting neuroprotection or neurorestoration in a patient suffering from AD, comprising administering to the patient an effective amount of a compound described herein, or a pharmaceutically acceptable salt thereof or composition comprising the same. In some embodiments, the present invention provides a method of treating AD or promoting neuroprotection or neurorecovery in a patient suffering from AD, comprising administering to the patient an effective amount of a compound described herein, or a pharmaceutically acceptable salt thereof or composition comprising the same, wherein the compound is an $A_3R$ agonist. In some embodiments, the present invention provides a method of treating AD or promoting neuroprotection or neurorecovery in a patient suffering from AD, comprising administering to the patient an effective amount of a compound described herein, or a pharmaceutically acceptable salt thereof or composition comprising the same, wherein the compound is an $A_1R$ agonist. In some embodiments, the present invention provides a method of treating AD or promoting neuroprotection or neurorecovery in a patient suffering from AD, comprising administering to the patient an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is a compound described in Table 1, or a pharmaceutically acceptable salt thereof, or a composition comprising the same.

Parkinson's Disease (PD)

As many as one million Americans live with PD, and each year approximately 60,000 Americans are newly diagnosed not including the thousands of cases that go undetected. (Parkinson's Disease Foundation) The total combined direct and indirect cost of PD, including medical treatment, social security payments and lost income, is estimated to be nearly $25 billion per year in the United States. (Parkinson's Disease Foundation and Huse 2005)

Activation of neuroprotection and neurorestoration according to the present invention represents a new treatment option for PD. Accordingly, provided herein in one aspect is a method of treating PD or promoting neuroprotection or neurorestoration in a patient suffering from PD, comprising administering to the patient an effective amount of a compound described herein, or a pharmaceutically acceptable salt thereof or composition comprising the same. In some embodiments, the present invention provides a method of treating PD or promoting neuroprotection or neurorecovery in a patient suffering from PD, comprising administering to the patient an effective amount of a compound described herein, or a pharmaceutically acceptable salt thereof or composition comprising the same, wherein the compound is an $A_3R$ agonist. In some embodiments, the present invention provides a method of treating PD or promoting neuroprotection or neurorecovery in a patient suffering from PD, comprising administering to the patient an effective amount of a compound described herein, or a pharmaceutically acceptable salt thereof or composition comprising the same, wherein the compound is an $A_1R$ agonist. In some embodiments, the present invention provides a method of treating PD or promoting neuroprotection or neurorecovery in a patient suffering from PD, comprising administering to the patient an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is one of those described in Table 1, or a pharmaceutically acceptable salt thereof or a composition comprising the same.

Multiple Sclerosis (MS)

More than 400,000 people in the United States have MS. In young adults, MS represents the most prevalent disease of the central nervous system. (Multiple Sclerosis Foundation) There is potential for astrocytes to reverse the destruction of nerve cell myelin coatings that is caused by MS by their neurorestorative effects and promotion of healing in the damaged CNS of MS patients.

Activation of neuroprotection and neurorestoration in the CNS according to the present invention thus represents a new treatment option for MS. Accordingly, provided herein in one aspect is a method of treating MS or promoting neuroprotection or neurorestoration in a patient suffering from MS, comprising administering to the patient an effective amount of a compound described herein, or a pharmaceutically acceptable salt thereof or composition comprising the same. In some embodiments, the present invention provides a method of treating MS or promoting neuroprotection or neurorecovery in a patient suffering from MS, comprising administering to the patient an effective amount of a compound described herein, or a pharmaceutically acceptable salt thereof or composition comprising the same, wherein the compound is an $A_3R$ agonist. In some embodiments, the present invention provides a method of treating MS or promoting neuroprotection or neurorecovery in a patient suffering from MS, comprising administering to the patient an effective amount of a compound described herein, or a pharmaceutically acceptable salt thereof or composition comprising the same, wherein the compound is an $A_1R$ agonist. In some embodiments, the present invention provides a method of treating MS or promoting neuroprotection or neurorecovery in a patient suffering from MS, comprising administering to the patient an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is one of those described in Table 1, or a pharmaceutically acceptable salt thereof or a composition comprising the same.

Amyotrophic Lateral Sclerosis (ALS)/Lou Gehrig's Disease

Approximately 5,600 people in the U.S. are diagnosed with ALS each year; as many as 30,000 Americans may have the disease concurrently. (ALS Association) Activation of astrocytes can provide stimulation of recovery and repair of the neurons and their connections in an ALS patient.

Accordingly, provided herein in one aspect is a method of treating ALS or promoting neuroprotection or neurorestoration in a patient suffering from ALS, comprising administering to the patient an effective amount of a compound described herein, or a pharmaceutically acceptable salt thereof or composition comprising the same. Also provided in other embodiments is a method of stimulating recovery and repair of the neurons and their connections in an ALS patient, comprising administering to the patient an effective amount of a compound described herein, or a pharmaceutically acceptable salt thereof or composition comprising the same. In some embodiments, the present invention provides a method of treating ALS or promoting neuroprotection or neurorecovery in a patient suffering from ALS, comprising administering to the patient an effective amount of a compound described herein, or a pharmaceutically acceptable salt thereof or composition comprising the same, wherein the compound is an $A_3R$ agonist. In some embodiments, the present invention provides a method of treating ALS or promoting neuroprotection or neurorecovery in a patient suffering from ALS, comprising administering to the patient an effective amount of a compound described herein, or a pharmaceutically acceptable salt thereof or composition comprising the same, wherein the compound is an $A_1R$ agonist. In some embodiments, the present invention provides a method of treating ALS or promoting neuroprotection or neurorecovery in a patient suffering from ALS, comprising administering to the patient an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is one of those described in Table 1, or a pharmaceutically acceptable salt thereof or a composition comprising the same.

Chronic Traumatic Encephalopathy (CTE)

CTE (a form of tauopathy) is a progressive neurodegenerative disease found in individuals who have suffered one or more (often multiple, or repeated over the course of time) severe blows to the head. CTE is most often diagnosed in professional athletes in American football, soccer, hockey, professional wrestling, stunt performing, bull riding and rodeo performing, motocross, and other contact sports who have experienced brain trauma and/or repeated concussions. A subset of CTE sufferers have chronic traumatic encephalomyopathy (CTEM), which is characterized by motor neuron disease symptoms that mimic ALS. Progressive muscle weakness and motor and gait abnormalities are believed to be early signs of CTEM. First stage symptoms of CTE include progressive attention deficit, disorientation, dizziness, and headaches. Second stage symptoms comprise memory loss, social instability, erratic behavior, and poor judgment. In third and fourth stages, patients suffer progressive dementia, slowed movements, tremors, hypomimia, vertigo, speech impediments, hearing loss, and suicidality, and may further include dysarthria, dysphagia, and ocular abnormalities, e.g. ptosis.

Accordingly, provided herein in one aspect is a method of treating or preventing CTE or promoting neuroprotection or neurorestoration in a patient suffering from CTE, comprising administering to the patient an effective amount of a compound described herein, or a pharmaceutically acceptable salt thereof or composition comprising the same. Also provided in other embodiments is a method of stimulating recovery and repair of the neurons and their connections in a CTE patient, comprising administering to the patient an effective amount of a compound described herein, or a pharmaceutically acceptable salt thereof or composition comprising the same. In some embodiments, the compound treats one or more symptoms of first stage, second stage, third stage, or fourth stage CTE. In some embodiments, the present invention provides a method of treating CTE or promoting neuroprotection or neurorecovery in a patient suffering from CTE, comprising administering to the patient an effective amount of a compound described herein, or a pharmaceutically acceptable salt thereof or composition comprising the same, wherein the compound is an $A_3R$ agonist. In some embodiments, the present invention provides a method of treating CTE or promoting neuroprotection or neurorecovery in a patient suffering from CTE, comprising administering to the patient an effective amount of a compound described herein, or a pharmaceutically acceptable salt thereof or composition comprising the same, wherein the compound is an $A_1R$ agonist. In some embodiments, the present invention provides a method of treating CTE or promoting neuroprotection or neurorecovery in a patient suffering from CTE, comprising administering to the patient an effective amount of a compound described herein, or a pharmaceutically acceptable salt thereof or composition comprising the same, wherein the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound acts as an agonist of an $A_1$ adenosine receptor ($A_1R$). In some embodiments, the compound is a biased agonist, partial agonist, or biased partial agonist or antagonist at a $P2Y_1$ receptor. In some embodiments, the compound is one of those described in Table 1, or a pharmaceutically acceptable salt thereof or a composition comprising the same.

On a microscopic scale the pathology includes neuronal death, tau deposition, TAR DNA-binding Protein 43 (TDP 43) beta-amyloid deposition, white matter changes, and other abnormalities. Tau deposition includes the increasing presence of dense neurofibrillary tangles (NFT), neurites, and glial tangles, which are made up of astrocytes and other glial cells. Thus, in some embodiments, the method treats, enhances clearance or prevents neuronal death, tau deposition, TAR DNA-binding Protein 43 (TDP 43) beta-amyloid deposition, white matter changes, and other abnormalities associated with CTE.

In some embodiments, the present invention provides long-term administration of a compound disclosed herein, such as a biased agonist, partial agonist, or biased partial agonist of $A_3R$, or a dual agonist at an $A_3R$ and an $A_1R$, or a biased agonist, partial agonist, or biased partial agonist of $P2Y_1$, to treat a neurodegenerative disease, such as one of those described herein. In some embodiments, the present invention provides long-term administration of a compound disclosed herein, such as a biased agonist, partial agonist, or biased partial agonist of $A_1R$, to treat a neurodegenerative disease, such as one of those described herein.

Cardiovascular Diseases

Disclosed compounds are also useful in treating a variety of cardiovascular diseases and conditions. In some embodiments, the present invention provides a method of treating a heart (cardiac) or cardiovascular disease, such as cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis, comprising administering an effective amount of a compound described herein, or a pharmaceutically acceptable salt thereof or composition comprising the same. In some embodiments, a disclosed compound modulates ATP-sensitive potassium channels, for example via biased agonism, partial agonism, or biased partial agonism at an $A_3R$ receptor, or dual agonism at an $A_3R$ and an $A_1R$. In some embodiments, a disclosed compound modulates ATP-sensitive potassium channels via biased agonism, partial agonism, or biased partial agonism at an $A_1R$ receptor.

In some embodiments, the heart or cardiovascular disease is cardiac ischemia or myocardial infarction.

In some embodiments, the present invention provides a method of promoting or increasing cardioprotection, cardiorestoration, or cardioregeneration in a patient suffering from a heart (cardiac) or cardiovascular disease or condition, comprising administering to the patient an effective amount of a disclosed compound, for example one of those described in Table 1, or a pharmaceutically acceptable salt thereof or a composition comprising the same.

In some embodiments, the heart (cardiac) or cardiovascular disease from which the patient is suffering is cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis.

In some embodiments, the compound acts as an agonist of an $A_3$ adenosine receptor ($A_3R$). In some embodiments, the compound acts as a dual agonist of an $A_3R$ and an $A_1$ adenosine receptor ($A_1R$). In some embodiments, the compound acts as an agonist of an $A_1R$.

Other Diseases

Compounds that modulate beneficial effects such as neuroprotection, for example by increasing astrocyte mitochondrial activity, also have the potential to treat a variety of other diseases. For example, due to the role of astrocytes in neuroprotection disclosed in the present invention, activation of astrocytes, for example via modulation of $A_3R$, $A_1R$, and/or a $P2Y_1$ receptor, is useful in treating various diseases and conditions discussed below.

Accordingly, in some embodiments, the present invention provides a method of treating neurodegeneration in a patient suffering from a disease or condition, comprising administering to the patient an effective amount of a compound described herein, or a pharmaceutically acceptable salt thereof or composition comprising the same.

In some embodiments, the present invention provides a method of promoting or increasing neuroprotection, neurorestoration, or neuroregeneration in a patient suffering from a disease or condition, comprising administering to the patient an effective amount of a compound described herein, or a pharmaceutically acceptable salt thereof or composition comprising the same.

In some embodiments, the disease or condition is selected from autoimmune diseases, allergic diseases, and/or transplant rejection and graft-versus-host disease (for the use of certain nucleoside and nucleotide compounds in treating these conditions, see, for example, WO 2007/20018, hereby incorporated by reference). In other embodiments, the disease or condition is selected from intraocular hypertension and/or glaucoma (for the use of certain nucleoside and nucleotide compounds in treating these conditions, see, for example, WO 2011/77435, hereby incorporated by reference). In other embodiments, the disease or condition is selected from odor sensitivity and/or an olfactory disorder (for the use of certain nucleoside and nucleotide compounds in treating these conditions, see, for example, EP1624753, hereby incorporated by reference). In other embodiments, the disease or condition is type 2 diabetes (for the use of certain nucleoside and nucleotide compounds in treating these conditions, see, for example, US 2010/0256086, hereby incorporated by reference).

In other embodiments, the disease or condition is selected from respiratory diseases and/or cardiovascular (CV) diseases (for the use of certain nucleoside and nucleotide compounds in treating these conditions, see, for example, FASEB J. (2013) 27:1118.4 (abstract of meeting), hereby incorporated by reference). In other embodiments, the disease or condition is selected from deficits in CNS function, deficits in learning and/or deficits in cognition (for the use of certain nucleoside and nucleotide compounds in treating these conditions, see, for example, Neuropsychopharmacology. 2015 January; 40(2):305-14. doi: 10.1038/npp.2014.173. Epub 2014 Jul. 15. “Impaired cognition after stimulation of a $P2Y_1$ receptor in the rat medial prefrontal cortex,” Koch, H. et al. PMID: 25027332, hereby incorporated by reference). In other embodiments, the disease or condition is selected from a neurodegenerative disease such as Alzheimer’s disease, Parkinson’s disease, Huntington’s disease, prion disease, and/or amyotrophic lateral sclerosis (for the use of certain nucleoside and nucleotide compounds in treating these conditions, see, for example, U.S. Pat. No. 8,691,775, hereby incorporated by reference). In other embodiments, the disease or condition is selected from otic disorders, Meniere’s disease, endolymphatic hydrops, progressive hearing loss, dizziness, vertigo, tinnitus, collateral brain damage associated with radiation cancer therapy, and/or migraine treatment (for the use of certain nucleoside and nucleotide compounds in treating these conditions, see, for example, US 2009/0306225; UY31779; and U.S. Pat. No. 8,399,018, each of which is hereby incorporated by reference). In other embodiments, the disease or condition is selected from pathological sleep perturbations, depression, sleep disorders in the elderly, Parkinson's disease, Alzheimer's disease, epilepsy, schizophrenia, and/or symptoms experienced by recovering alcoholics (for the use of certain nucleoside and nucleotide compounds in treating these conditions, see, for example, US 2014/0241990, hereby incorporated by reference). In other embodiments, the disease or condition is selected from damage to neurons or nerves of the peripheral nervous system during surgery (for the use of certain nucleoside and nucleotide compounds in treating these conditions, see, for example, U.S. Pat. No. 8,685,372, hereby incorporated by reference). In other embodiments, the disease or condition is a cancer such as prostate cancer (for the use of certain nucleoside and nucleotide compounds in treating these conditions, see, for example, Biochem Pharmacol. 2011 August 15; 82(4): 418-425. doi:10.1016/j.bcp.2011.05.013. "Activation of the P2Y1 Receptor Induces Apoptosis and Inhibits Proliferation of Prostate Cancer Cells," Qiang Wei et al., hereby incorporated by reference). In other embodiments, the disease or condition is selected from one or more gastrointestinal conditions such as constipation and/or diarrhea (for the use of certain nucleoside and nucleotide compounds in treating these conditions, see, for example, Acta Physiol (Oxf). 2014 December; 212(4):293-305. doi: 10.1111/apha.12408. "Differential functional role of purinergic and nitrergic inhibitory cotransmitters in human colonic relaxation," Mañé N1, Gil V, Martinez-Cutillas M, Clavé P, Gallego D, Jiménez M; and Neurogastroenterol. Motil. 2014 January; 26(1):115-23. doi: 10.1111/nmo.12240. Epub 2013 Oct. 8. "Calcium responses in subserosal interstitial cells of the guinea-pig proximal colon," Tamada H., Hashitani H. PMID: 24329947, hereby incorporated by reference).

In other embodiments, the disease or condition is selected from cancer of the brain, such as glioblastoma (for the use of certain nucleoside and nucleotide compounds in treating these conditions, see, for example, Purinergic Signal. 2015 September; 11(3):331-46. doi: 10.1007/s11302-015-9454-7. Epub 2015 May 15. "Potentiation of temozolomide antitumor effect by purine receptor ligands able to restrain the in vitro growth of human glioblastoma stem cells." D'Alimonte, I. et al. PMID: 25976165, hereby incorporated by reference). In other embodiments, the disease or condition is selected from a gastrointestinal disorder such as diarrhea (for the use of certain nucleoside and nucleotide compounds in treating these conditions, see, for example, Acta Physiol (Oxf). 2014 December; 212(4):293-305. doi: 10.1111/apha.12408. "Differential functional role of purinergic and nitrergic inhibitory cotransmitters in human colonic relaxation," Mañé N., Gil V, Martinez-Cutillas M, Clavé P, Gallego D, Jiménez M., hereby incorporated by reference). In other embodiments, the disease or condition is impaired cognition (for the use of certain nucleoside and nucleotide compounds in treating this condition, see, for example, Neuropsychopharmacology. 2015 January; 40(2): 305-14. doi: 10.1038/npp.2014.173. Epub 2014 Jul. 15. "Impaired cognition after stimulation of $P2Y_1$ receptors in the rat medial prefrontal cortex," Koch H, Bespalov A, Drescher K, Franke H, Krugel U. PMID: 25027332, hereby incorporated by reference).

In some embodiments, the present invention provides a method of treating a disease or condition associated with brain injury or a neurodegenerative condition, such as epilepsy, migraine, collateral brain damage associated with radiation cancer therapy, depression, mood or behavioral changes, dementia, erratic behavior, suicidality, tremors, Huntington's chorea, loss of coordination of movement, deafness, impaired speech, dry eyes, hypomimia, attention deficit, memory loss, cognitive difficulties, vertigo, dysarthria, dysphagia, ocular abnormalities, or disorientation, comprising administering to a patient in need thereof an effective amount of a disclosed compound. In some embodiments, the compound is an $A_3R$ agonist. In some embodiments, the compound is an $A_1R$ agonist. In some embodiments, the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at an $A_1$ receptor. In some embodiments, the compound is a biased agonist, partial agonist, or biased partial agonist or antagonist at a $P2Y_1$ receptor. In some embodiments, the compound is one of those described in Table 1, or a pharmaceutically acceptable salt thereof or a composition comprising the same.

In further embodiments, the present invention provides a method of treating a neurodegenerative disease selected from the group consisting of Alzheimer's disease, Parkinson's disease, Huntington's disease, multiple sclerosis, amyotrophic lateral sclerosis, and prion disease in a patient in need thereof, comprising administering an effective amount of a compound described herein, or a pharmaceutically acceptable salt thereof or composition comprising the same. In some embodiments, the compound is an $A_3R$ agonist. In some embodiments, the compound is an $A_1R$ agonist. In some embodiments, the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at an $A_1$ receptor. In some embodiments, the compound is a biased agonist, partial agonist, or biased partial agonist or antagonist at a $P2Y_1$ receptor. In some embodiments, the compound is one of those described in Table 1, or a pharmaceutically acceptable salt thereof or a composition comprising the same.

In some embodiments, the improvement in cognitive or neurological function is measured as a score increase between about 1% and 20% in the delayed verbal recall task of the revised Wechsler Memory Scale. For example, the improvement in cognitive function may be measured as a score increase between about 1% and 10%, or between about 1% and 5%.

In some embodiments, the present invention provides a method of treating a brain or central nervous system (CNS) injury or condition selected from traumatic brain injury (TBI) or stroke, comprising administering to a patient in need thereof an effective amount of a compound described herein, or a pharmaceutically acceptable salt thereof or composition comprising the same.

In some embodiments, the brain or central nervous system (CNS) injury or condition is TBI. In some embodiments, the TBI is selected from concussion, blast injury, combat-related injury, or a mild, moderate or severe blow to the head.

In some embodiments, the compound described herein, or a pharmaceutically acceptable salt thereof or composition comprising the same, is administered within 24 hours of the TBI or stroke.

In some embodiments, the compound described herein, or a pharmaceutically acceptable salt thereof or composition comprising the same, is administered within 8 hours of the TBI or stroke.

In some embodiments, the compound described herein, or a pharmaceutically acceptable salt thereof or composition comprising the same, is administered at least during the first 8-48 hours following the TBI or stroke.

In some embodiments, the brain or central nervous system (CNS) injury or condition is stroke.

In some embodiments, the compound described herein, or a pharmaceutically acceptable salt thereof or composition comprising the same, is administered chronically to treat the stroke during the time period after the stroke has occurred as it resolves.

In some embodiments, neuroprotection or neurorestoration is increased in the patient as compared with an untreated patient.

In some embodiments, the compound is a biased partial agonist at a human $A_3$ adenosine receptor ($A_3R$). In some embodiments, the compound acts by dual agonism at an $A_3R$ and an $A_1R$. In some embodiments, the compound is a biased partial agonist at a human $A_1$ adenosine receptor ($A_1R$).

In some embodiments, the $A_3R$ is partially agonized in a manner biased toward neuroprotective functions of the $A_3R$ receptor.

In some embodiments, the compound described herein, or a pharmaceutically acceptable salt thereof or composition comprising the same, is administered orally, intravenously, or parenterally.

In one aspect, the present invention provides a method of increasing neuroprotection or neurorestoration in a patient who has suffered a TBI or stroke, comprising administering to a patient in need thereof an effective amount of a compound described herein, or a pharmaceutically acceptable salt thereof or composition comprising the same.

In some embodiments, the neuroprotection or neurorestoration decreases the recovery period after the TBI or stroke as compared with an untreated patient.

In some embodiments, the compound is a biased partial agonist at a human $A_3$ adenosine receptor ($A_3R$) and the $A_3R$ is partially agonized in a manner biased toward neuroprotective functions of the $A_3R$ receptor. In some embodiments, the compound acts by dual agonism at an $A_3R$ and an $A_1R$. In some embodiments, the compound is a biased partial agonist at a human $A_1$ adenosine receptor ($A_1R$) and the $A_1R$ is partially agonized in a manner biased toward neuroprotective functions of the $A_1R$ receptor. In some embodiments, the compound acts as an agonist at an $A_1R$.

In some embodiments, the compound described herein, or a pharmaceutically acceptable salt thereof or composition comprising the same, is administered orally, intravenously, or parenterally.

In one aspect, the present invention provides a method of treating an injury, disease, or condition selected from traumatic brain injury (TBI), stroke, a neurodegenerative condition, or a heart or cardiovascular disease, comprising administering to a patient in need thereof an effective amount of a compound described herein, or a pharmaceutically acceptable salt thereof or composition comprising the same.

In some embodiments, the injury, disease, or condition is TBI. In some embodiments, the TBI is selected from concussion, blast injury, combat-related injury, or a mild, moderate or severe blow to the head.

In some embodiments, the injury, disease, or condition is a stroke selected from ischemic stroke, hemorrhagic stroke, subarachnoid hemorrhage, cerebral vasospasm, or transient ischemic attacks (TIA).

In some embodiments, the neurodegenerative disease is selected from Alzheimer's Disease (AD), Parkinson's Disease (PD), Huntington's Disease (HD), Multiple Sclerosis (MS), amyotrophic lateral sclerosis (ALS), chronic traumatic encephalopathy (CTE), or a neurodegenerative condition caused by a virus, alcoholism, tumor, toxin, or repetitive brain injuries.

In some embodiments, the injury, disease, or condition is Parkinson's Disease.

In some embodiments, the injury, disease, or condition is Alzheimer's Disease, migraine, brain surgery, or a neurological side effect associated with cancer chemotherapy.

In some embodiments, the heart or cardiovascular disease is selected from cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis.

In some embodiments, the heart or cardiovascular disease is cardiac ischemia or myocardial infarction.

In some embodiments, the compound described herein, or a pharmaceutically acceptable salt thereof or composition comprising the same, is administered chronically to treat the stroke, cardiac ischemia, or myocardial infarction during the time period after the injury has occurred as it resolves.

In some embodiments, neuroprotection or neurorestoration is increased in the patient as compared with an untreated patient.

In some embodiments, the $A_3R$ is agonized in a biased manner toward neuroprotective functions of the $A_3R$ receptor via preferential activation of intracellular calcium mobilization with less, or no, activation of other $A_3R$-mediated pathways, or via preferential activation of Gq11-mediated intracellular calcium mobilization, Gi-mediated modulation of cAMP production, or Gi-mediated phosphorylation of ERK1/2 and Akt.

In some embodiments, the $A_3R$ is partially agonized in a manner biased toward cardioprotective functions of the $A_3R$ receptor via preferential activation of intracellular calcium mobilization with less, or no, activation of other $A_3R$-mediated pathways, or via preferential activation of Gq11-mediated intracellular calcium mobilization, Gi-mediated modulation of cAMP production, or Gi-mediated phosphorylation of ERK1/2 and Akt.

In some embodiments, the method increases neuroprotection or neurorestoration in a patient who is suffering from a neurological side effect associated with or resulting from cancer chemotherapy or brain surgery.

In some embodiments, the compound described herein, or a pharmaceutically acceptable salt thereof or composition comprising the same, is administered orally.

In one aspect, the present invention provides a method of increasing neuroprotection or neurorestoration in a patient who has suffered a TBI or stroke, thereby treating the TBI or stroke, comprising administering to a patient in need thereof an effective amount of a compound described herein, or a pharmaceutically acceptable salt thereof or composition comprising the same.

In one aspect, the present invention provides a method of increasing cardioprotection or regeneration of damaged heart tissue in a patient who has suffered a cardiac ischemia or myocardial infarction, thereby treating the cardiac ischemia or myocardial infarction, comprising administering to a patient in need thereof an effective amount of a compound described herein, or a pharmaceutically acceptable salt thereof or composition comprising the same.

In some embodiments, the recovery period after the TBI, stroke, cardiac ischemia, or myocardial infarction is decreased as compared with an untreated patient.

In some embodiments, the $A_3R$ is partially agonized in a manner biased toward neuroprotective functions of the $A_3R$ receptor.

In some embodiments, the $A_3R$ is partially agonized in a manner biased toward cardioprotective functions of the $A_3R$ receptor.

In some embodiments, the compound described herein, or a pharmaceutically acceptable salt thereof or composition comprising the same, is administered orally.

In some embodiments, the compound is a biased agonist of an $A_3R$ with improved cardioprotection function relative to a full $A_3R$ agonist.

In some embodiments, the compound is a biased agonist of an $A_3R$ with improved cardioprotection function relative to a full $A_3R$ agonist via preferential activation of one or more of the following $A_3R$-mediated pathways: activation of Gq11-mediated intracellular calcium mobilization, Gi-mediated modulation of cAMP production, Gi-mediated phosphorylation of ERK1/2 and Akt, or modulation of Beta-Arrestin activation.

In some embodiments, the compound is a biased agonist of an $A_3R$ with improved cardioprotection function relative to a full $A_3R$ agonist via preferential activation of intracellular calcium mobilization with less or no activation of the other $A_3R$-mediated pathways.

In some embodiments, the compound is a partial agonist of the $A_3R$ with improved cardioprotection function relative to a full $A_3R$ agonist.

Addictive Disorders

Disclosed compounds are also useful in treating addictions, addictive behaviors, behavioral addictions, compulsive disorders and behaviors, and related conditions.

The use of certain compounds in treating such addictions, behaviors, and disorders is described in WO/2019/157317, the contents of which are hereby incorporated by reference.

Cocaine self-administering mice exhibit significantly higher glutamate levels in the VTA (ventral tegmental area) of the brain. The VTA, in particular the VTA dopamine neurons, serve several functions in the reward system, motivation, cognition, and drug addiction, and may be the focus of several psychiatric disorders. The elevated glutamate levels appear to be due, at least in part, to loss of glutamate uptake into astrocytes. Without wishing to be bound by theory, it is believed that reduced availability of glutamate has negative effects on astrocyte function and this loss of function affects neuronal activity and drug-seeking behavior. It has now been found that the compounds disclosed herein treat or prevent relapse in addicted individuals, for example by reversing such loss of astrocyte function. Such loss of astrocyte function may be partly due to reduced expression of the glutamate transporter (GLT-1) in astrocytes. Since astrocytes metabolize glutamate to produce ATP, this likely impairs glutamate uptake, weakens astrocyte oxidative metabolism and downstream ATP-dependent processes and thereby weakens their ability to maintain an optimal environment for VTA neuronal activity.

Accordingly, in one aspect, the present invention provides a method of preventing, ameliorating, treating, or promoting recovery from an addiction, addictive behavior, behavioral addiction, brain reward system disorder, compulsive disorder, or related condition, comprising administering to a subject in need thereof an effective amount of a compound described herein, or a pharmaceutically acceptable salt thereof or composition comprising the same.

In some embodiments, the addiction is to an addictive substance. In some embodiments, the addictive substance is a prescription or recreational drug.

In some embodiments, the addictive substance is selected from alcohol, nicotine, a stimulant, a cannabinoid agonist, or an opioid agonist. In some embodiments, the addictive substance is selected from heroin, cocaine, alcohol, an inhalant, an opioid, nicotine, an amphetamine, or a synthetic analog, salt, composition, or combination thereof.

In some embodiments, the amphetamine is selected from bupropion, cathinone, MDMA, or methamphetamine.

In some embodiments, the prescription or recreational drug is selected from a cannabinoid agonist or opioid agonist.

In some embodiments, the addiction is an alcohol or nicotine addiction.

In some embodiments, the subject is a polydrug abuser.

In some embodiments, the prescription or recreational drug is selected from cocaine, heroin, bupropion, cathinone, MDMA, or methamphetamine morphine, oxycodone, hydromorphone, fentanyl, or a combination thereof.

In some embodiments, a disclosed compound increases energy metabolism mediated by astrocytes, such as astrocyte mitochondria. In some embodiments, the compound reverses loss of glutamate uptake into astrocytes caused by a substance with abuse potential. In some embodiments, the compound at least partially reverses the remodeling of the brain reward system caused by the addiction. In some embodiments, such effects are mediated by brain or CNS adenosine $A_3$ receptors, such as astrocyte $A_3R$ in the VTA; or microglia $A_3R$.

In another aspect, the present invention provides a method of preventing, ameliorating, treating, or promoting recovery from an addiction, addictive behavior, behavioral addiction brain reward system disorder, compulsive disorder, or related condition by increasing energy metabolism mediated by astrocytes, glia, microglia, neurons, endothelium cells, or other cells of the brain and/or CNS, comprising administering to a subject in need thereof an effective amount of a compound described herein, or a pharmaceutically acceptable salt thereof or composition comprising the same.

In some embodiments, the method treats or prevents a relapse of an addiction or addictive behavior in the subject. In some embodiments, the subject is addicted to one or more addictive substances such as addictive drugs (drugs having abuse potential). As described below, such drugs include prescription drugs and recreational drugs such as heroin, cocaine, nicotine, or an opioid agonist.

In another aspect, the present invention provides a method of treating or preventing withdrawal caused by addiction to one or more addictive substances or drugs, comprising administering to a subject in need thereof an effective amount of a compound described herein, or a pharmaceutically acceptable salt thereof or composition comprising the same. In some embodiments, the compound decreases withdrawal symptoms in an addicted individual in withdrawal. In some embodiments, the compound treats withdrawal in an addicted individual in withdrawal. In some embodiments, the method further comprises co-administering another drug for treating withdrawal and, optionally, counseling such as psychotherapy. In some embodiments, the method further comprises a cognitive behavioral therapy. In some embodiments, the method further comprises a digital therapeutic. Digital therapeutics include, for example, reSET or reSET-O (Pear Therapeutics).

In some embodiments, the present invention provides a method of treating or preventing a relapse of a compulsive disorder or compulsive behavior, comprising administering to a subject in need thereof an effective amount of a compound described herein, or a pharmaceutically acceptable salt thereof or composition comprising the same.

In some embodiments, the compulsive disorder is obsessive-compulsive disorder (OCD), Tourette syndrome, trichotillomania, anorexia, bulimia, anxiety disorder, psychosis, or post-traumatic stress disorder.

According to another aspect, the present invention provides a method for treating one or more behavioral addictions and addictive behaviors or disorders comprising administering to a subject in need thereof a compound described herein, or a pharmaceutically acceptable salt thereof or composition comprising the same. Behavioral addictions and addictive disorders result from the intoxication one senses from the release of brain chemicals (e.g., serotonin, adrenaline, epinephrine, etc.) during certain activities. Such disorders are known in the art and include gambling, sex addiction, pornography addiction, eating disorders, spending addiction, rage/anger, workaholism, exercise addiction, risk taking addictions (e.g. kleptomania and pyromania), perfectionism, internet or video game addiction, and compulsive use of electronic devices such as texting and checking social media, to name a few.

In some embodiments, activation of astrocytes is achieved through contacting with a disclosed compound one or more purinergic receptors such as adenosine receptors (ARs), for example those associated with or expressed by astrocytes or microglia, thus modulating the activity of the one or more receptors. In some embodiments, through effects on adenosine receptors such as $A_1$, $A_{2A}$, $A_{2B}$ and $A_3$ on astrocytes, the compound activates astrocytes to treat one or more disclosed diseases or conditions. In some embodiments, after administration to a subject in need thereof, a disclosed compound influences one or more functions such as glutamate uptake having an impact on energy metabolism of astrocytes or neuronal function, thus treating one or more diseases or conditions. In some embodiments, the compound is an AR agonist. In some embodiments, the purinergic receptor is an adenosine $A_3$ receptor ($A_3R$). In some embodiments, the compound is an $A_3R$ agonist. In some embodiments, the compound is a partial agonist or biased agonist or biased partial agonist, at an $A_3$ receptor ($A_3R$), such as a human $A_3$ receptor ($hA_3R$). In some embodiments, the compound is a biased antagonist at an $A_3$ receptor. In some embodiments, the compound acts by dual agonism at an $A_3R$ and an $A_1R$. In some embodiments, the compound is an $A_1R$ agonist. In some embodiments, the compound is one of those described in Table 1, or a pharmaceutically acceptable salt thereof or a composition comprising the same.

P2Y receptors are G-protein-coupled receptors and different subtypes of these receptors have important roles in processes such as synaptic communication, cellular differentiation, ion flux, vasodilation, blood brain barrier permeability, platelet aggregation and neuromodulation. Characterized members of the purinergic P2Y receptor family include the mammalian $P2Y_1$, $P2Y_{11}$, $P2Y_{12}$ and $P2Y_{13}$ receptors, which bind to adenine nucleotides; the $P2Y_4$, $P2Y_6$, and $P2Y_{14}$ receptors, that bind to uracil nucleotides; and the $P2Y_2$ and rodent $P2Y_4$ receptors, which have mixed selectivity. In some embodiments, activation of astrocytes is achieved through contacting with a disclosed compound one or more purinergic receptors such as P2Y receptors, for example those associated with or expressed by astrocytes, thus modulating the activity of the one or more receptors. In some embodiments, through effects on P2Y receptors such as $P2Y_1$, $P2Y_{11}$, $P2Y_{12}$ and $P2Y_{13}$ receptors associated with or expressed by astrocytes, the compound activates astrocytes to treat one or more disclosed diseases or conditions. In some embodiments, the P2Y receptor is a $P2Y_1$ receptor. In some embodiments, the $P2Y_1$ receptor is located on intracellular mitochondrial membranes. In some embodiments, the compound is a P2Y agonist. In some embodiments, the compound is a $P2Y_1$ agonist, e.g. at a human $P2Y_1$ receptor. In some embodiments, the compound is a biased agonist, partial agonist, or biased partial agonist at a $P2Y_1$ receptor, such as a human $P2Y_1$ receptor. In some embodiments, the compound is a biased antagonist at a $P2Y_1$ receptor. In some embodiments, the compound is one of those described in Table 1, or a pharmaceutically acceptable salt thereof or a composition comprising the same.

As used herein, the term “addiction” includes, unless otherwise specified, physical or psychological dependence on a substance. Addiction may involve withdrawal symptoms or mental or physical distress if the substance is withdrawn. Addiction includes drug liking, drug dependence, habit-formation, neurological and/or synaptic changes, development of brain reward system disorders, behavioral changes, or other signs or symptoms of addiction in a subject.

As used herein, the term “addictive drug” or “drug having abuse potential” includes drugs and other substances such as nicotine, whether approved by a regulatory body for treatment of a disease or not, that are known to result in clinical, behavioral, or neurological manifestations of addiction or compulsive behavior. In some embodiments, the addictive drug includes nicotine, a cannabinoid agonist, a stimulant, or an opioid agonist. “Addictive substance” refers to addictive drugs as well as other substances of abuse such as alcohol. Examples of addictive substances thus include heroin, cocaine, alcohol, opiates, nicotine, inhalants, amphetamines, and their synthetic analogs.

Pain Conditions and Disorders

Disclosed compounds are also useful in treating pain, pain disorders, and related conditions. Accordingly, in one aspect, the present invention provides a method of treating, preventing, promoting recovery from, or ameliorating a pain condition or disorder, comprising administering to a subject in need thereof an effective amount of a compound described herein, or a pharmaceutically acceptable salt thereof or pharmaceutical composition thereof. In some embodiments, the compound is one of those described in Table 1.

In some embodiments, the pain condition or disorder is pain control. For the use of certain nucleoside and nucleotide compounds in treating this and related conditions, see, for example, US 2010/0256086, hereby incorporated by reference.

In other embodiments, the pain condition or disorder is selected from pain mediated by the CNS, such as neuropathic pain, inflammatory pain, or acute pain. For the use of certain nucleoside and nucleotide compounds in treating these conditions, see, for example, Br J Pharmacol. 2010 March; 159(5):1106-17. doi: 10.1111/j.1476-5381.2009.00596.x. Epub 2010 Feb. 5. “A comparative analysis of the activity of ligands acting at P2X and P2Y receptor subtypes in models of neuropathic, acute and inflammatory pain.” Andõ RD1, Méhész B, Gyires K, Illes P, Sperlágh B. PMID: 20136836, hereby incorporated by reference.

In some embodiments, the pain condition or disorder is migraine.

In some embodiments, the pain condition or disorder is neuropathic pain, inflammatory pain, or acute pain. See, e.g., Tosh, D. K.; Padia, J.; Salvemini, D.; Jacobson, K. A. Efficient, large-scale synthesis and preclinical studies of MRS5698, a highly selective $A_3$ adenosine receptor agonist that protects against chronic neuropathic pain. *Purinergic Signalling* 2015, 11, 371-387.

In some embodiments, the pain condition or disorder is central pain syndrome, peripheral neuropathy, corneal neuropathic pain, post stroke pain, or pain caused by multiple sclerosis.

Pharmaceutically Acceptable Compositions

According to another embodiment, the invention provides a composition comprising a disclosed compound and a pharmaceutically acceptable carrier, adjuvant, or vehicle. In certain embodiments, a composition of this invention is formulated for administration to a patient in need of such composition. In some embodiments, a composition of this invention is formulated for oral administration to a patient.

The term "biological sample," as used herein, includes, without limitation, cell cultures or extracts thereof, biopsied material obtained from a mammal or extracts thereof, and blood, saliva, urine, feces, semen, tears, or other body fluids or extracts thereof.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage. The expression "unit dosage form," as used herein, refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 0.01 mg/kg to about 25 mg/kg, of subject body weight per day, one or more times a day, to obtain the desired therapeutic effect. In certain embodiments, the compounds of the invention are administered orally or parenterally at dosage levels of about 0.01 mg/kg to about 50 mg/kg, or about 0.01 mg/kg to about 25 mg/kg, or about 0.05 mg/kg to about 10 mg/kg, or about 0.05 mg/kg to about 5 mg/kg, or about 0.1 mg/kg to about 2.5 mg/kg, of subject body weight per day, one or more times a day, to obtain the desired therapeutic effect.

Liquid dosage forms for oral administration include, but are not limited to, pharmaceutically acceptable emulsions, liposomes, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters), poly(anhydrides) and cyclodextrins and modified cyclodextrins (such as SBE-bCD). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention can also be administered topically, such as directly to the eye, e.g., as an eye-drop or ophthalmic ointment. Eye drops typically comprise an effective amount of at least one compound of the invention and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, 1985, Trans Ophthalmol Soc U K 104(Pt 4): 402-9; Ashton et al., 1991, J Pharmacol Exp Ther 259(2): 719-24; Green et al., 1971, Am J Ophthalmol 72(5): 897-905). The most commonly used penetration enhancer is benzalkonium chloride (Tang et al., 1994, J Pharm Sci 83(1): 85-90; Burstein et al, 1980, Invest Ophthalmol Vis Sci 19(3): 308-13), which also works as preservative against microbial contamination. It is typically added to a final concentration of 0.01-0.05%.

Combinations with Other Therapeutic Agents

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In certain embodiments, a provided compound, or composition thereof, is administered in combination with other therapeutic agents, such as tissue plasminogen activators, blood thinners, statins, ACE inhibitors, angiotensin II receptor blockers (ARBs), beta blockers, calcium channel blockers or diuretics, to a patient in need thereof.

In certain embodiments, the tissue plasminogen activator used in combination with compounds or compositions of the invention include, but are not limited to, alteplase, desmoteplase, reteplase, tenecteplase, or combinations of any of the above.

In certain embodiments, the blood thinners used in combination with compounds or compositions of the invention include, but are not limited to, warfarin, heparin, apixabam, clopidogrel, aspirin, rivaroxaban, dabigatran, or combinations of any of the above.

In certain embodiments, the statins used in combination with compounds or compositions of the invention include, but are not limited to, atorvastatin, rosuvastatin, fluvastatin, lovastatin, pravastatin, simvastatin and pitavastatin, cerivastatin, mevastatin, or combinations of any of the above.

In certain embodiments, the ACE inhibitors used in combination with compounds or compositions of the invention include, but are not limited to, captopril, enalapril, fosinopril, lisinopril, moexipril, perindopril, quinapril, ramipril, trandolapril benazepril, or combinations of any of the above.

In certain embodiments, the angiotensin II receptor blockers (ARBs) used in combination with compounds or compositions of the invention include, but are not limited to, azilsartan, candesartan, eprosartan, irbesartan, losartan, olmesartan, telmisartan, valsartan, fimasartan, or combinations of any of the above.

In certain embodiments, the beta blockers used in combination with compounds or compositions of the invention include, but are not limited to, atenolol, bisoprolol, betaxolol, carteolol, carvedilol, labetalol, metoprolol, nadolol, nebivolol, oxprenolol, penbutolol, pindolol, propranolol, timolol, or combinations of any of the above.

In certain embodiments, the calcium channel blockers used in combination with compounds or compositions of the invention include, but are not limited to, dihydropyridines: amlodipine, cilnidipine, clevidipine, felodipine, isradipine, lercanidipine, levamlodipine, nicardipine, nifedipine, nimodipine, nisoldipine, nitrendipine, diltiazem, verapamil, or combinations of any of the above.

In certain embodiments, the diuretics used in combination with compounds or compositions of the invention include, but are not limited to, loop diuretics, thiazide diuretics, thiazide-like diuretics and potassium-sparing diuretics, or combinations of any of the above.

In certain embodiments, the loop diuretics used in combination with compounds or compositions of the invention include, but are not limited to, bumetanide, ethacrynic acid, furosemide, torsemide, or combinations of any of the above.

In certain embodiments, the thiazide diuretics used in combination with compounds or compositions of the invention include, but are not limited to, epitizide, hydrochlorothiazide and chlorothiazide, bendroflumethiazide, methyclothiazide, polythiazide, or combinations of any of the above.

In certain embodiments, the thiazide-like diuretics used in combination with compounds or compositions of the invention include, but are not limited to, indapamide, chlorthalidone, metolazone, or combinations of any of the above.

In certain embodiments, the potassium-sparing diuretics used in combination with compounds or compositions of the invention include, but are not limited to, amiloride, triamterene, spironolactone, eplerenone, or combinations of any of the above.

In certain embodiments, a provided compound, or composition thereof, is administered in combination with a mechanical thrombectomy device, to a patient in need thereof. In certain embodiments, the mechanical thrombectomy device is a stroke thrombectomy device or a coil embolization device for cerebral aneurysm. In certain embodiments, such a device includes, but is not limited to, a coil retriever, an aspiration device or a stent retriever.

In certain embodiments, a combination of 2 or more therapeutic agents may be administered together with compounds or compositions of the invention. In certain embodiments, a combination of 3 or more therapeutic agents may be administered together with compounds or compositions of the invention.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the present invention, an additional therapeutic agent, and a pharmaceutically acceptable carrier, adjuvant, or vehicle.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between about 0.001-100 mg/kg body weight/day of the additional therapeutic agent can be administered, or about 0.001 mg/kg to about 500 μg/kg, or about 0.005 mg/kg to about 250 μg/kg, or about 0.01 mg/kg to about 100 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of the present invention and one or more additional therapeutic agents. The therapeutic agent may be administered together with a compound of the present invention, or may be administered prior to or following administration of a compound of the present invention. Suitable therapeutic agents are described in further detail below. In certain embodiments, a compound of the present invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of the present invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a medicament comprising at least one compound of the present invention or a pharmaceutically acceptable salt thereof and a pharmaceutically acceptable carrier.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1: Convergent Synthesis of 2-thioether-substituted (N)-methanocarba-nucleosides Advantages of the Novel Synthetic Route:

In the past, lengthy, inefficient, linear routes have been used to prepare (N)-methanocarba-nucleoside analogs. This class of compounds is being investigated as purine receptor ligands whose rigid, bicyclic sugar may provide altered binding due to a pre-established, receptor-preferred conformation. To introduce this rigid ribose substitute, a Mitsunobu reaction of a protected [3.1.0]bicyclohexane ribose analog with a nucleobase is typically followed by multiple steps of functional group modifications. Mitsunobu and alternative glycosylation methods suffer from unpredictable yields and regio- and stereoselectivities. We herein disclose an efficient, scalable convergent synthesis for 2-substituted (N)-methanocarba-adenosines. We surprisingly found that when the adenine moiety was pre-functionalized with 2-thioethers and other groups before coupling the bicyclic precursor (3), we were able to obtain a high yield of the desired Mitsunobu product. This new approach provided the (N)-methanocarba-adenosines in improved yields over known glycosylation methods, which effectively increased the overall yield compared to a linear synthesis and conserved a key intermediate 3, itself a product of nine sequential steps. Advantages of this new route include its generality for producing nucleoside analogs with various 2-halo, 2-thioether, and 2-alkyloxy substituents; its efficiency due to its convergent route (e.g., reduced number of total chemical transformations, or steps); and its improved overall yield. For example, using the known, linear synthesis, we initially prepared the AR agonist 8a (MRS4322; compound I-1) on a scale of 137 g with an overall yield of only 1.0% after thirteen steps starting from D-ribose (7.0 kg), including a yield of only 28.1% over the last four steps (Scheme 1). In sharp contrast, the novel, convergent synthetic route described herein provided 520 g of 8a with an overall yield of 60% from compound 3 using Scheme 2B. An even better overall yield of 83% was achieved on a laboratory scale. The outstanding advantage of the convergent route is that it spares the precious intermediate 3, which itself requires nine steps from D-ribose to prepare. We calculate that the synthesis required 540 g of 3 per 100 g of 8a by the linear route compared to 230 g of 3 per 100 g of 8a for the convergent route. Thus, the molar ratio of the key precursor 3 in the convergent route was reduced by 57% compared to the linear synthesis. A further advantage is that the yield of the Mitsunobu glycosylation reaction was increased from 42% for the known, linear route to more than double (95%) for compound 22a or 25a, which were then used to prepare 8a as shown in Scheme 2.

Introduction

Nucleoside derivatives are used widely in a therapeutic capacity in cancer, infectious disease and other conditions (references 1 and 2). One means of increasing the specificity of action of nucleosides and nucleotides is to constrain the ribose ring in a preformed conformation that is complementary to the requirements at a target biopolymer, such as an enzyme or receptor protein. For example, the introduction of a North (N)-methanocarba ([3.1.0]bicyclohexane) ring system in place of the tetrahydrofuryl group of native ribose lowers the energy barrier in binding at a biological target, resulting in increased affinity and selectivity (references 3-6), e.g., of nucleosides at the $A_3$ adenosine receptor (AR) or of nucleotides at the $P2Y_1$ receptor ($P2Y_1R$). Substitution at the adenine C2 position with secondary amines, ethers, thioethers or alkynes is of particular interest in biological studies at purinergic receptors. For example, adenosine 2-thioethers in the native ribose series displayed enhanced AR affinity, and an adenine 2-methylthio group is a favored substitution in various P2YR ligands (references 7 and 8). Also of note are 2-methylthio nucleotide derivatives that act as potent P2YR agonists, including selective $P2Y_1R$ agonist MRS2365 1 ($K_i$ 0.4 nM), which is a (N)-methanocarba analogue of 2-methylthioadenosine 5'-diphosphate (reference 6). Similarly, among AR ligands the potent $A_3AR$ agonist MRS3611 2 ($K_i$ 1.5 nM) is an (N)-methanocarba analogue having a 2-methylthio substitution (reference 5). PP-77 ci

1

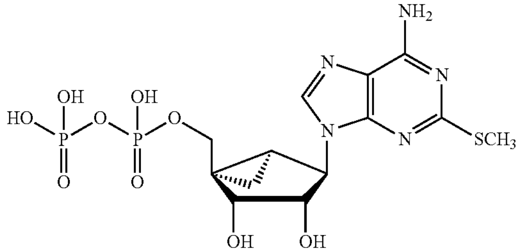

MRS2365

-continued

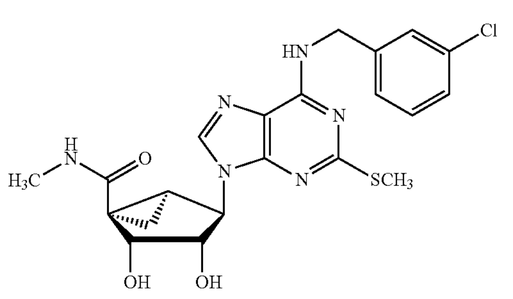

MRS3611

Although (N)-methanocarba nucleosides have broad application as ligands for various G protein-coupled receptors (GPCRs) and enzymatic targets (references 10 and 25), the conventional synthetic routes involve many linear steps and the overall final yield is typically <1% from readily available starting materials such as D-ribose (references 9-13). Thus, it is of interest to identify more efficient synthetic approaches that might be adaptable to pharmaceutical development. We have discovered a new, convergent synthetic route useful in preparing 2-methylthio-(N)-methanocarba-adenosine (MRS4322, an $A_3AR$ agonist with cerebroprotective efficacy; references 14 and 24) and related compounds. The new route increases overall yield and optimally uses the precious [3.1.0]bicyclohexane intermediate. The route is generally applicable and scalable for the synthesis of (N)-methanocarba-adenosine derivatives having varying C2 position substitution.

Results and Discussion:

Linear Route

Typically, a linear route (Scheme 1) is used to prepare appropriately functionalized (N)-methanocarba-adenosine derivatives, including those containing a 2-alkylthio group, e.g. 2-methylthio derivative 8a (references 10-12). The final 2-alkylthioadenine nucleosides and related nucleotides are designed to activate purine receptors (references 5 and 6). The synthesis features a protected key bicyclic intermediate, shown here as the 5'-trityl intermediate 3, which is a precursor of the pseudoribose moiety. Most commonly, a tert-butyldimethylsilyl (TBDMS) ether protection of the 5'-hydroxyl group of the intermediate analogous to 3 has been used (reference 12). However, we have found that this precursor and subsequent nucleoside intermediates are sticky materials, which are difficult to handle for large scale production in process chemistry. We have used a 5'-trityl protecting group of the corresponding bicyclic intermediates, following the routes of Choi et al. and Michel and Strazewski (references 11 and 13), which provided easily crystallizable intermediates leading to 3 in nine steps from D-ribose. As shown in Scheme 1, the nucleoside derivative 5 was obtained in a relatively low yield (42%) from the intermediate 3 by a Mitsunobu reaction. We initially prepared the AR agonist 8a (MRS4322; compound I-1) on a scale of 137 g with an overall yield of 1.0% after thirteen steps starting from D-ribose (7.0 kg), including 28.1% for the last four steps (Scheme 1), using this linear route with 5'-trityl protection.

Moreover, the Mitsunobu reaction of 2,6-dichloropurine 4 with alcohols can lead to the undesired $N^7$-regioisomer (reference 15). There are a few reports that also mentioned the $N^9$-alkylation of 6-chloro-2-NH-Boc adenine derivatives in good yields, using various alcohols via a Mitsunobu reaction (references 18 and 19). Therefore, we explored new methods that could successfully transform the key precursor 3 into the desired nucleoside $N^9$-regioisomer with a 2-alkylthioadenine nucleobase.

Scheme 1: Linear route for preparation of 2-substituted (N)-methanocarba adenosine derivatives

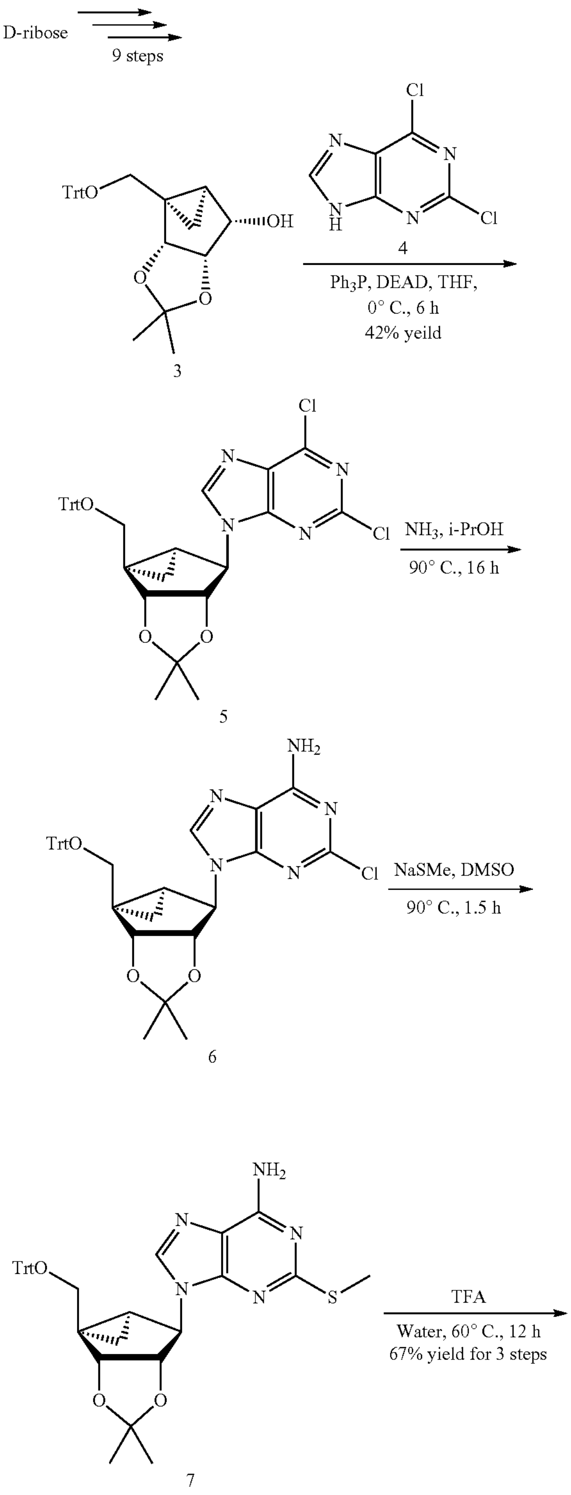

-continued

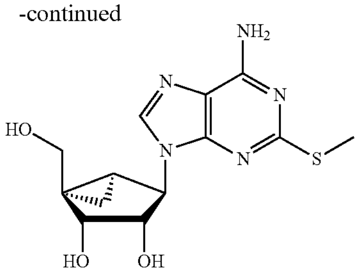

8a
(Compound I-1)

Adenine Pre-Functionalization for Alternative Routes

As an alternative synthetic approach, rather than coupling a bicyclic intermediate (e.g. 3), either in the ribo (2'-OH) or 2'-deoxy (N)-methanocarba series, to a reactive (6-chloro or 2,6-dichloro) purine nucleobase precursor (e.g., 4; references 5, 6, and 9), we pre-functionalized the purine in a manner that we discovered would facilitate high yields in a subsequent Mitsunobu step. Selective protection of the exocyclic primary amine was necessary, because earlier attempts to couple various adenine derivatives containing a free 6-$NH_2$ through a Mitsunobu reaction failed (reference 9). It remains unclear if this was due to the formation of phosphazane complexes (references 20 and 21) with the betaine intermediate, or to the poor solubility of the 6-$NH_2$-purine.

With the goal of improving the synthetic route to adenine 2-thioether derivatives, we first prepared $N^6$,$N^6$-di-Boc-2-chloro-adenine 11 in two steps based on a literature report (reference 13; Scheme S1). The di-Boc protected adenine derivative obtained was used in a Mitsunobu reaction with the alcohol (3), and it was found that only ~10% of the coupling product 12 was observed by $^1$H-NMR, in contrast to the quantitative synthesis of similar kind of analog under identical conditions that was reported by Michel et al. (reference 13). Work to optimize these conditions is underway. Despite the poor yield, the use of the convergent route by coupling 11 with 3 provides the advantage of minimizing the number of linear steps after the Mitsunobu, thus reducing the amount of the expensive intermediate 3.

Scheme S1.

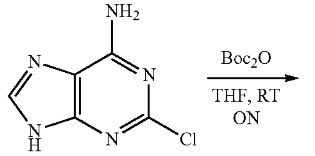

9

-continued

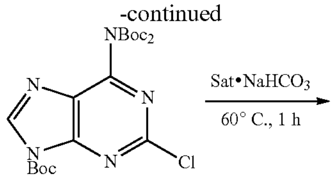

10

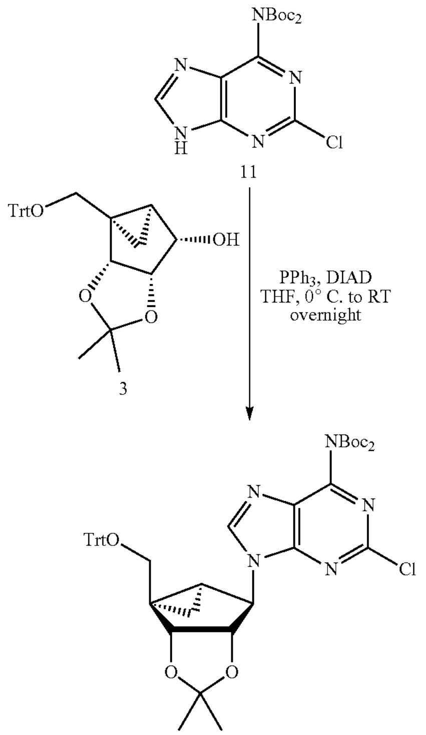

11

3

12
~10% by $^1$H NMR

We then attempted to protect the amine of 2-Cl-adenine 9 using tetramethylsuccinic anhydride ($M_4SA$; reference 16), but the desired tetramethylsuccinoyl-protected product 14 could not be isolated in pure form from the reaction mixture, although a substantial product peak was observed by mass spectrometry (Scheme S3). It is believed that isolation of 14 followed by coupling in the Mitsunobu reaction with 3 would provide improved coupling yields relative to 11 or 15. Protection to yield N-phthaloyl derivative 15 was successful but had a low yield (<10%).

Scheme S3.

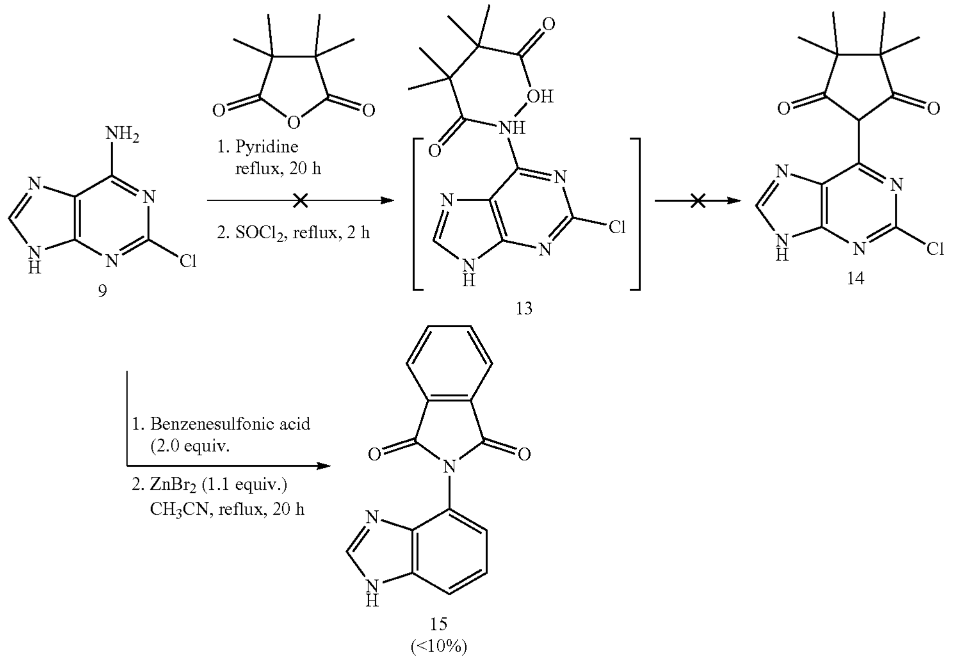

9 13 14

15 (<10%)

Convergent Route

The need for an efficient and scalable synthesis led us to investigate a convergent route that envisaged the use of protected forms of 2-substituted adenine derivatives (e.g., 2-alkylthioadenine derivatives 16) as precursors for a subsequent Mitsunobu reaction to obtain the corresponding (N)-methanocarba nucleoside derivatives 8. In this context, we first synthesized 2-methylthioadenine 16a in high yield by treating 2-Cl-adenine 9 with sodium methylthiolate at elevated temperature (Scheme 2A).

We also considered the phthaloyl group for the amino-protection of 16a since it has a good regioselectivity for the β-$N^9$-nucleoside derivatives (reference 16), but the yield of the $N^6$-substituted phthalimide product 17 was low (Scheme S4).

Scheme S4. Low overall yield synthesis of final nucleoside 8a via phthaloyl-protected nucleobase 17.

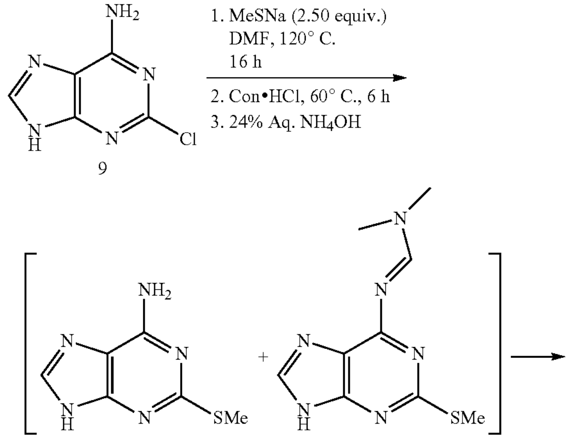

9

-continued

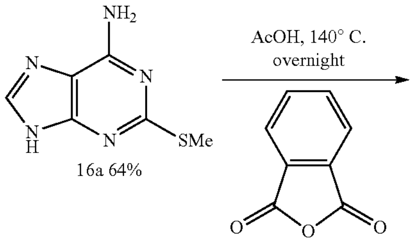

16a 64%

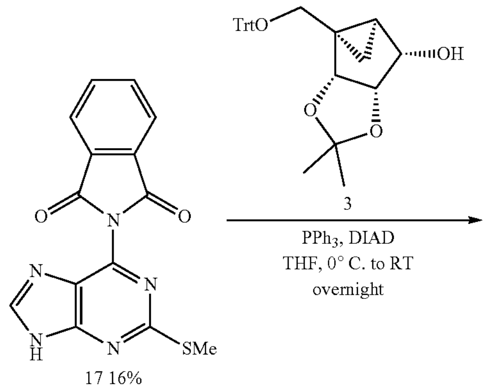

3

17 16%

-continued

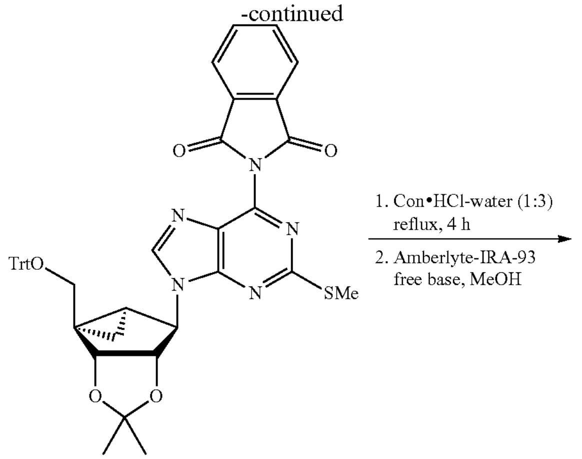

18 85%

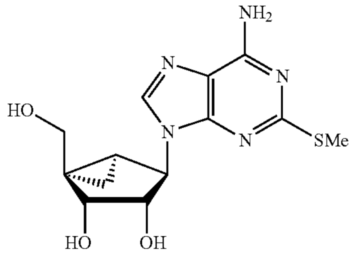

8a (41% isolated)
Compound I-1

2-Methylthioadenine 16a was treated overnight with phthalic anhydride in AcOH at 140° C. to obtain the 2-MeS—$N^6$-phthaloyl-adenine 17 in poor yield (16%), which was coupled to the alcohol (3) under Mitsunobu conditions to afford the desired adduct, a β-$N^9$-nucleoside derivative (18) in high yield (85%). However, the attempts to improve the yield of 17 failed. We used phthaloyl chloride, phthalic anhydride with a catalytic amount of p-toluenesulfonic acid (0.1 equivalents), and the conditions ($ZnBr_2$ and bis(trimethylsilyl)acetamide (BSA)) for the synthesis of N-alkyl- and N-arylimide derivatives (reference 17).

Consequently, we investigated the reactivity of $N^6$-Boc-protected 2-MeS-adenine 20a with the alcohol 3 in a Mitsunobu reaction (Scheme 2B). The 2-thioether 16a was first Boc-protected with excess Boc-anhydride to yield a mixture of N-tert-butoxycarbonyladenine intermediates, 19a ($N^6$,$N^6$,$N^9$-tri-tert-butoxycarbonyladenine) and 21a ($N^6$,$N^b$-di-tert-butoxycarbonyladenine). The corresponding tri-Boc derivative 19a formed during the reaction was largely cleaved in mild basic conditions to the $N^6$-mono-Boc derivative 20a. The di-Boc intermediate 21a was found to be less stable than mono-Boc 20a, as it gradually decomposed, even upon long-term storage as a solid at room temperature, to mono-Boc 20a as indicated by TLC.

(A) Adenine Pre-Functionalization

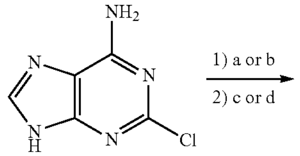

9

-continued

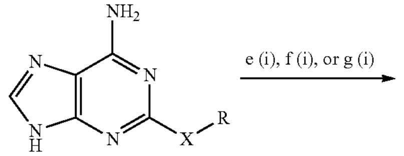

16a-f

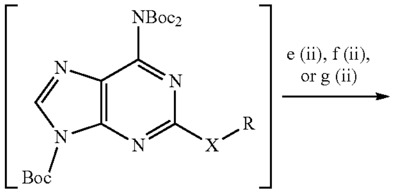

19

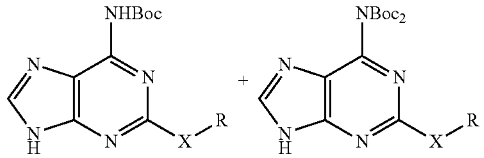

20a-f 21a, 21d (B) Discovery Chemistry Route:

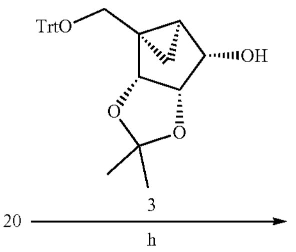

3

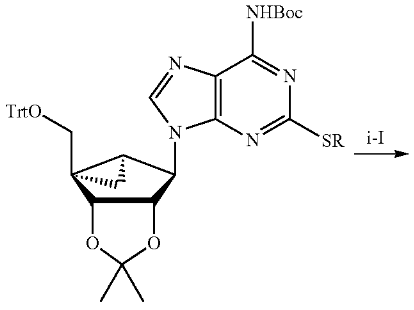

22a-f

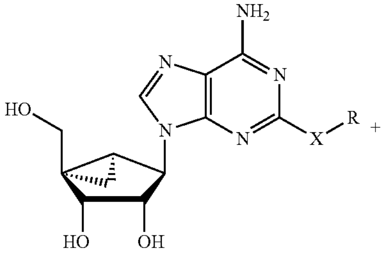

8a-f

-continued

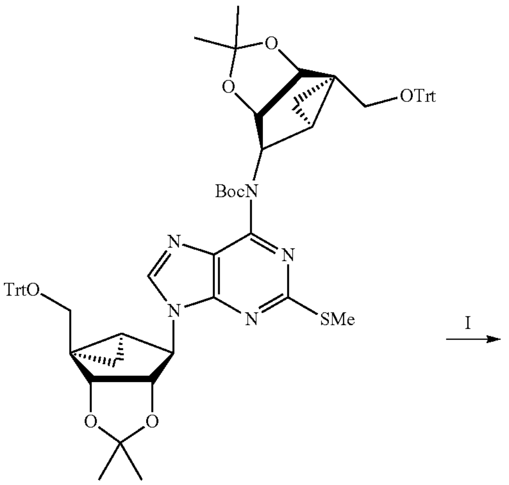

23 (trace impurity)

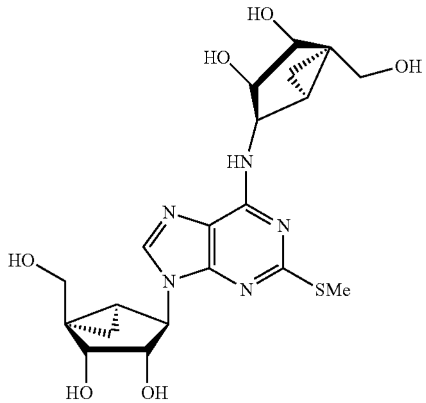

24

Compounds 8 and 16-25 a X=S, R=Me b X=S, R=Et c X=S, R=n-Hex d X=S, R=c-Hex e X=S, R=$CH_2Ph$ f X=S, R=$(CH_2)_2Ph$ g X=O, R=Me (C) Process Development Route:

Scheme 2.

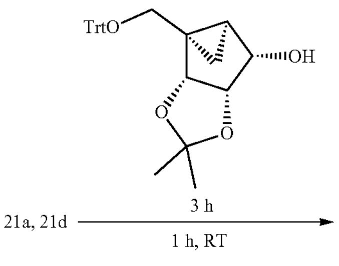

-continued

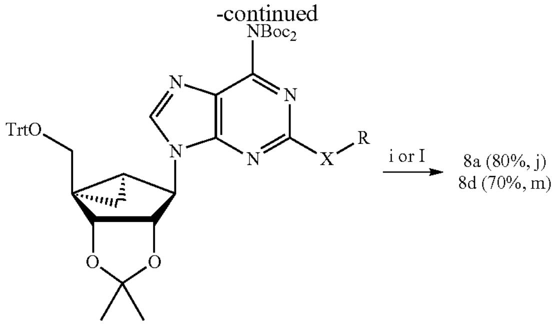

25a (95%)
25d (83%)

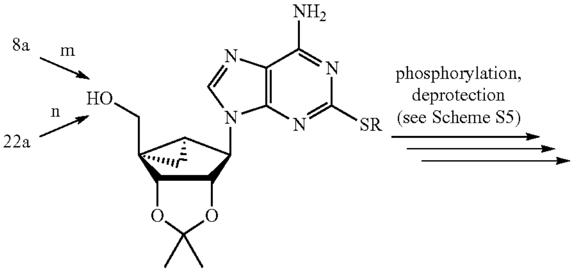

26a

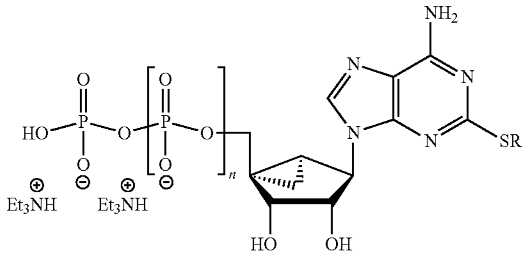

27 R = $CH_3$, n = 1
28 R = $CH_3$, n = 2

General reaction scheme using the convergent route for preparation of 2-thioether-substituted (N)-methanocarba adenosine derivatives (8a-g) and nucleotides (27 and 28, Scheme S5). An "a" designation after the compound numbers refers to R = Me. Other substituents are shown in Table 2. Reaction conditions: [a] (i) aq. NaSMe (3.0 equiv.), 140° C., autoclave, 16 h; (ii) 6 N HCl to pH=7~8; [b] (i) NaSMe (2.5 equiv.), DMF, 110° C., 16 h; (ii) 6N HCl, 60° C., 2h; (iii) aq. $NH_4OH$ (23%); [c] RSH (5 equiv.), $CsCO_3$ (3.0-3.5 equiv.), DMF, 140° C., 1 day; [d] NaOMe (20 equiv.), MeOH, 150° C., 4 days; [e] (i) $Boc_2O$ (4.0 equiv.), DMAP (0.2 equiv.), THF; (ii) aq. 10% NaOH, MeOH, 5-6 h; [f] (i) $Boc_2O$ (4.0 equiv.), DMAP (0.2 equiv.), THF; (ii) aq. $NH_4OH$ (23%), THF, 6 h; [g] (i) $Boc_2o$ (4.0 equiv.), DMAP (0.2 equiv.), THF; (ii) sat. $NaHCO_3$, MeOH-$H_2o$ (1:1), 60° C., 5-16 h; [h] 20 or 21 (1.1-1.2 equiv.), alcohol 3 (1.0 equiv.) $PPh_3$ (1.5-2.0 equiv.), Diisopropyl azodicarboxylate (DIAD) (1.5-2.0 equiv.), THF, 1-2 h; [i] (i) aq. 4N HCl or 4N HCl (g) /MeOH, 35° C., 16 h; (ii) $Na_2CO_3$, MeOH/$H_2O$. [j] 1N HCl in $H_2O$, 50° C., 18 h; (ii) Amberlite resin-93, MeOH, 16 h; [k] aq. 4N HCl in MeOH, 35° C., 16 h; (ii) Amberlite resin-93, MeOH, 16

The Mitsunobu reaction with either mono-Boc 20a or di-Boc 21a nucleobase (Schemes 2B and 2C) with a 5'-O-trityl bicyclic intermediate 3 proceeded in high yield to provide only $N^9$-regioisomers 22a or 25a, respectively, as shown in Table 2. Following acidic deprotection of 22a or 25a, nucleoside 8a was obtained, and this step to remove three protecting groups simultaneously proceeded in high yield. The isolated mono-Boc intermediate 20a contained a small amount of unprotected 16a as an impurity, which was problematic for the purity of subsequent steps leading to 8a. The presence of a small amount of the di-Boc compound 21a in the mono-Boc intermediate 20a was not detrimental during the Mitsunobu reaction, because its Mitsunobu product (25a) was later deprotected to yield the same product 8a. However, we preferred the di-Boc approach (Scheme 2C)

for the scalable process development, as the mono-Boc route (Scheme 2B) produced a bis-alkylated impurity (24) via bis-adduct 23, which was inseparable from the desired product. The purging of 24 was unsuccessful by crystallization after global deprotection since the product (8a) and 24 have the same polarity characteristics [(24, analytical HPLC: retention time 6.89, 466 (m/z). Retention time for 8a (compound I-1) 6.64, 324 (m/z)].

For subsequent 5'-phosphorylation, compound 8a could be reprotected with a 2',3'-isopropylidene group to provide 26a, which was then phosphorylated (and subsequently deprotected) to yield high potency $P2Y_1R$ agonists, e.g. 27 and 28 (Scheme S5) (reference 6). Although our published method for the synthesis of 27 used benzoyl peroxide as oxidant in the phosphitylation reaction (reference 6), we found that use of $H_2O_2$ resulted in less undesired thioether oxidation. Alternatively, the trityl group and Boc protection of 22a were removed simultaneously using $ZnBr_2$ to yield 26a directly (reference 27).

Scheme S5.

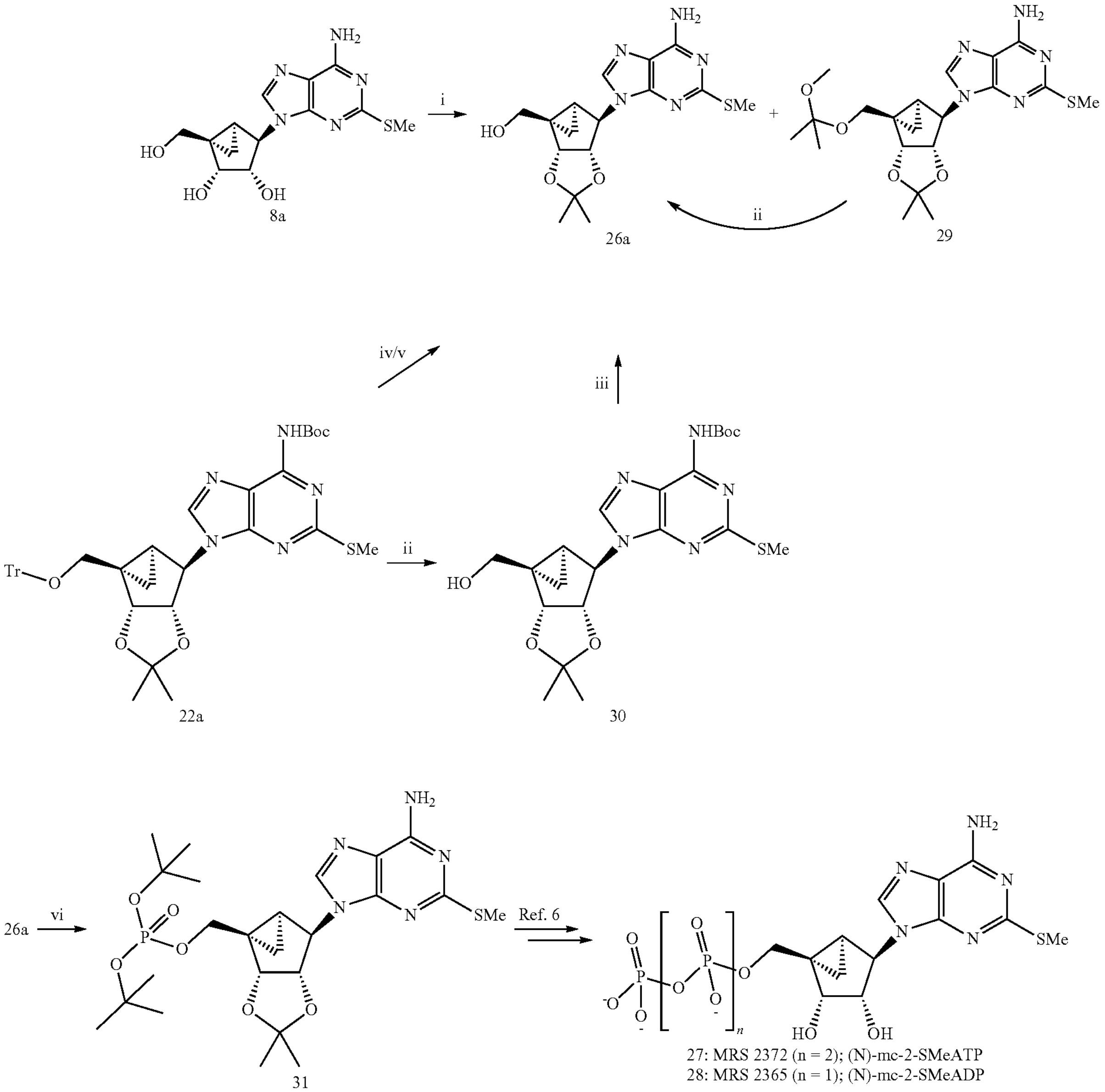

8a

26a

29

22a

30

26a

31

27: MRS 2372 (n = 2); (N)-mc-2-SMeATP
28: MRS 2365 (n = 1); (N)-mc-2-SMeADP

5'-Phosphorylation of (N)-methanocarba nucleoside 8a to yield previously characterized $P2Y_1R$ agonists 27 and 28 (see Reference 6). Reagents and conditions. (i) anhyd. acetone, 2,2-dimethoxypropane, p-TSA, rt, 18 h; (ii) anhyd. acetone, p-TSA, rt, 18 h, 58% over 2 steps for 29, 61% for 30; (iii) anhyd. acetone-TFA (1:1), rt, 3 h, 32%; (iv) anhyd. acetone-TFA (1:2), rt, 3 h, 56%; (v) anhyd. $CH_2Cl_2$, anhyd. $ZnBr_2$, 10-20 min, 41%; (vi) (a) THF, tetrazole, di-tert-butyl-N, N-diethyl-phosphoramidite, rt, 18h (b) 30% aq. $H_2O_2$, rt, 3 h, 81%.

TABLE 2

Synthesis Yields of $N^6$-Boc-adenine 2-thioethers 16a-16f and ether 16g and their conversion to protected (N)-methanocarba nucleosides by a Mitsunobu reaction with bicyclic intermediate 3.

| RX= | Compound # | Adenine precursor 16 (% yield, 1 step) | Protected adenine 20, 21 (% yield, 2 steps) | Protected nucleoside 22, 25 (% yield, 1 step) | Deprotected nucleoside 8 (% yield, 1 step) |
|---|---|---|---|---|---|
| $CH_3S$ (large scale) | I-1 | 16a (94)[a] (67)[b] | 20a (60)[e] (45)[g] | 22a (94) | 8a (59)[i] (88)[j] |
| $CH_3CH_2S$ | I-2 | 16b (99)[c] | 20b (58)[e] | 22b (84) | 8b (46)[k] |
| $CH_3(CH_2)_5S$ | I-3 | 16c (40)[c] | 20c (60)[e] | 22c (77) | 8c (56)[k] |
| cyclohexyl-S | I-4 | 16d (60)[c] | 21d (94)[f] | 25d (83) | 8d (70)[i] |
| $PhCH_2S$ | I-5 | 16e (80)[c] | 20e (79)[e] | 22e (95) | 8e (63)[k] |
| $Ph(CH_2)_2S$ | I-6 | 16f (87)[c] | 20f (28)[e], 20f (36)[g], 21f (23)[g] | 22f (78) | 8f (75)[k] |
| $CH_3O$ | I-7 | 16g (75)[d] | 20g (41)[g] | 22g (67) | 8g (45)[l] |

Footnotes correspond to the reaction conditions shown for Scheme 2.

The novel, convergent synthetic route described herein provided 520 g of 8a with an overall yield of 60% from compound 3 using Scheme 2B. An even better overall yield of 8300 was achieved on a laboratory scale. The outstanding advantage of the convergent route is that it spares the precious intermediate 3, which itself required nine steps from D-ribose to prepare. We calculate that the synthesis required 540 g of 3 per 100 g of 8a by the linear route compared to 230 g of 3 per 100 g of 8a for the convergent route. Thus, the molar ratio of the key precursor 3 in the convergent route was reduced by 5700 compared to the linear synthesis.

To test the generality of this approach to other 2-thioether substituents, 2-Cl-adenine (9) was treated with various alkyl thiols, aralkyl thiols, and their corresponding sodium salts to provide 2-thioethers of general formula 16b-16f (reference 22) (Scheme 2). The 2-thioethers were then mono-Boc-protected (20b-20f), as with 2-methylthioadenine, and subjected to a Mitsunobu reaction with the alcohol (3) to produce the desired products 22b-22f in excellent yields (Table 2). For the selective deprotection of tri-Boc intermediate (19a), we screened several conditions for the scale up process, and we found that basic conditions consisting of aq. sodium hydroxide (NaOH) in MeOH gave 20a in good yield. The yields varied with this combination for other examples (20f, 20g and 21d). For example, the yield of 20f with aq. NaOH in MeOH was 28%. Only the conditions using sodium bicarbonate or aq. ammonia, which resulted in satisfactory yields, are shown in Table 2. In the case of 8d, the isolation of pure product was difficult from the corresponding mono-Boc adduct 22d even by HPLC. However, we were able to obtain pure 8d via the di-Boc intermediate 25d (Scheme 2C).

Additionally, to evaluate the generality of our methodology, we prepared 2-methoxyadenine (16g), which was subjected to the same reaction sequence with similar results as the 2-thioethers (Scheme 2). A Mitsunobu reaction of 2-MeO-adenine (16g) with the alcohol 3 proceeded well in moderate yield (67%). It is noteworthy that we achieved improved yields using $N^6$-mono-Boc-adenine derivative 20. Without wishing to be bound by theory, it is believed that the activating/electron donating groups such as S-alkyl and O-alkyl likely increased the nucleophilic character of the purine nitrogen atoms to enhance yields. Thus, use of varied 2-alkyloxyadenine precursors instead of 2-alkylthio is expected to be suitable for this synthetic approach. 2-halo, 6-amino substituted adenines would also benefit from the convergent synthesis described above, since less of the expensive intermediate 3 would be needed to prepare the 2-halo substituted nucleoside final products.

Conclusions

We conclude that the most effective route to the desired nucleoside analogs is to install a 2-thioether or 2-ether group on the adenine precursor prior to $N^6$ protection and subsequent Mitsunobu coupling to the pseudoribose ((N)-methanocarba) moiety. Thus, we have identified a di-Boc-protected 2-methylthioadenine intermediate 21a that facilitates an efficient convergent synthetic route and is applicable to exploration of novel SAR of (N)-methanocarba derivatives at adenosine and P2Y receptors. This convergent synthesis of 2-substituted (N)-methanocarba-adenosines effectively increased the overall yield of the longest linear sequence compared to the previously reported linear synthesis. In particular, the quantity of the precious intermediate alcohol 3 needed for the convergent reaction scheme was reduced (by 57% for 8a), compared to the linear route. In order to optimize the convergent route, we compared various adenine amine protecting groups and found that M-di-Boc protection was the most versatile and provided the most easily purified intermediates. In summary, we have developed a facile convergent route, suitable for preclinical development, for the synthesis of (N)-methanocarba-nucleoside derivatives. These bicyclic nucleoside derivatives serve as purine receptor ligands with a pre-established receptor-preferred conformation and display efficacy in various disease models.

Chemical Synthesis:

2-Chloroadenine (9) was purchased from Ark Pharm (Arlington Heights, IL, USA). All other reagents were from Sigma-Aldrich (St. Louis, MO). $^1H$-NMR spectra were obtained with a Bruker 400 MHz spectrometer in in $CDCl_3$ (7.26 ppm), $CD_3OD$ (HOD=4.87 ppm) or in $(CD_3)_2SO$ ($^1H$=2.50 ppm and $^{13}C$=39.52 ppm). The chemical shifts are expressed as ppm downfield and coupling constants (J) are given in Hz. TLC analysis was carried out on glass sheets precoated with silica gel F254 (0.2 mm) from Aldrich. The purity of final nucleoside derivatives was checked using a Hewlett-Packard 1100 HPLC equipped with an Agilent Eclipse 5 μm XDB-C18 analytical column (50 mm×4.6 mm; Agilent Technologies Inc., Palo Alto, CA). Mobile phase: linear gradient solvent system, 10 mM TEAA (triethylammonium acetate):$CH_3CN$ from 95:5 to 0:100 in 20 min; the flow rate was 1.0 mL/min. Peaks were detected by UV absorption with a diode array detector at 230, 254, and 280 nm. All derivatives tested for biological activity showed >95% purity in the HPLC systems. Low-resolution mass spectrometry was performed with a JEOL SX102 spectrometer with 6 kV Xe atoms following desorption from a glycerol matrix or on an Agilent LC/MS 1100 MSD, with a Waters Atlantis C18 column (Milford, MA, USA). High resolution mass spectroscopic (HRMS) measurements were performed on a proteomics optimized Q-TOF-2 (Micromass-Waters) using external calibration with polyalanine, unless noted. Mass accuracies were observed.

General Procedure for the Synthesis of 2-Thiol Adenine Derivatives (16a-16f):

Procedure A: To a 75 ml cylindrical sealed tube equipped with a stir bar was added 2-chloroadenine (1.0 equiv.), sodium thiomethoxide (6.0 equiv.) and anhydrous DMF (20 ml, ~0.1 M). The reaction mixture was stirred at 110° C. for 12-16 h. The reaction was monitored by mass spectrometry and continued until starting material had disappeared. The solvent was removed under reduced pressure by rotary evaporation to obtain a solid which was dissolved in 6 N HCl (15 ml) and stirred at 60° C. for 2 h. The solution was cooled to 0° C. and slowly neutralized with aqueous ammonia (23%) until a pH of 8-9 was reached. A white solid appeared slowly and was filtered and dried under air to afford compound 16a. Data matched with the literature report (reference 26). $^1H$ NMR (400 MHz, DMSO-$d_6$) δ 12.76 (s, 1H), 7.97 (s, 1H), 7.18 (s, 2H), 2.44 (s, 3H). Yield: 67%; 3.80g of 16a from 5.30 g of 2-chloroadenine (9). Large scale yield for step 1 leading to 520 g 8a, using conditions (a) 94%; 500 g of 16a from 500 g of 2-chloroadenine (9).

Procedure B (see reference 22): In a 10 ml sealed tube, equipped with a stir bar was added 2-chloroadenine (1.0 equiv.), cesium carbonate (3.0-3.5 equiv.) and anhydrous DMF (~0.4 M). To this solution, the alkyl/aryl alkyl thiol (5.0-10.0 equiv.) was added, and the reaction mixture was stirred at 150° C. for one day. The reaction mixture was cooled to room temperature and diluted with water to get the product as a white precipitate, which was filtered off and dried under air. The product was used directly for the next step without any further purification.

Compounds 16b-16g were prepared by this method with slight modifications.

2-(Ethylthio)-9H-purin-6-amine, 16b: Compound 16b was prepared from 2-chloroadenine (510 mg, 3.0 mmol) (9) and 10.0 equiv. of ethanethiol in DMF. Yield: 99%; 580 mg. $^1H$ NMR (400 MHz, DMSO-$d_6$) δ 12.75 (s, 1H), 7.94 (s, 1H), 7.17 (s, 2H), 3.04 (q, J=7.3 Hz, 2H), 1.30 (t, J=7.3 Hz, 3H). $^{13}C$ NMR (100 MHz, DMSO-$d_6$) δ 164.38, 155.28, 152.65, 139.47, 115.54, 25.08, 15.43. HRMS (ESI) m/z: [M+H]+ calculated for $C_7H_{10}N_5{}^{32}S$: 196.0657. found 196.0655.

2-(Hexylthio)-9H-purin-6-amine, 16c: Compound 16c was prepared from 2-chloroadenine (0.34 g, 2.0 mmol) (9) and 5.0 equiv. of n-hexanethiol in DMF. Yield: 40%; 200 mg. $^1H$ NMR (400 MHz, DMSO-$d_6$) δ 12.65 (s, 1H), 7.96 (s, 1H), 7.15 (s, 2H), 3.05 (t, J=7.2 Hz, 2H), 1.63 (p, J=7.3 Hz, 2H), 1.39 (t, J=7.5 Hz, 2H), 1.33-1.13 (m, 4H), 0.92-0.76 (m, 3H). $^{13}C$ NMR (100 MHz, DMSO) δ 163.18, 154.87, 151.86, 138.22, 115.25, 30.85, 29.93, 29.07, 27.99, 22.00, 13.85. HRMS (ESI) m/z: [M+H]+ calculated for $C_{11}H_{17}N_5S$: 182.0930. found 182.0936.

2-(Cyclohexylthio)-9H-purin-6-amine, 16d: Compound 16d was prepared from 2-chloroadenine (0.34 g, 2.0 mmol) (9) and 6.0 equiv. of n-hexanethiol in DMF (~0.4 M). Yield: 60%; 298 mg. $^1H$ NMR (400 MHz, DMSO-$d_6$) δ 7.95 (s, 1H), 7.13 (s, 2H), 3.70 (h, J=4.4, 3.9 Hz, 1H), 2.05 (dd, J=9.9, 4.7 Hz, 2H), 1.70 (dt, J=10.0, 4.7 Hz, 2H), 1.58 (d, J=12.4 Hz, 1H), 1.39 (q, J=8.3, 6.4 Hz, 4H), 1.29-1.18 (m, 1H). $^{13}C$ NMR (100 MHz, DMSO) δ 162.94, 154.92, 151.96, 138.30, 115.33, 42.13, 32.84, 25.60, 25.29. HRMS (ESI) m/z: [M+H]+ calculated for $C_{11}H_{16}N_5{}^{32}S$. found 250.1128.

2-(Benzylthio)-9H-purin-6-amine, 16e: Compound 16e was prepared from 2-chloroadenine (510 mg, 3.0 mmol) (9) and 5.0 equiv. of benzyl mercaptan in DMF (~0.4 M). Yield: 80%; 620 mg. $^1H$ NMR (400 MHz, DMSO-$d_6$) δ 12.76 (s, 1H), 7.98 (s, 1H), 7.49-7.37 (m, 2H), 7.36-7.12 (m, 5H), 4.35 (s, 2H). $^{13}C$ NMR (100 MHz, DMSO) δ 162.69, 155.39, 150.91, 138.67, 137.91, 128.90, 128.27, 126.77, 116.37, 34.16. HRMS (ESI) m/z: [M+H]+ calculated for $C_{12}H_{12}N_5{}^{32}S$: 258.0813. found 258.0804.

2-(Phenethylthio)-9H-purin-6-amine, 16f: Compound 16f was prepared from 2-chloroadenine (510 mg, 3.0 mmol) (9) and 5.0 equiv. of 2-phenylethanethiol. Yield: 87%; 710 mg. $^1H$ NMR (400 MHz, DMSO-$d_6$) δ 7.98 (d, J=1.9 Hz, 1H), 7.31 (d, J=4.4 Hz, 4H), 7.21 (dt, J=8.0, 4.0 Hz, 3H), 3.29 (dd, J=9.2, 6.3 Hz, 2H), 2.96 (dd, J=9.1, 6.4 Hz, 2H). $^{13}C$ NMR (100 MHz, DMSO) δ 162.79, 155.00, 152.10, 140.72, 138.50, 128.61, 128.30, 126.15, 115.45, 35.40, 31.50. HRMS (ESI) m/z: [M+H]+ calculated for $C_{13}H_{14}N_5{}^{32}S$: 272.0970. found 272.0968.

2-Methoxy-9H-purin-6-amine, 16g: Compound 16g was prepared according to a published report (Reference 23). Yield: 75% (710 mg). $^1H$ NMR (400 MHz, DMSO-$d_6$) δ 12.57 (s, 1H), 7.90 (s, 1H), 7.10 (s, 2H), 3.78 (s, 3H). HRMS (ESI) m/z: [M+H]+ calculated for $C_6H_8N_5O$: 166.0729. found 166.0728.

General Procedure for the Synthesis of Mono-Boc-2-MeS-Adenine Derivatives tert-Butyl (2-(methylthio)-9H-purin-6-yl)carbamate, 20a: To a stirred solution of the 2-alkylthioadenine derivative 16a (1.0 g, 5.52 mmol, 1.0 equiv.) in THE (~0.1-0.2 M) was added $Boc_2O$ (4.82 g, 22.1 mmol, 4.0 equiv.) and DMAP (135 mg, 20 mol %, 0.2 equiv.) and the mixture was stirred overnight at room temperature. TLC showed a mixture of products [(di-Boc-2-MeS-adenine (21a) and tri-Boc-2-MeS-adenine (19)]. The solvent (THF) was removed under reduced pressure by rotary evaporation and water (50 ml) was added. The crude was extracted with ethyl acetate (EtOAc, 2×120 mL) and the organic layer washed with brine (20 ml). The organic layer (EtOAc) was separated, dried over $Na_2SO_4$, filtered and concentrated to afford the crude product (20a+21a), which was used directly for the next step without further purification. The obtained crude was dissolved in MeOH (30 ml) and saturated aq. $NaHCO_3$ was added (20 ml). The reaction mixture was stirred for 5 h at 60° C. The reaction mixture was cooled to room temp. and neutralized with 4N HCl or sat. sodium dihydrogen phosphate until the pH reached 7-7.5. Note: Work-up was done although there was some starting material (20a+21a) left in the reaction mixture. MeOH was removed by rotary evaporation, and the aq. solution was extracted with EtOAc (3×100 ml), washed with brine (20 ml), separated, dried over $Na_2SO_4$, filtered and concentrated to obtain the crude product. The product was purified by silica gel column chromatography to afford homogeneous mono-Boc-2-MeS-adenine (20a). Eluent: 30-50% EtOAc in hexane. Yield: 45%, ~0.70 g. $^1H$-NMR (400 MHz, chloroform-d) δ 11.31 (s, 1H), 8.19

(s, 1H), 7.75 (s, 1H), 2.62 (s, 3H), 1.54 (s, 9H). $^{13}$C NMR (100 MHz, DMSO) δ 162.79, 155.00, 152.10, 140.72, 138.50, 128.61, 128.30, 126.15, 115.45, 35.40, 31.50. ESMS calculated for $C_{22}H_{24}N_5O_7$: (M+H) 470.2, found 470.2.

Large scale yield for step 3 leading to 520 g 8a, using conditions: (e) 60%, 190 g of 20a from 526 g of 19.

For compounds 20b-20g, 0.560-1.17 mmol of the 16b-16g was used; all other amounts were as given for the preparation of 8a.

tert-Butyl (2-(ethylthio)-9H-purin-6-yl)carbamate, 20b: Compound 20b was prepared from compound 16b (1.0 mmol) using the conditions [e] (i), and (ii) aq. 10% NaOH in MeOH (1:1, ~0.2 M) under room temperature for 5 h. Yield: 58%; 170 mg. $^1$H NMR (400 MHz, chloroform-d) δ 8.30 (s, 1H), 8.27 (s, 1H), 3.15 (q, J=7.4 Hz, 2H), 1.46 (s, 9H), 1.32 (t, J=7.3 Hz, 4H). $^{13}$C NMR (100 MHz, Chloroform-d) δ 164.55, 162.42, 152.63, 144.34, 143.74, 109.95, 83.24, 28.03, 25.26, 14.56. HRMS (ESI) m/z: [M+H]+ calculated for $C_{12}H_8N_5O_2{}^{32}S$: 296.1185. found 296.1181.

tert-Butyl (2-(hexylthio)-9H-purin-6-yl)carbamate, 20c: Compound 20c was prepared from compound 16c (0.621 mmol). Yield: 60%; 130 mg. $^1$H NMR (400 MHz, chloroform-d) δ 8.22 (s, 1H), 8.03 (s, 1H), 3.20 (t, J=7.3 Hz, 2H), 1.70 (q, J=7.4 Hz, 2H), 1.50 (s, 9H), 1.41 (t, J=7.8 Hz, 2H), 1.31-1.19 (m, 4H), 0.84 (t, J=8.0 Hz, 3H). $^{13}$C NMR (100 MHz, chloroform-d) δ 164.96, 163.26, 152.81, 143.70, 143.56, 109.35, 83.66, 31.51, 31.12, 29.25, 28.69, 28.13, 22.62, 14.09. ESMS calculated for $C_{16}H_{25}N_5O_2S$: (M+H) 352.2. found 352.2.

tert-Butyl (tert-butoxycarbonyl)(2-(cyclohexylthio)-9H-purin-6-yl)carbamate, 21d: Compound 21d was prepared from 16d (0.401 mmol) using the conditions [f] (i), and (ii) aq. $NH_4OH$ (23%) in MeOH (1:1, −0.2 M) at 60° C. for 6 h. Yield: 94%; 170 mg. $^1$H NMR (400 MHz, chloroform-d) δ 11.33 (s, 1H), 8.37 (s, 1H), 3.95-3.75 (m, 1H), 2.13-2.08 (m, 2H), 1.75-1.70 (m, 2H), 1.59-1.50 (m, 1H), 1.50-1.34 (m, 22H), 1.28-1.21 (m, 1H). $^{13}$C NMR (100 MHz, chloroform-d) δ 164.79, 157.62, 150.07, 147.32, 143.27, 119.86, 84.42, 43.74, 32.90, 27.73, 25.92, 25.70. ESMS calculated for $C_{21}H_{32}N_5O_4S$: (M+H) 450.2. found 450.3.

tert-Butyl (2-(benzylthio)-9H-purin-6-yl)carbamate, 20e: Compound 20e was prepared from 16e (1.166 mmol). Yield: 79%; 423 mg. $^1$H NMR (400 MHz, chloroform-d) δ 8.35 (s, 1H), 8.11 (s, 1H), 7.48-7.27 (m, 5H), 4.66 (s, 2H), 1.68 (d, J=1.3 Hz, 9H). $^{13}$C NMR (100 MHz, chloroform-d) δ 164.44, 161.95, 152.63, 144.20, 143.49, 137.71, 129.30, 128.57, 127.24, 109.67, 84.00, 35.65, 28.17. HRMS (ESI) m/z: [M+H]+ calculated for $C_{17}H_{20}N_5O_2S$: 358.1338. found 357.1340.

tert-Butyl (2-(phenethylthio)-9H-purin-6-yl)carbamate, 20f: Compound 20f was prepared from 16f (0.560 mmol). Yield: 28%; 58 mg. Using the conditions [g], yield of 20f: 36%; 170 mg. $^1$H NMR (400 MHz, chloroform-d) δ 8.23 (s, 1H), 7.34-7.25 (m, 4H), 7.21 (tt, J=5.2, 3.4 Hz, 1H), 3.53-3.44 (m, 2H), 3.13-3.04 (m, 2H), 1.56 (s, 9H). $^{13}$C NMR (100 MHz, chloroform-d) δ 164.44, 162.67, 152.71, 144.03, 143.57, 140.72, 128.89, 128.53, 126.42, 109.67, 83.91, 35.86, 32.55, 28.19. HRMS (ESI) m/z: [M+H]+ calculated for $C_{18}H_{22}N_5O_2{}^{32}S$: 372.1494. found 372.1490.

tert-Butyl (2-methoxy-9H-purin-6-yl)carbamate, 20g: Compound 20g was prepared from 16g (1.211 mmol). Yield: 41%; 132 mg. $^1$H NMR (400 MHz, DMSO-$d_6$) δ 11.89 (s, 1H), 10.57 (s, 1H), 8.24 (s, 1H), 3.87 (s, 3H), 1.51 (s, 9H). $^{13}$C NMR (100 MHz, DMSO) δ 163.94, 161.94, 160.95, 152.76, 145.66, 108.73, 81.33, 54.25, 27.91. HRMS (ESI) m/z: [M+H]+ calculated for $C_{11}H_{15}N_5O_2H^+$: 266.1253. found 266.1252.

Mitsunobu reaction of 20a-20c, 20e-20g, and 21d with 5'-O-trityl bicyclic intermediate 3; Typical Procedure for 22a-22c, 22e-22g, and 25d: In a 25 ml round bottom flask, mono-Boc-2-MeS-adenine (20a) (300 mg, 1.07 mmol, 1.5 equiv.), alcohol 3 (315 mg, 0.711 mmol, 1.0 equiv.), and triphenylphosphine ($PPh_3$) [373 mg, 1.42 mmol, 2.0 equiv.] were added. The contents were co-evaporated with dry toluene (3×5 ml) and the residue dried under vacuum for 3 h. The mixture was dissolved in dry THE (10 ml) and DIAD (280 μl, 1.42 mmol, 2.0 equiv.) was added dropwise via syringe at room temperature under nitrogen atmosphere. The reaction mixture was stirred for 1-2 h at room temperature and monitored by TLC. The solvent (THF) was removed under reduced pressure by rotary evaporation, and the crude product was purified by silica gel column chromatography to afford the product (22a) along with di-(isopropyloxycarbonyl)hydrazine by-product (DIAD-$H_2$) [UV inactive; ~13% based on the C—H proton (septet) integration of isopropoxy group by $^1$H-NMR], which could be observed as a yellow spot after developing the TLC with p-anisaldehyde stain. Eluent: 15-30% EtOAc in hexane. TLC: $R_f$~0.3 (30% EtOAc in hexane). Corrected yield by $^1$H-NMR: 94%, ~470 mg. Purity: ~87% by $^1$H-NMR.

Large scale yield for step 4 leading to 520 g 8a: 1.8 kg, crude product was obtained as a foamy solid from 20a (769 g, 2.73 mol, 1.10 eq) and compound 3 (1.10 kg, 2.49 mol, 1.00 eq). $^1$H NMR (400 MHz, chloroform-d) δ 8.14 (s, 1H), 7.81-7.70 (m, 1H) 7.78 (s, 1H), 7.43-7.37 (m, 6H), 7.33-7.13 (m, 9H), 5.38-5.29 (m, 1H), 5.07 (d, J=3.2 Hz, 1H), 4.63 (dd, J=7.2, 1.6 Hz, 1H), 3.76 (d, J=10.0 Hz, 1H), 3.04 (d, J=10.0 Hz, 1H), 2.56 (s, 3H), 1.55 (s, 9H), 1.53 (s, 3H), 1.25 (s, 4H), 1.16 (t, J=5.0 Hz, 1H), 0.94-0.85 (m, 1H). $^{13}$C NMR (100 MHz, chloroform-d) δ 166.67, 151.72, 149.75, 149.28, 143.84, 139.86, 128.76, 128.06, 127.29, 119.27, 112.49, 88.85, 87.01, 82.17, 81.81, 64.82, 59.02, 37.39, 30.71, 28.33, 27.91, 26.09, 24.47, 22.08, 21.97, 14.86, 13.19. ESMS (ESI) m/z: [M+H]+ calculated for $C_{40}H_{44}N_5O_5S$: 706.3. found 706.3.

Compounds 22a-22c, 22e-22g, and 25d:

tert-Butyl (9-((3aR,3bR,4aS,5R,5aS)-2,2-dimethyl-3b-((trityloxy)methyl)hexahydrocyclopropa[3,4]cyclopenta[1,2-d][1,3]dioxol-5-yl)-2-(ethylthio)-9H-purin-6-yl)carbamate, 22b: Compound 22b was prepared from 20b (0.190 mmol). Corrected yield: 84%; 119 mg. $^1$H NMR (400 MHz, chloroform-d) δ 8.12 (s, 1H), 7.77 (s, 1H), 7.38 (m, 6H), 7.23 (m, 9H), 5.29 (d, J=6.9 Hz, 1H), 5.04 (d, J=3.6 Hz, 1H), 4.60 (d, J=7.0 Hz, 1H), 3.73 (dd, J=10.2, 3.5 Hz, 1H), 3.14 (ddd, J=14.0, 8.8, 5.2 Hz, 2H), 3.03 (dd, J=10.2, 3.4 Hz, 1H), 1.53 (s, 9H), 1.50 (s, 3H), 1.36 (t, J=7.3 Hz, 3H), 1.23 (m, 4H), 1.14 (m, 1H), 0.91-0.86 (m, 1H). Product was contaminated with hydrazine impurity (~9%). $^{13}$C NMR (100 MHz, chloroform-d) δ 166.27, 151.69, 149.68, 149.28, 143.81, 139.66, 128.71, 128.00, 127.24, 119.12, 112.42, 88.78, 86.98, 82.08, 81.75, 64.82, 59.00, 37.32, 30.54, 28.27, 26.04, 25.76, 24.40, 14.52, 13.15. HRMS (ESI) m/z: [M+H]+ calculated for $C_{41}H_{46}N_5O_5{}^{32}S$: 720.3220. found 720.3212.

tert-butyl (9-((3aR,3bR,4aS,5R,5aS)-2,2-dimethyl-3b-((trityloxy)methyl)hexahydrocyclopropa[3,4]cyclopenta[1,2-d][1,3]dioxol-5-yl)-2-(hexylthio)-9H-purin-6-yl)carbamate, 22c: Compound 22c was prepared from 20c (0.237 mmol). Corrected yield: 77%; 142 mg. $^1$H NMR (400 MHz, chloroform-d) δ 8.16 (s, 1H), 7.88 (s, 1H), 7.44-7.42 (m, 6H), 7.35-7.21 (m, 9H), 5.35-5.33 (m, 1H), 5.08 (s, 1H), 4.63 (dd, J=7.1, 1.5 Hz, 1H), 3.79 (d, J=10.0 Hz, 1H), 3.25-3.12 (m, 2H), 3.06 (d, J=10.0 Hz, 1H), 1.56 (s, 9H), 1.54 (s, 4H), 1.48-1.45 (m, 2H), 1.33 (q, J=3.7 Hz, 4H), 1.28

(s, 2H), 1.26 (s, 3H), 1.18 (t, J=5.0 Hz, 1H), 0.92-0.89 (m, 4H). Product was contaminated with hydrazine impurity (~26%). $^{13}$C NMR (100 MHz, chloroform-d) δ 166.35, 151.68, 149.66, 149.26, 143.76, 139.62, 128.66, 127.96, 127.18, 119.23, 112.35, 88.74, 86.93, 81.92, 81.65, 64.78, 58.83, 37.26, 31.50, 31.44, 30.50, 29.36, 28.66, 28.22, 25.98, 24.36, 22.64, 21.98, 14.11, 13.08. ESMS calculated for calculated for $C_{45}H_{53}N_5O_5S$: 775.4. found 775.4.

tert-Butyl (2-(cyclohexylthio)-9-((3aR,3bR,4aS,5R,5aS)-2,2-dimethyl-3b-((trityloxy)methyl)hexahydrocyclopropa[3,4]cyclopenta[1,2-d][1,3]dioxol-5-yl)-9H-purin-6-yl)carbamate, 22d: Compound 25d was prepared from 21d (0.293 mmol). Corrected yield: 83%; 212 mg. $^1$H NMR (400 MHz, chloroform-d) δ 8.24 (s, 1H), 7.44-7.32 (m, 5H), 7.28-7.10 (m, 10H), 5.29 (d, J=7.0 Hz, 1H), 5.04 (s, 1H), 4.60 (dd, J=7.1, 1.5 Hz, 1H), 3.78 (dd, J=10.1, 7.0 Hz, 2H), 3.04 (d, J=10.0 Hz, 1H), 2.10-2.07 (m, 2H), 1.77-1.67 (m, 2H), 1.61 (m, 1H), 1.51 (s, 4H), 1.45 (s, 22H), 1.26-1.17 (m, 4H), 1.17-1.11 (m, 1H), 0.90-0.86 (m, 1H). Product was contaminated with hydrazine impurity (~10%). $^{13}$C NMR (100 MHz, chloroform-d) δ 165.35, 153.49, 150.56, 150.01, 143.77, 141.85, 128.65, 127.94, 127.15, 125.73, 112.32, 88.66, 86.97, 83.64, 81.73, 64.66, 59.11, 43.88, 37.34, 32.94, 32.88, 30.26, 27.86, 25.97, 24.33, 21.74, 14.14, 12.96, 10.93. ESMS calculated for $C_{50}H_{60}N_5O_7S$: 874.4. found 874.5.

tert-Butyl (2-(benzylthio)-9-((3aR,3bR,4aS,5R,5aS)-2,2-dimethyl-3b-((trityloxy)methyl)hexahydrocyclopropa[3,4]cyclopenta[1,2-d][1,3]dioxol-5-yl)-9H-purin-6-yl)carbamate, 22e: Compound 22e was prepared from 20e (0.280 mmol). Corrected yield: 95%; 172 mg. $^1$H NMR (400 MHz, chloroform-d) δ 8.18 (s, 1H), 7.85 (s, 1H), 7.50-7.45 (m, 2H), 7.43-7.36 (m, 6H), 7.33-7.19 (m, 13H), 5.31 (d, J=7.1 Hz, 1H), 5.10 (s, 1H), 4.60 (d, J=7.1 Hz, 1H), 4.45 (s, 2H), 3.80 (d, J=10.2 Hz, 1H), 3.04 (d, J=10.1 Hz, 1H), 1.57 (s, 9H), 1.54 (s, 3H), 1.29-1.25 (m, 4H), 1.18 (t, J=5.1 Hz, 1H), 0.94-0.87 (m, 1H). Product was contaminated with hydrazine impurity (~10%). $^{13}$C NMR (100 MHz, chloroform-d) δ 165.56, 151.61, 149.66, 149.28, 143.79, 139.76, 138.22, 129.36, 128.68, 128.32, 127.97, 127.91, 127.20, 126.95, 119.35, 112.39, 88.82, 86.95, 82.08, 81.73, 64.82, 59.04, 37.33, 35.85, 30.49, 28.23, 26.02, 24.41, 21.99, 13.11. HRMS (ESI) m/z: [M+H]+ calculated for $C_{46}H_{48}N_5O_5{}^{32}S$: 782.3376. found 782.3384.

tert-Butyl (9-((3aR,3bR,4aS,5R,5aS)-2,2-dimethyl-3b-((trityloxy)methyl)hexahydrocyclopropa[3,4]cyclopenta[1,2-d][1,3]dioxol-5-yl)-2-(phenethylthio)-9H-purin-6-yl)carbamate, 22f: Compound 22f was prepared from 20f (0.431 mmol). Corrected yield: 78%; 160 mg. $^1$H NMR (400 MHz, chloroform-d) δ 8.19 (d, J=1.4 Hz, 1H), 7.77 (s, 1H), 7.43-7.41 (m, 5H), 7.38-7.36 (m, 2H), 7.31-7.21 (m, 13H), 5.33 (d, J=7.1 Hz, 1H), 5.14 (s, 1H), 4.61-4.59 (m, 1H), 3.83 (d, J=10.1 Hz, 1H), 3.40 (qt, J=13.6, 6.6 Hz, 2H), 3.07 (t, J=7.9 Hz, 2H), 3.00 (d, J=10.1 Hz, 1H), 1.57 (s, 9H), 1.54 (s, 3H), 1.33 (d, J=6.3 Hz, 1H), 1.23 (s, 3H), 1.19 (t, J=5.1 Hz, 1H), 0.89 (dd, J=9.4, 5.7 Hz, 1H). Product was contaminated with hydrazine impurity (~38%). $^{13}$C NMR (100 MHz, chloroform-d) δ 165.90, 151.67, 149.57, 149.38, 143.77, 140.94, 139.54, 128.91, 128.67, 128.37, 127.97, 127.20, 126.24, 112.38, 88.82, 86.98, 81.94, 81.55, 64.85, 58.75, 37.32, 36.37, 32.92, 30.42, 28.22, 26.01, 24.37, 13.14. HRMS (ESI) m/z: [M+H]+ calculated for $C_{47}H_{50}N_5O_5{}^{32}S$: 796.3533. found 796.3527.

tert-Butyl (9-((3aR,3bR,4aS,5R,5aS)-2,2-dimethyl-3b-((trityloxy)methyl)hexahydrocyclopropa[3,4]cyclopenta[1,2-d][1,3]dioxol-5-yl)-2-methoxy-9H-purin-6-yl)carbamate, 22g: Compound 22g was prepared from 20g (0.431 mmol). Corrected yield: 67%; 135 mg with 80% purity by $^1$H-NMR. $^1$H NMR (400 MHz, chloroform-d) δ 8.08 (s, 1H), 7.87 (s, 1H), 7.44-7.35 (m, 5H), 7.31-7.17 (m, 10H), 5.33 (d, J=7.1 Hz, 1H), 5.02 (s, 1H), 4.66 (dd, J=7.3, 1.5 Hz, 1H), 3.91 (s, 3H), 3.74 (d, J=9.9 Hz, 1H), 3.07 (d, J=9.9 Hz, 1H), 1.55 (s, 9H), 1.53 (s, 3H), 1.27 (s, 1H), 1.25 (s, 3H), 1.16 (t, J=5.0 Hz, 1H), 0.96-0.90 (m, 1H). Product was contaminated with hydrazine impurity (~12%). $^{13}$C NMR (100 MHz, chloroform-d) δ 162.29, 152.35, 150.88, 149.50, 143.80, 139.51, 128.69, 127.97, 127.23, 117.82, 112.40, 88.80, 86.91, 82.05, 81.91, 64.75, 59.16, 55.06, 37.34, 30.54, 28.23, 26.05, 24.40, 13.15. HRMS (ESI) m/z: [M+H]+ calculated for $C_{40}H_{44}N_5O_6$: 690.3292. found 690.3297.

Compounds 8a-8f:

Conditions (j): 1.0 N HCl (5.0 ml) was added to a sealed tube containing the compound (22a) (70 mg, 0.1 mmol). The solution was stirred at 50° C. for 18 h. The solvent was removed, and the crude was co-evaporated with toluene (2×5 ml). The residue was dissolved in MeOH (5.0 ml) and treated with 1 ml of Amberlite resin-93 (1.2 mmol), which was previously washed with MeOH (3×3 ml). The reaction mixture was stirred for 16 h. The MeOH solution was filtered, concentrated, and the crude was purified by silica gel column chromatography to get 8a. Eluent: 5% of 10% aq. $NH_4OH$ (23%) in MeOH, then 5-15% MeOH in DCM. Yield: 32 mg, 88%.

Large scale yield for step 5 leading to 520 g 8a, using conditions (i). Six individual runs (each with 315 g of 22a, 446 mmol, 1.00 eq.) were carried out to get a combined 520 g of 8a as a white solid, 1.61 mol, 59.7% yield for 2 steps.

(1R,2R,3S,4R,5S)-4-(6-Amino-2-(methylthio)-9H-purin-9-yl)-1-(hydroxymethyl)bicyclo[3.1.0]hexane-2,3-diol, 8a. $^1$H NMR (400 MHz, methanol-$d_4$) δ 8.44 (s, 1H), 4.77 (dd, J=6.7, 1.6 Hz, 1H), 4.26 (d, J=11.7 Hz, 1H), 3.93-3.85 (m, 1H), 3.35 (d, J=9.5 Hz, 2H), 2.59 (s, 3H), 1.61 (dd, J=8.6, 3.8 Hz, 1H), 1.54 (dd, J=5.2, 3.9 Hz, 1H), 0.76 (ddd, J=8.7, 5.3, 1.7 Hz, 1H). $^{13}$C NMR (100 MHz, DMSO-$d_6$). HRMS (ESI) m/z: [M+H]+ calculated for $C_8H_{11}N_3O_2H^+$: 182.0930. found 182.0936.

Compounds 8b-8f were prepared using various acidic conditions.

(1R,2R,3S,4R,5S)-4-(6-Amino-2-(ethylthio)-9H-purin-9-yl)-1-(hydroxymethyl)bicyclo[3.1.0]hexane-2,3-diol, 8b: Compound 8b was prepared from 22b (30 mg, 0.042 mmol) using the conditions [k]. Yield: 46%; 6.0 mg. $^1$H NMR (600 MHz, methanol-$d_4$) δ 8.39 (s, 1H), 4.83 (s, 1H), 4.74 (dd, J=6.8, 1.7 Hz, 1H), 4.24 (d, J=11.6 Hz, 1H), 3.87 (dt, J=6.7, 1.4 Hz, 1H), 3.31 (d, J=11.7 Hz, 1H), 3.24-3.10 (m, 2H), 1.60 (ddd, J=8.8, 3.9, 1.5 Hz, 1H), 1.53 (dd, J=5.2, 4.0 Hz, 1H), 1.38 (t, J=7.3 Hz, 3H), 0.74 (ddd, J=8.7, 5.2, 1.7 Hz, 1H). $^{13}$C NMR (151 MHz, methanol-$d_4$) δ 166.68, 156.78, 151.34, 139.72, 117.57, 77.75, 72.20, 64.43, 62.94, 37.82, 26.22, 24.54, 15.28, 12.30. HRMS (ESI) m/z: [M+H]+ calculated for $C_{14}H_{20}N_5O_3{}^{32}S$: 338.1287. found 338.1293.

(1R,2R,3S,4R,5S)-4-(6-Amino-2-(hexylthio)-9H-purin-9-yl)-1-(hydroxymethyl)bicyclo[3.1.0]hexane-2,3-diol, 8c: Compound 8c was prepared from 22c (28 mg, 0.431 mmol) using the conditions [k]. Yield: 56%; 8.0 mg. $^1$H NMR (400 MHz, methanol-$d_4$) δ 8.39 (s, 1H), 4.85 (s, 1H), 4.76 (d, J=6.7 Hz, 1H), 4.25 (d, J=11.6 Hz, 1H), 3.89 (d, J=6.6 Hz, 1H), 3.36-3.28 (m, 1H), 3.25 (dt, J=14.1, 7.3 Hz, 1H), 3.13 (dt, J=13.6, 7.3 Hz, 1H), 1.75 (p, J=7.2 Hz, 2H), 1.61 (dd, J=9.0, 3.9 Hz, 1H), 1.54 (t, J=4.7 Hz, 1H), 1.53-1.41 (m, 2H), 1.36 (h, J=4.0 Hz, 4H), 0.97-0.89 (m, 3H), 0.79-0.71 (m, 1H). Compound was purified by HPLC and was contaminated with triethylammonium acetate buffer (~17% based on $NCH_2$ protons of the buffer). Prep. HPLC method:

Phenomenex Luna 5 m C18(2) 100 A, LC Column (250×21.2 mm). Linear gradient solvent system: ACN: 10 mM TEAA from 40:80 to 80:20 in 40 minutes. Rt~43.32 min. $^{13}C$ NMR (100 MHz, methanol-$d_4$) δ 157.36, 147.25, 141.87, 130.23, 108.12, 68.35, 62.77, 54.98, 53.48, 28.39, 23.15, 22.49, 21.29, 20.20, 15.15, 14.19, 4.90, 2.83. HRMS (ESI) m/z: [M+H]+ calculated for $C_{18}H_{26}N_5O_3{}^{32}S$: 394.1913. found 394.1920.

(1R,2R,3S,4R,5S)-4-(6-Amino-2-(cyclohexylthio)-9H-purin-9-yl)-1-(hydroxymethyl)bicyclo[3.1.0]hexane-2,3-diol, 8d: Compound 8d was prepared from 25d (96 mg, 0.1098 mmol) using the conditions [i]. Yield: 70%; 30.0 mg. $^1H$ NMR (400 MHz, methanol-$d_4$) δ 8.39 (s, 1H), 4.81 (s, 1H), 4.75 (dd, J=6.7, 1.6 Hz, 1H), 4.25 (d, J=11.6 Hz, 1H), 3.89 (d, J=6.8 Hz, 2H), 3.36-3.27 (m, 1H), 2.16-2.10 (m, 2H), 1.81-1.78 (m, 2H), 1.68-1.58 (m, 2H), 1.54-1.47 (m, 5H), 1.36-1.27 (m, 2H), 0.75 (ddd, J=8.8, 5.1, 1.7 Hz, 1H). $^{13}C$ NMR (100 MHz, methanol-$d_4$) δ 166.58, 156.78, 151.31, 139.72, 117.58, 77.79, 72.24, 64.47, 63.05, 44.73, 37.86, 34.50, 34.22, 27.16, 27.11, 26.97, 24.55, 12.32. ESMS calculated for $C_{18}H_{26}N_5O_3S$: 392.2. found 392.2.

(1R,2R,3S,4R,5S)-4-(6-Amino-2-(benzylthio)-9H-purin-9-yl)-1-(hydroxymethyl)bicyclo[3.1.0]hexane-2,3-diol, 8e: Compound 8e was prepared from 22e (89 mg, 0.1184 mmol) using the conditions [k]. Yield: 63%; 30.0 mg. $^1H$ NMR (600 MHz, methanol-$d_4$) δ 8.40 (s, 1H), 7.47-7.39 (m, 2H), 7.26 (t, J=7.7 Hz, 2H), 7.19-7.14 (m, 1H), 4.74 (dd, J=6.6, 1.7 Hz, 1H), 4.49-4.34 (m, 2H), 4.23 (d, J=11.6 Hz, 1H), 3.88 (dt, J=6.5, 1.4 Hz, 1H), 3.29 (d, J=11.7 Hz, 1H), 1.59 (ddd, J=8.8, 3.9, 1.5 Hz, 1H), 1.54 (dd, J=5.2, 3.9 Hz, 1H), 0.74 (ddd, J=8.7, 5.2, 1.7 Hz, 1H). $^{13}C$ NMR (151 MHz, methanol-$d_4$) δ 166.14, 156.73, 151.27, 139.90, 139.75, 130.19, 129.35, 127.95, 117.67, 77.76, 72.18, 64.40, 62.89, 37.80, 36.33, 24.56, 12.33. HRMS (ESI) m/z: [M+H]+ calculated for $C_8H_{11}N_3O_2H^+$: 182.0930. found 182.0936.

(1R,2R,3S,4R,5S)-4-(6-Amino-2-(phenethylthio)-9H-purin-9-yl)-1-(hydroxymethyl)bicyclo[3.1.0]hexane-2,3-diol, 8f: Compound 8f was prepared from 22f (92 mg, 0.116 mmol) using the conditions [k]. Yield: 75%; 36.0 mg. $^1H$ NMR (500 MHz, methanol-$d_4$) δ 8.38 (s, 1H), 7.30-7.28 (m, 2H), 7.25-7.22 (m, 2H), 7.15-7.12 (m, 1H), 4.73 (dd, J=6.6, 1.6 Hz, 1H), 4.23 (d, J=11.6 Hz, 1H), 3.86 (d, J=6.6 Hz, 1H), 3.39 (ddd, J=13.3, 8.7, 7.0 Hz, 1H), 3.33-3.22 (m, 2H), 3.00 (t, J=7.3 Hz, 2H), 1.58 (ddd, J=8.7, 3.9, 1.4 Hz, 1H), 1.54-1.52 (m, 1H), 0.72 (ddd, J=8.6, 5.1, 1.7 Hz, 1H). $^{13}C$ NMR (126 MHz, methanol-$d_4$) δ 166.41, 156.74, 151.30, 142.11, 139.62, 129.85, 129.39, 127.22, 77.74, 72.18, 64.38, 62.81, 37.81, 37.38, 33.60, 24.64, 12.30. HRMS (ESI) m/z: [M+H]+ calculated for $C_{20}H_{24}N_5O_3{}^{32}S$: 414.1600. found 414.1607.

(1R,2R,3S,4R,5S)-4-(6-Amino-2-methoxy-9H-purin-9-yl)-1-(hydroxymethyl)bicyclo[3.1.0]hexane-2,3-diol, 8g: Compound 8g was prepared from 22g (25 mg, 0.0362 mmol) using the conditions [1]. Yield: 45%; 5.0 mg. $^1H$ NMR (400 MHz, chloroform-d) δ 8.32 (d, J=5.8 Hz, 1H), 4.82-4.71 (m, 2H), 4.25 (dd, J=11.8, 5.6 Hz, 1H), 3.96 (dd, J=4.9, 2.7 Hz, 3H), 3.89 (d, J=6.3 Hz, 1H), 3.30 (dd, J=11.5, 5.5 Hz, 1H), 1.60 (p, J=4.4 Hz, 1H), 1.51 (p, J=4.7, 4.0 Hz, 1H), 0.80-0.68 (m, 1H). $^{13}C$ NMR (100 MHz, methanol-$d_4$) δ 163.78, 158.14, 152.21, 139.68, 116.31, 77.82, 72.24, 64.48, 63.28, 55.18, 37.93, 24.57, 12.22. HRMS (ESI) m/z: [M+H]+ calculated for $C_{13}H_{18}N_5O_4$: 308.1359. found 308.1353.

Synthesis of Nucleotide Derivatives 27 and 28:

Synthesis of 26a was realized under various conditions. (N)-methanocarba-2-SMe-adenosine, when reacted with 2,2-dimethoxypropane in acetone in the presence of p-TSA, gave a mixture of compounds 26a and 29. Whereas a reaction without dimethoxypropane removed the 5'-methoxypropane group, to furnish 26a, the same condition on 22a deprotected the trityl but not Boc-group to render 30, while under strongly acidic conditions of (1:1) acetone-TFA gave 26a. Similarly, use of analogues protocol directly on 22a gave 26a in a comparably moderate yield of 56%. Alternatively, reacting compound 22a with anhydrous $ZnBr_2$ removed both trityl and Boc protecting groups to give 26a in 41% yield (Reference 27). However, a longer reaction time (ca. 2 h, in this case) removed 2',3'-O-isopropylidene as well to give 8a in 22% yield. It is to be noted that since the reaction was performed in dichloromethane, most products separated out as the zinc salt, and the TLC/HPLC analysis mislead the progress of the reaction, and the reaction seems to be practically completed after 10-20 min (depending on the water content in the reaction mixture).

(N)-methanocarba-2-SMe-adenosine nucleotides were synthesized as reported earlier (Reference 6). The drawback of this method is the use of m-CPBA as an oxidizer in preparing 5'-di-tert-butylphosphate ester 31, which also gave 2-methylsulfoxide by-product in equal or sometimes in major amounts. An effort to improve the method by a direct phosphorylation of 26a using phosphorous oxychloride was not successful. However, employing hydrogen peroxide to oxidize the 5'-phosphoramidite intermediate limited the oxidation to phosphorous, giving the required compound as the sole product [Note: When the next deprotection reaction was carried out without purification (only workup), sulfoxide product was observed, implying, the increased reactivity of any residual hydrogen peroxide towards thio-alkanes in the presence of acid]. Deprotection of t-butyl and isopropylidene groups using aq. TFA (Reference 6) or DOWEX-H+ (Reference 28), followed by coupling with phosphate/pyrophosphate gave the desired products 27 and 28 (Reference 27).

(N)-methanocarba-2',3'-O-isopropylidene-2-thiomethyl-adenosine (26a) (see Reference 6):

Method 1: To a suspension of compound 8a (20 mg, 0.062 mmol) in a mixture (1:1) of anhyd. acetone and 2,2-dimethoxypropane (1.0 mL) were added p-toluenesulfonic acid (p-TSA hydrate, 12 mg, 0.062 mmol) and stirred at room temperature for 18 h. The volatile materials were removed by rotary evaporation under reduced pressure. The residue was partitioned between aq. $NaHCO_3$ and 5% i-PrOH in $CH_2Cl_2$. The organic layer was separated and dried over anhydrous $Na_2SO_4$. Rotary evaporation under vacuum gave a mixture of compounds 26a and 29 (TLC eluent, 5% MeOH in $CH_2Cl_2$; Compound 26a; $R_f$=0.25, ESI-MS $[M+H]^+$ for $C_{16}H_{21}N_5O_3S$ calculated, 364.1438. found, 364.2; Compound 29, $R_f$=0.60, ESI-MS $[M+H]^+$ for $C_{20}H_{29}N_5O_4S$ calculated, 436.2013. found, 436.2). the compound mixture 2 and 3 was dissolved in anhydrous acetone (2.0 mL), to this was added p-TSA hydrate (12 mg, 0.062 mmol) and stirred overnight (18 h). After a work-up as mentioned above, followed by the purification by silica gel chromatography gave 26a as a white foam (13 mg, 58%).

Method 2: To a flask containing compound 30 (80 mg, 0.173 mmol) was added a 1:1 mixture of anhyd. acetone-trifluoroacetic acid (2 mL) and stirred at room temperature for 3 h. Volatile materials were evaporated under high vacuum and the residue was co-evaporated with toluene followed by neutralization with 7N ammonia in methanol. Purification by silica gel column chromatography afforded 26a as a white solid (20 mg, 32%).

Method 3 (Reference 27): To a solution of compound 22a (20 mg, 0.028 mmol) in anhyd. dichloromethane (0.6 mL)

was added anhyd. $ZnBr_2$ (64 mg, 0.28 mmol) and stirred vigorously for 2 h (reaction was practically completed in 10-20 min). Water was added, and the product was extracted in ethyl acetate several times, organic phase was separated, dried, evaporated. The residue was purified by silica gel column chromatography to afford the products 8a (2.0 mg, 22%) and 26a (4.2 mg, 41%).

(N)-methanocarba-2',3'-O-isopropylidene-$N^6$Boc-2-thio-methyl-adenosine (30): Compound 22a (200 mg, 0.283 mmol) was dissolved in anhyd. acetone (3.0 mL) and was added p-TSA hydrate (108 mg, 0.566 mmol). The reaction was stirred at room temperature for 18 h. The volatile materials were removed by rotary evaporation under reduced pressure. The residue was partitioned between aq. $NaHCO_3$ and 5% i-PrOH in $CH_2Cl_2$. The organic layer was separated and dried over anhydrous $Na_2SO_4$. Rotary evaporation under vacuum, followed by purification using silica gel chromatography gave the desired compound as a white foam (80 mg, 61%, TLC eluent, 5% MeOH in $CH_2Cl_2$; $R_f$=0.35). $^1H$ NMR (400 MHz, Chloroform-d) δ 7.87 (q, J=3.2, 2.5 Hz, 1H), 7.72 (d, J=4.9 Hz, 1H), 5.55 (dd, J=7.4, 4.6 Hz, 1H), 5.29 (q, J=3.0, 2.2 Hz, 1H), 4.80 (d, J=4.7 Hz, 1H), 4.69 (d, J=6.5 Hz, 1H), 4.24 (dd, J=12.2, 6.7 Hz, 1H), 3.45 (d, J=7.6 Hz, 1H), 3.37 (ddd, J=11.3, 5.0, 2.5 Hz, 1H), 2.69 (q, J=3.1, 2.4 Hz, 3H), 1.69 (q, J=4.7 Hz, 1H), 1.55 (dd, J=6.1, 3.5 Hz, 12H), 1.25 (s, 3H), 1.17 (t, J=5.2 Hz, 1H), 0.97 (dd, J=9.4, 5.0 Hz, 1H). ESI-MS $[M+H]^+$ for $C_{21}H_{29}N_5O_5S$ calculated, 464.1962. found, 464.2.

(N)-methanocarba-2',3'-O-isopropylidene-2-thiomethyl-adenosine-5'-phosphate di-tert-butyl ester (31): Vacuum dried mixture of compound 26a (12 mg, 0.033 mmol) and tetrazole (7.0 mg, 0.10 mmol) was dissolved in anhyd. THE (0.75 mL) under argon atmosphere and to this was added di-tert-butyl-N,N-diethyl-phosphoramidite (14 μL, 0.05 mmol). The reaction mixture was stirred at room temperature for 18 h. 30% aq.$H_2O_2$ (3.0 μL, 0.033 mmol) was added and stirred at room temperature for 3 h. The volatile materials were evaporated under high vacuum and the residue was purified by silica gel column chromatography to afford 31 as a white foam (15 mg, 81%, TLC eluent, 5% MeOH in $CH_2Cl_2$; $R_f$=0.40). Spectral data are as reported (Reference 6).

[Note: if the next deprotection reaction was carried out without purification (only workup), sulfoxide product was observed, implying, any residual hydrogen peroxide in the presence of acid increases the reactivity of peroxides towards thio-alkanes].

REFERENCES

1. Jordheim, L. P.; Durantel, D.; Zoulim, F.; Dumontet, C. Advances in the development of nucleoside and nucleotide analogues for cancer and viral diseases. *Nat. Rev. Drug* Discov. 2013, 12, 447-64.
2. Jacobson, K. A.; Tosh, D. K.; Toti, K. S.; Ciancetta, A. Polypharmacology of conformationally locked methanocarba nucleosides. *Drug Disc. Today* 2017, 22, 1782-1791.
3. Marquez, V. E.; Siddiqui, M. A.; Ezzitouni, A.; Russ, P. L.; Wang, J.; Wagner, R. W.; Matteucci, M. D. Nucleosides with a twist. Can fixed forms of sugar ring pucker influence biological activity in nucleosides and oligonucleotides? *J. Med. Chem.,* 1996, 39, 3739-3747.
4. Marquez, V. E. The properties of locked methanocarba nucleosides in biochemistry, biotechnology and medicine. In Modified Nucleosides in Biochemistry Biotechnology and Medicine (Herdewijn, P., ed.), 2008, pp. 307-341, Wiley-VCH.
5. Tchilibon, S.; Joshi, B. V.; Kim, S. K.; Duong, H. T.; Gao, Z. G.; Jacobson, K. A. (N)-Methanocarba 2, $N^6$-disubstituted adenine nucleosides as highly potent and selective $A_3$ adenosine receptor agonists. *J. Med. Chem.* 2005, 48, 1745-58.
6. Ravi, R. G.; Kim, H. S.; Servos, J.; Zimmermann, H.; Lee, K.; Maddileti, S.; Boyer, J. L.; Harden, T. K.; Jacobson, K. A. Adenine nucleotides analogues locked in a Northern methanocarba conformation: Enhanced stability and potency as $P2Y_1$ receptor agonists. *J. Med. Chem.* 2002, 45, 2090-2100.
7. R. Volpini, S. Costanzi, C. Lambertucci, F. R. Portino, S. Taffi, S. Vittori, K.-N. Klotz, G. Cristalli. Adenosine receptor agonists: synthesis and binding affinity of 2-(aryl)alkylthioadenosine derivatives. *ARKIVOC* (Gainesville, FL, U.S.) 2004, 5, 301-311.
8. El-Tayeb, A.; Iqbal, J.; Behrenswerth, A.; Romio, M.; Schneider, M.; Zimmermann, H.; Schrader, J.; Müller, C. E., Nucleoside-5'-monophosphates as Prodrugs of Adenosine $A_{2A}$ Receptor Agonists Activated by ecto-5'-Nucleotidase. *J. Med. Chem.* 2009, 52, 7669-7677.
9. Joshi, B. V., Melman, A., Mackman, R. L., Jacobson, K. A. Synthesis of ethyl (1S,2R,3S,4S,5S)-2,3-O-(isopropylidene)-4-hydroxy-bicyclo[3.1.0]hexane-carboxylate from L-ribose: A versatile chiral synthon for preparation of adenosine and P2 receptor ligands. *Nucleos. Nucleot. Nucleic Acids,* 2008, 27, 279-291.
10. Marquez, V. E.; Russ, P.; Alonso, R.; Siddiqui, M. A.; Hernandez, S.; George, C.; Nicklaus, M. C.; Dai, F.; Ford, H. Synthesis of conformationally restricted carbocyclic nucleosides: The role of the O(4')-atom in the key hydration step of adenosine deaminase. *Helv. Chim. Acta* 1999, 82, 2119-2129.
11. Choi, Y.; Moon, H. R.; Yoshimura, Y.; Marquez, V. E. Recent advances in the synthesis of conformationally locked nucleosides and their success in probing the critical question of conformational preferences by their biological targets. *Nucleosides Nucleotides Nucleic Acids* 2003, 22, 547-557.
12. Tosh, D. K.; Padia, J.; Salvemini, D.; Jacobson, K. A. Efficient, large-scale synthesis and preclinical studies of MRS5698, a highly selective $A_3$ adenosine receptor agonist that protects against chronic neuropathic pain. *Purinergic Signalling* 2015, 11, 371-387.
13. Michel B Y, Strazewski P (2009) Total syntheses of a conformationally locked north-type methanocarba puromycin analogue and a dinucleotide derivative. *Chem. Eur. J* 2009, 15, 6244-6257.
14. Korinek, W. S., Lechleiter, J. D., Liston, T. E. Compounds and Methods for Treating Neurological and Cardiovascular Conditions. Washington, DC: U.S. Patent and Trademark Office. US2018021363A1, Jan. 25, 2018.
15. Lu, W., Sengupta, S., Petersen, J. L., Akhmedov, N. G., Shi, X. Mitsunobu coupling of nucleobases and alcohols: An efficient, practical synthesis for novel nonsugar carbon nucleosides. *J. Org. Chem.* 2007, 72, 5012-5015
16. Arico, J. W., Calhoun, A. K., Salandria, K. J., McLaughlin, L. W. (2010). Tetramethylsuccinimide as a directing/protecting group in purine glycosylations. *Org. Lett.* 2010, 12, 120-122.
17. Reddy, P. Y., Kondo, S., Toru, T., Ueno, Y. Lewis acid and hexamethyldisilazane-promoted efficient synthesis of N-alkyl- and N-arylimide derivatives. *J. Org. Chem.* 1997, 62, 2652-2654.

18. Fletcher, S.; Shahani, V. M.; Gunning, P. T. Facile and efficient access to 2,6,9-tri-substituted purines through sequential $N^9$,$N^2$ Mitsunobu reactions. *Tetrahedron Lett.* 2009, 50, 4258-4261.

19. Fletcher, S.; Shahani, V. M.; Lough, A. J.; Gunning, P. T. Concise access to $N^9$-mono-, $N^2$-mono- and $N^2$,$N^9$-di-substituted guanines via efficient Mitsunobu reactions. *Tetrahedron* 2010, 66, 4621-4632.

20. Toti, K., Osborne, D., Ciancetta, A., Boison, D., Jacobson, K. A. South (S)- and North (N)-methanocarba-7-deazaadenosine analogues as inhibitors of human adenosine kinase. *J. Med. Chem.,* 2016, 59:6860-6877.

21. Yu R H C, Brown B H, Polniaszek R P, Graetz B R, Sujino K, Tran D, Triman A S, Kent K M, Pfeiffer S. Processes and intermediates for preparing anti-HIV agents. US 20180079773, WO 2012/159047 A1.

22. Breault G, Eyermann C J, Geng B. Derivatives of adenine and 8-aza-adenine and uses thereof-796, WO2009034386A1.

23. Bergmann, W., Stempien, M. F. Marine products. XLIII. Nucleosides of sponges. 5. Synthesis of spongosine. *J. Org. Chem.,* 22, 1957, 1575-1577.

24. von Lubitz, D. K. J. E., Lin, R. C.-S., Popik, P., Carter, M. F., Jacobson, K. A. Adenosine $A_3$ receptor stimulation and cerebral ischemia. *Eur. J. Pharmacol.,* 1994, 263:59-67.

25. Jacobson, K. A., Tosh, D. K., Toti, K. S., Ciancetta, A. Polypharmacology of conformationally locked methanocarba nucleosides. *Drug Disc. Today,* 2017, 22:1782-1791.

26. Söderström, M., Zamaratski, E., Odell. L. R. $BF_3$·$SMe_2$ for thiomethylation, nitro reduction and tandem reduction/SMe insertion of nitrogen heterocycles. *Eur. J. Org. Chem.* 2019, 5402-5408.

27. Kohli, V., Blocker, H., Koster, H. The triphenylmethyl (trityl) group and its uses in nucleotide chemistry. *Tetrahedron Letters,* 1980, 21, 2683-2686.

28. Kim, Hak Sung et al. Methanocarba Modification of Uracil and Adenine Nucleotides: High Potency of Northern Ring Conformation at $P2Y_1$, $P2Y_2$, $P2Y_4$, and $P2Y_{11}$ but Not $P2Y_6$ Receptors. *J. Med. Chem.,* 2002, 45, 208-218.

Example 2: Pharmacokinetics of Compounds Following Intraperitoneal Administration to Mice Examples 1 and 2 of U.S. Pat. No. 9,789,131, which is incorporated herein by reference, describe assays for determining the plasma and brain concentrations of certain compounds following intraperitoneal administration of the compounds to mice at a dose used in mouse photothrombosis and traumatic brain injury models. Compounds described herein may be evaluated using such assays or similar variants thereof.

Example 3: Plasma and Brain Binding of Test Compounds in Mice

Example 3 of U.S. Pat. No. 9,789,131, which is incorporated herein by reference, describes assays for determining the plasma and brain free fraction of certain compounds such as I-1. Compounds described herein may be evaluated using such assays or similar variants thereof.

Example 4: In Vitro Stability and Metabolism of Test Compounds in Mouse and Human Blood and Plasma Example 4 of U.S. Pat. No. 9,789,131, which is incorporated herein by reference, describes assays for determining the in vitro stability and metabolic fate in mouse and human blood and plasma of certain compounds such as I-1. Compounds described herein may be evaluated using such assays or similar variants thereof.

Example 5: Neuroprotective Efficacy of Test Compounds after TBI in Mice

Example 5 of U.S. Pat. No. 9,789,131, which is incorporated herein by reference, describes assays for determining the efficacy of certain compounds such as I-1 in inducing neuroprotection in mice subjected to traumatic brain injury (TBI). Compounds described herein may be evaluated using such assays or similar variants thereof. The assay procedure is reproduced below.

Purpose

This study is designed to determine the neuroprotective efficacy of test compounds in mice subjected to traumatic brain injury (TBI) and to compare free mice treated with test compounds and an adenosine $A_3$ receptor full agonist, Cl-IB-IMECA.

Methods

Chemicals: Test compounds are prepared as described above. Cl-IB-IMECA is commercially available from Tocris Biosciences (Bristol, UK) and several other vendors. All other chemicals may be obtained from commercial vendors such as Sigma-Aldrich (St. Louis, MO).

Animals and traumatic brain injury (TBI): TBI is performed with a controlled closed skull injury model as described in Talley-Watts et al. 2012 (*J. Neurotrauma* 30, 55-66). Following the method described therein, a pneumatic impact device is used to generate a moderate TBI leaving the skull and dura matter intact. To achieve this, C57BL/6 mice are anesthetized with isoflurane (3% induction, 1% maintenance) in 100% oxygen. A body temperature of 37° C. is maintained using a temperature-controlled heated surgical table. A small midline incision is made on the scalp using aseptic surgical techniques. A 5 mm stainless steel disc is positioned on the skull and fixed using superglue on the right parietal bone between bregma and lamda over the somatosensory cortex. The mouse is then positioned on a stage directly under the pneumatic impact tip. A calibrated impact is delivered at 4.5 m/s at a depth of 2 mm which generates a moderate injury in the mouse. Scalp incisions are closed using 4-0 nylon braided suture and antibiotic ointment applied to the incision. Mice are placed in a Thermo-Intensive Care Unit (Braintree Scientific model FV-1; 37° C.; 27% $O_2$) and monitored until fully awake and moving freely. Thirty minutes following injury or sham (uninjured), mice are treated with either vehicle (saline), test compound, or control (Cl-IB-IMECA). Exemplary doses of test compound and Cl-IB-MECA are 0.16 and 0.24 mg/kg, respectively, each equivalent to equimolar doses of approximately 0.5 μmol/kg.

Western Blot Analysis for GFAP: At selected survival times, mice are anesthetized under isoflurane and sacrificed. The brain is removed and placed on ice for dissection into impacted and non-impacted brain hemispheres. The isolated tissue is rapidly homogenized in chilled homogenization buffer (0.32 M Sucrose, 1 mM EDTA, 1 M Tris-HCL pH=7.8) on ice using a Wheaton glass dounce (20 strokes). The homogenate is transferred to a 2 mL tube and centrifuged at 1000 g for 10 minutes at 4° C. and the supernatant is collected and analyzed. Protein concentration is determined by the BCA assay using a 1:50 dilution. 100 μg of protein is removed as an aliquot for each sample and Laemmli buffer containing β-mercaptoethanol added and the sample placed in a heat block for 3 minutes at 95° C. Samples are loaded on a 12% gel and run at 80 V for 20 minutes followed by 40 minutes at 130 V. Samples are transferred to nitrocellulose membrane at 100 V for 1 hour. The membrane is blocked with 5% milk in TBS-T for 30 minutes. GFAP (1:1000-Imgenex IMG-5083-A) is added and placed at 4° C. overnight. The membrane is washed with TBS-T three times for 10 minutes. Secondary antibody for GFAP (Donkey anti-rabbit HRP conjugated (ImmunoJackson Laboratories; 711-035-152; 1:20000) is applied at room temperature for 1 hour. The membranes are washed with TBS-T for 15 minutes (3 times) and developed using the Western Lightning Plus-ECL kit (PerkinElmer, Inc.) following manufacturer's directions.

Results

Effective compounds (I-1 is known to be effective in this model) would be expected to reduce GFAP expression in the mouse brains following TBI. Glial Fibrillary acidic protein (GFAP) expression is used as a biomarker for reactive gliosis after TBI (Talley-Watts et al. 2012; Sofroniew, 2005). Western blot analysis will be performed for GFAP expression in Sham, TBI or TBI test compound-treated mice sacrificed at 7 days post-injury. First, western blot analysis confirms that TBI induces a significant increase in GFAP expression, both in the Ipsilateral (where the impact is centered) and contralateral sides of the brain at 7 days post-injury. GFAP expression is significantly lower in blots from mice treated with test compounds such as I-1, which are injected within 30 minutes of the initial trauma. For loading controls, beta-actin western blots are used. Typically, data will be averaged from 3 separate experiments and showing the relative change in GFAP/actin ratios (band intensities measured in Image J software).

Effective compounds (I-1 is known to be effective in this model) would be expected to reduce GFAP levels in mouse plasma following TBI. GFAP levels in the plasma have also been used as a biomarker for TBI, due to the breakdown of the blood brain barrier (BBB) after a trauma. Consequently, we will also collect plasma samples at day 7 from TBI mice. GFAP levels are easily detected at day 7 by western blot analysis.

Compound I-1 is a low-affinity (4900 nM) agonist of the $A_3$ receptor in the mouse. Conversely, Cl-IB-MECA is a high-affinity (0.18 nM) agonist in the mouse—the differences in affinity of these two compounds is approximately 25,000-fold. However, in the mouse photothrombotic stroke and TBI models, I-1 demonstrates significant efficacy that is blocked by the $A_3$ antagonist MRS1523, whereas Cl-IB-IMECA is either inactive (stroke) or weakly active. One potential explanation for this surprising result is based on ADME/PK data we have generated for I-1 and Cl-IB-IMECA. Cl-IB-IMECA is a lipophilic compound (cLogP approx 2.5) that is highly bound to plasma proteins (free fraction 0.002) and highly bound nonspecifically to brain tissue (free fraction 0.002). I-1 is a very hydrophilic compound (cLogP<0) that has a very large unbound fraction in plasma (0.74) and brain (0.13). Only unbound drug is available for distribution across membranes and interaction with receptors. Thus, despite its lower receptor affinity, the fraction of I-1 available to interact with the $A_3$ receptor in these mouse models is at least 1000-fold higher than that of Cl-IB-IMECA. These significant differences in compound physicochemical properties and ADME/PK characteristics may contribute to the non-obvious efficacy of I-1 and other compounds described herein as compared to Cl-IB-IMECA (and MRS5698, another lipophilic and highly-bound/high-affinity full $A_3$R agonist) in these mouse models. An alternative explanation is that compounds such as I-1 and other compounds shown in Table 1 act as dual $A_3$ and $A_1$ agonists or selective $A_1$ agonists.

Biased Agonism. The adenosine $A_3$ receptor is a G protein-coupled pleiotropic receptor, i.e. agonism of this receptor potentially activates multiple downstream pathways via multiple G proteins as well as Beta-arrestin. Pathways that are activated by $A_3$ receptor agonism have currently been identified, but may not be limited to, Gq11-mediated intracellular calcium mobilization, Gi-mediated modulation of cAMP production, and Gi-mediated phosphorylation of ERK1/2 and Akt. One aspect of our discoveries is in the $A_3$-mediated mobilization of intracellular calcium resulting in promotion of mitochondrial ATP production in astrocytes.

An emerging concept in receptor pharmacology is biased agonism. This concept states that for pleiotropic receptors there are actually different classes of agonists, some of which may activate all downstream pathways while others demonstrate bias in activating a subset of the downstream pathways. In drug discovery and receptor pharmacology, biased agonism introduces the possibility of increased specificity in pathway activation with fewer off-target effects, i.e. fewer side-effects. There is evidence for biased agonism for the $A_3$ receptor. However, prototypical high-affinity agonists such as Cl-IB-IMECA and MRS5698 are full agonists that do not demonstrate biased activation of the aforementioned downstream pathways. Accordingly, and without wishing to be bound by any particular theory, it is believed that certain compounds described herein are biased agonists that preferentially activate intracellular calcium mobilization with less/no activation of the other $A_3$-mediated or $A_1$-mediated pathways.

Example 6: Neuroprotective Efficacy of MRS4322 after Stroke in Mice

Examples 6 and 7 of U.S. Pat. No. 9,789,131, which is incorporated herein by reference, describes assays for determining the efficacy of certain compounds such as I-1 in inducing neuroprotection in mice subjected to stroke. Compounds described herein may be evaluated using such assays or similar variants thereof. The assay procedure is reproduced below.

Purpose

This study is designed to determine the neuroprotective efficacy of test compounds in mice subjected to stroke with and without the $A_3$ receptor antagonist MRS1523, and in comparison to full A3R agonists MRS5698 and Cl-IB-IMECA. MRS1523 has the following structure:

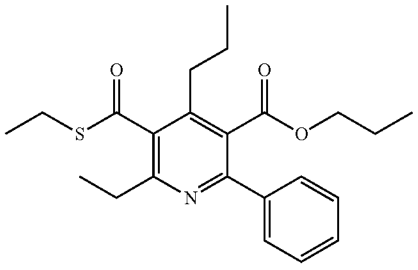

MRS1523

Methods

Chemicals: Test compounds are prepared as described above. Cl-IB-MECA, MRS5698 and MRS2365 are commercially available from Tocris Bioscience (Bristol, UK) and several other vendors. All other chemicals may be obtained from Sigma-Aldrich (St. Louis, MO).

Photothrombosis-induced Stroke: Photothrombosis is performed as described in Zheng et al 2010 (PloS One 5 (12): e14401). In brief, Rose Bengal is a fluorescent dye that when injected into the vasculature and excited, generates singlet oxygen that damages the endothelial wall and induces a local thrombosis (clot). Using this technique, mice are given a 0.1 mL tail-vein injection of sterilized Rose Bengal (RB, Sigma, U.S.A.) in artificial cerebral spinal fluid (aCSF). The RB concentration is 20 mg/mL. A cortical region is centered in the imaging field and illuminated with a green laser (543 nm, 5 mW) using a 0.8-NA 40× water-immersion objective (Nikon, Tokyo). The clot formation is monitored in real time until the targeted vessel or downstream capillaries are firmly occluded. Stable clots are subsequently identified by a non-fluorescent vessel segmentation ending with highly fluorescent regions. In control experiments, either laser illumination or Rose Bengal itself did not lead to clot formation. Treatments, at doses such as 0.5 μmol/kg are introduced via intraperitoneal injections (i.p.). For experiments with $A_3$ receptor antagonist MRS1523, mice are administered intraperitoneal injections (2 mg/kg) at the 0 and 2 hour timepoints to ensure receptor antagonism throughout the course of the study.

Animals and Photothrombosis-induced Stroke: Stroke is performed as described in Zheng et al 2010 (PloS One 5 (12): e14401). Female C57Bl/6 mice (4-6 months) are used in this study. From the methods of this manuscript: Mice are anesthetized at 3% isoflurane with 100% oxygen and subsequently maintained at 1% isoflurane through a nosecone. Depth of anesthesia is monitored and regulated according to vital signs, pinch withdrawal and eye blinks. Body temperature is maintained at 37° C. by a feedback-controlled heating pad (Gaymar T/Pump). Vital signs including oxygen saturation, respiratory rate, and heart rate are continuously monitored by using the MouseOx system (STARR Life Sciences). The hair on each mouse's head is trimmed and a small incision is made in the scalp to expose the skull. A custom-made stainless steel plate is glued to the skull with VetBond Tissue Adhesive (3M, St Paul, MN). A cranial thinned-skull imaging window is created over the right primary somatosensory cortex (~1.5 mm posterior to Bregma and 2 mm lateral from midline) depending on the experiment. In brief, a large region of the skull is first thinned with the electric drill and then further thinned with a surgical blade. The final thickness of the thinned skull is approximately 50 μm. After the cranial imaging window is created, mice are transferred to microscope stage and used for photothrombosis or imaging experiments. For the repeat imaging experiments, the plate is carefully detached from the skull and the scalp is sutured (Ethicon 6-0 sild suture). After each experiment, the mice are either returned to cages until the next timepoint or sacrificed. All procedures are approved by the Institutional Animal Care and Use Committee (IACUC) at University of Texas Health Science Center at San Antonio. Thirty minutes following stroke or sham (uninjured), mice are treated with either vehicle (saline) or test compound.

Post photothrombotic infarction evaluation. The size of cerebral infarcts is evaluated using 2,3,5-Triphenyltetrazolium chloride (TTC) staining as described in Zheng et al 2010 (PloS One 5 (12): e14401). In brief, RB-induced lesions in brain slices are stained with TTC. TTC is a colorless dye that stains healthy brain tissue red when reduced by the mitochondrial enzyme succinyl dehydrogenase (Bederson J B et al., 1986). The absence of staining in necrotic tissue is then used to define the area of a brain infarction. Mice are sacrificed by cervical dislocation, their brains removed and then placed in ice cold HBSS for 3 minutes. The brain is subsequently transferred to a brain mold (KOPF), sliced into 1 mm sections and immersed in 2% TTC (5 min) at 37° C. The sections are fixed in 10% buffered formaldehyde solution overnight at 4° C. Slices are imaged on a flatbed scanner (HP scanjet 8300) for analysis of the lesion size at 1200 dpi.

Results

Multivessel photothrombotic strokes are induced in mice using tail-vein injected in conjunction with RB as described above. Within 30 minutes of clot formation, mice are injected intraperitoneally with either vehicle (saline control), or test compound. Twenty-four hours after the initial stroke, the brain infarction size is evaluated with TTC staining as described above.

It is expected that the $A_3$ receptor antagonist MRS1523 will inhibit neuroprotection of test compound after stroke. Multivessel photothrombotic strokes are induced in mice as described above. However, in this experiment, mice are treated with intraperatoneal injections of the $A_3$ receptor antagonist, MRS1523 (2 mg/kg) at the 0 and 2 hour timepoints to ensure receptor antagonism. Mice are then injected with either vehicle, test compound, MRS5698 or Cl-IBMECA within 30 minutes of clot formation at the concentrations described above. Twenty-four hours later, brain infarction sizes are evaluated with TTC staining.

Example 7: Experimental Protocol for Determining Affinity, Agonism, and Biased Agonism of Compounds at Adenosine Receptors Such as the $A_3$ Adenosine Receptor ($A_3$R The following assays may be used to determine whether a disclosed compound exhibits agonism, partial agonism, or biased agonism (also known as functional selectivity or agonist trafficking) at the $A_1$, $A_{2A}$, or $A_3$ receptor. See Paoletta, S.; Tosh, D. K.; Finley, A.; Gizewski, E.; Moss, S. M.; Gao, Z. G.; Auchampach, J. A.; Salvemini, D.; Jacobson, K. A., "Rational design of sulfonated A3 adenosine receptor-selective nucleosides as pharmacological tools to study chronic neuropathic pain," J. Med. Chem. 2013, 56, 5949-5963.

Binding Studies of Human Adenosine Receptors (Includes $A_1$, $A_{2A}$ and $A_3$)

[3H]R—$N^6$-Phenylisopropyladenosine ([3H]R-PIA, 63 Ci/mmol), [$^3$H](2-[p-(2-carboxyethyl)phenyl-ethylamino]-5'-N-ethylcarboxamido-adenosine) ([$^3$H]CGS21680, 40.5 Ci/mmol) and [$^{125}$I]$N^6$-(4-amino-3-iodobenzyl)adenosine-5'-N-methyluronamide ([$^{125}$I]I-AB-MECA, 2200 Ci/mmol) were purchased from Perkin-Elmer Life and Analytical Science (Boston, MA). Test compounds were prepared as 5 mM stock solutions in DMSO and stored frozen. Pharmacological standards Cl-IB-MECA ($A_3$AR agonist), adenosine-5'-N-ethylcarboxamide (NECA, nonselective AR agonist) and 2-chloro-$N^6$-cyclopentyladenosine (CCPA, $A_1$AR agonist) were purchased from Tocris R&D Systems (Minneapolis, MN).

Cell Culture and Membrane Preparation—CHO cells stably expressing the recombinant $hA_1$ and $hA_3$ARs and HEK293 cells stably expressing the $hA_{2A}$AR were cultured in Dulbecco's modified Eagle medium (DMEM) and F12 (1:1) supplemented with 10% fetal bovine serum, 100 units/mL penicillin, 100 μg/mL streptomycin, and 2 μmol/mL glutamine. In addition, 800 μg/mL geneticin was added to the $A_{2A}$ media, while 500 μg/mL hygromycin was added to the $A_1$ and $A_3$ media. After harvesting, cells were homogenized and suspended in PBS. Cells were then centrifuged at 240 g for 5 min, and the pellet was resuspended in 50 mM Tris-HCl buffer (pH 7.5) containing 10 mM $MgCl_2$. The suspension was homogenized and was then ultra-centrifuged at 14,330 g for 30 min at 4° C. The resultant pellets were resuspended in Tris buffer, incubated with adenosine deaminase (3 units/mL) for 30 min at 37° C. The suspension was homogenized with an electric homogenizer for 10 sec, pipetted into 1 mL vials and then stored at −80° C. until the binding experiments. The protein concentration was measured using the BCA Protein Assay Kit from Pierce Biotechnology, Inc. (Rockford, IL).

Binding assays: Into each tube in the binding assay was added 50 μL of increasing concentrations of the test ligand in Tris-HCl buffer (50 mM, pH 7.5) containing 10 mM $MgCl_2$, 50 μL of the appropriate agonist radioligand, and finally 100 μL of membrane suspension. For the $A_1$AR (22 μg of protein/tube) the radioligand used was [$^3$H]R-PIA (final concentration of 3.5 nM). For the $A_{2A}$AR (20 μg/tube) the radioligand used was [$^3$H]CGS21680 (10 nM). For the $A_3$AR (21 μg/tube) the radioligand used was [$^{125}$I]I-AB-MECA (0.34 nM). Nonspecific binding was determined using a final concentration of 10 μM NECA diluted with the buffer. The mixtures were incubated at 25° C. for 60 min in a shaking water bath. Binding reactions were terminated by filtration through Brandel GF/B filters under a reduced pressure using a M-24 cell harvester (Brandel, Gaithersburg, MD). Filters were washed three times with 3 mL of 50 mM ice-cold Tris-HCl buffer (pH 7.5). Filters for $A_1$ and $A_{2A}$AR binding were placed in scintillation vials containing 5 mL of Hydrofluor scintillation buffer and counted using a Perkin Elmer Liquid Scintillation Analyzer (Tri-Carb 2810TR). Filters for $A_3$AR binding were counted using a Packard Cobra II T-counter. The $K_i$ values were determined using GraphPad Prism for all assays.

Binding Assay, Mouse $A_3$ Receptor

Similar competition binding assays may be conducted using HEK293 cell membranes expressing mARs using [$^{125}$I]I-AB-MECA to label $A_1$ or $A_3$ARs and [3H]CGS21680 to label $A_{2A}$ARs. $IC_{50}$ values were converted to $K_i$ values using known methods. Nonspecific binding was determined in the presence of 100 μM NECA.

Functional Assay cAMP accumulation assay: Intracellular cAMP levels in CHO cells expressing the recombinant $hA_3$AR were measured using an ELISA assay. Cells were first harvested by trypsinization. After centrifugation and resuspension in medium, cells were planted in 96-well plates in 0.1 mL medium. After 24 h, the medium was removed and cells were washed three times with 0.2 mL DMEM, containing 50 mM HEPES, pH 7.4. Cells were then treated with the agonist (10 μM NECA for $hA_3$AR) or test compound in the presence of rolipram (10 μM) and adenosine deaminase (3 units/mL). After 30 min forskolin (10 μM) was added to the medium, and incubation was continued for an additional 15 min. The reaction was terminated by removing the supernatant, and cells were lysed upon the addition of 100 μL of 0.1 M ice-cold HCl. The cell lysate was resuspended and stored at −20° C. For determination of cAMP production, 50 μL of the HCl solution was used in the Amersham cAMP Enzyme Immunoassay following the instructions provided with the kit. The results were interpreted using a SpectroMax M5 Microplate reader (Molecular Devices, Sunnyvale, CA) at 450 nm.

Similar cAMP assays were conducted with HEK293 cells expressing the $mA_1$AR or $mA_3$AR. HEK293 cells were detached from cell culture plates, resuspended in serum-free DMEM containing 25 mM HEPES (pH 7.4), 1 unit/ml adenosine deaminase, 4-(3-butoxy-4-methoxyphenyl) methyl-2-imidazolidone (Tocris, Ro 20, 1724, 20 μM) and 300 nM 8-[4-[4-(4-chlorophenzyl)piperazide-1-sulfonyl) phenyl]]-1-propylxanthine (Tocris, PSB603, 300 nM) inhibit $A_{2B}$ARs expressed endogenously in HEK293 cells, and then transferred to polypropylene tubes (2×10$^5$ cells/tube). The cells were co-incubated with forskolin (10 μM) and AR ligands for 15 min at 37° C. with shaking, after which the assays were terminated by adding 500 μL 1 N HCl. The lysates were centrifuged at 4000×g for 10 min. The cAMP concentration was determined in the supernatants using a competitive binding assay, as previously described (Nordstedt C, Fredholm B B, "A modification of a protein-binding method for rapid quantification of cAMP in cell-culture supernatants and body fluid," Anal. Biochem. 1990; 189:231-234. [PubMed: 2177960]). $EC_{50}$ and $E_{max}$ values were calculated by fitting the data to: $E=E_{min}+(E_{max}-E_{min})/(1+10^{x-logEC50})$.

$A_3$R binding of selected compounds. Using methods described herein, the affinity of selected compounds at the $A_3$ receptor was measured. Results are shown below.

TABLE 3

Affinity of Selected Compounds at Human $A_3$R (n = 1)

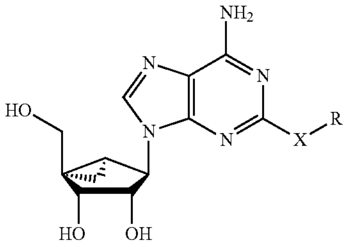

8a-f

| Compound No. | Compound I-# | MRS # | Affinity (nM) |
|---|---|---|---|
| 8a X = S, R = Me | I-1 | MRS4322 | 1490 |
| 8b X = S, R = Et | I-2 | MRS7711 | 909 |
| 8c X = S, R = n-Hex | I-3 | MRS7662 | 504 |
| 8d X = S, R = c-Hex | I-4 | MRS7706 | 1170 |
| 8e X = S, R = CH2Ph | I-5 | MRS7675 | 55 |
| 8f X = S, R = (CH2)2Ph | I-6 | MRS7665 | 379 |
| 8g X = O, R = Me | I-7 | MRS7658 | 1053 |

Determination of Biased Agonism at $A_3$R.

Materials. Fluo-4, Dulbecco's modified Eagle's medium (DMEM), and penicillin-streptomycin may be purchased from Invitrogen (Carlsbad, CA). Adenosine deaminase (ADA) and hygromycin-B may be purchased from Roche (Basel, Switzerland). Fetal bovine serum (FBS) may be purchased from ThermoTrace (Melbourne, Australia). AlphaScreen SureFire extracellular signal-regulated kinases 1 and 2 (ERK1/2), Akt 1/2/3, and cAMP kits may be obtained from PerkinElmer (Boston, MA). Test compounds may be prepared as described herein. All other reagents may be purchased from commercial vendors such as Sigma-Aldrich (St. Louis, MO).

Cell Culture. The sequence of the human $A_3$R may be cloned into the Gateway entry vector, pDONR201, and then transferred in the Gateway destination vector, pEF5/FRT/

V5-dest, using methods described previously (Stewart et al., 2009). $A_3$-FlpIn-CHO cells may be generated using methods described previously (May et al., 2007) and maintained at 37° C. in a humidified incubator containing 5% $CO_2$ in DMEM supplemented with 10% FBS and the selection antibiotic hygromycin-B (500 μg/ml). For cell survival, ERK1/2 phosphorylation, Akt 1/2/3 phosphorylation, and calcium mobilization assays, cells may be seeded into 96-well culture plates at a density of 4×104 cells/well. After 6 hours, cells are washed with serum-free DMEM and maintained in serum-free DMEM for 12-18 hours at 37° C. in 5% CO2 before assaying. For cAMP assays, cells may be seeded into 96-well culture plates at a density of 2×104 cells/well and incubated overnight at 37° C. in 5% $CO_2$ prior to assay.

Cell Survival Assays. Media is removed and replaced with HEPES-buffered saline solution (10 mM 4-(2-hydroxyethyl)-1-piperazineethanesulfonic acid (HEPES), 146 mM NaCl, 10 mM D-glucose, 5 mM KCl, 1 mM $MgSO_4$, 1.3 mM $CaCl_2$, and 1.5 mM $NaHCO_3$, pH 7.45) containing ADA (1 U/ml) and penicillin-streptomycin (0.05 U/ml) in the absence and presence of $A_3R$ ligands. Plates are then maintained at 37° C. in a humidified incubator for 24 hours, after which 5 mg/ml propidium iodide is added to cells. Plates may be then read on an EnVision plate reader (PerkinElmer), with excitation and emission set to 320 nm and 615 nm, respectively. Data will be normalized to 100% cell survival and 0% cell survival, determined at t=0 hours in HEPES buffer and t=24 hours in Milli-Q water, respectively.

ERK1/2 and Akt 1/2/3 Phosphorylation Assays. A concentration-response curve of ERK1/2 and Akt 1/2/3 phosphorylation for each ligand may be performed in serum-free DMEM containing 1 U/ml ADA (5-minute exposure at 37° C.). Agonist stimulation may be terminated by removal of media and the addition of 100 ml of SureFire lysis buffer to each well. Plates are then agitated for 5 minutes. Detection of pERK1/2 may involve an 80:20:120:1:1 v/v/v/v/v dilution of lysate: activation buffer: reaction buffer: AlphaScreen acceptor beads: AlphaScreen donor beads in a total volume of 11 ml in a 384-well ProxiPlate. Plates may be incubated in the dark at 37° C. for 1 hour followed by measurement of fluorescence by an EnVision plate reader (PerkinElmer) with excitation and emission set to 630 nm and 520-620 nm, respectively. Detection of Akt 1/2/3 phosphorylation may employ a 40:9.8:39.2:1 v/v/v/v dilution of lysate: activation buffer: reaction buffer: AlphaScreen acceptor beads in a total volume of 9:1 in a 384-well Proxiplate. Plates may be incubated in the dark at room temperature for 2 hours, after which a 19:1 v/v dilution of dilution buffer: AlphaScreen donor beads may be added in a total volume of 11 μl. Plates may be incubated at room temperature for a further 2 hours, followed by measurement of fluorescence by an EnVision plate reader (PerkinElmer) with excitation and emission set to 630 nm and 520-620 nm, respectively. Agonist concentration-response curves are normalized to the phosphorylation mediated by 10% FBS (5-minute stimulation).

Calcium Mobilization Assays. Media may be removed from 96-well plates and replaced with HEPES-buffered saline solution containing 1 U/ml ADA, 2.5 mM probenecid, 0.5% bovine serum albumin (BSA), and 1 M Fluo4. Plates may be incubated in the dark for 1 hour at 37° C. in a humidified incubator. A FlexStation plate reader (Molecular Devices, Sunnyvale, CA) may perform the addition of HEPES-buffered saline solution in the absence and presence of agonist and measured fluorescence (excitation, 485 nm; emission, 520 nm) every 1.52 seconds for 75 seconds. The difference between the peak and baseline fluorescence may be measured as a marker for intracellular $Ca^{2+}$ mobilization. $A_3R$ agonist concentration-response curves may be normalized to the response mediated by 100 μM ATP to account for differences in cell number and loading efficiency.

Inhibition of cAMP Accumulation Assays. Media may be replaced with a stimulation buffer (140 mM NaCl, 5 mM KCl, 0.8 M $MgSO_4$, 0.2 mM $Na_2HPO_4$, 0.44 mM $KH_2PO_4$, 1.3 mM $CaCl_2$, 5.6 mM D-glucose, 5 mM HEPES, 0.1% BSA, 1 U/ml ADA, and 10 μM rolipram, pH 7.45) and incubated at 37° C. for 1 hour. Inhibition of cAMP accumulation may be assessed by preincubation of $A_3$-FlpIn-CHO cells with $A_3R$ agonists for 10 minutes, after which 3 μM forskolin is added for a further 30 minutes. The reaction may be terminated by rapid removal of buffer and addition of 50 μl ice-cold 100% ethanol. Ethanol is allowed to evaporate before the addition of 50 μl detection buffer (0.1% BSA, 0.3% Tween-20, 5 mM HEPES, pH 7.45). Plates are agitated for 10 minutes, after which 10 μl lysate is transferred to a 384-well Optiplate. Detection may employ addition of a 5 μl 1:49 v/v dilution of AlphaScreen acceptor beads: stimulation buffer. Following this, a 15 μl 1:146:3 v/v/v dilution of AlphaScreen donor beads: detection buffer: 3.3 U/μl biotinylated cAMP to form a total volume of 30 μl. The donor bead/biotinylated cAMP mixture may be equilibrated for 30 minutes prior to addition. Plates may be incubated overnight in the dark at room temperature, followed by measurement of fluorescence by an EnVision plate reader (PerkinElmer) with excitation and emission set to 630 nm and 520-620 nm, respectively. Agonist concentration-response curves may be normalized to the response mediated by 3 μM forskolin (0%) or buffer (100%) alone.

Molecular Modeling. Docking simulations can be performed for all the compounds investigated in this study using homology models of the human $A_3R$. In particular, three previously reported models can be used: a model entirely based on an agonist-bound $hA_{2A}AR$ crystal structure (PDB ID: 3QAK), a model based on a hybrid $A_{2A}AR$-β2 adrenergic receptor template, and a model based on a hybrid $A_{2A}AR$-opsin template (β2 adrenoceptor X-ray structure PDB ID: 3 SN6; opsin crystal X-ray crystal structure PDB ID: 3DQB) (Tosh et al., 2012a). Models based on hybrid templates will show an outward movement of TM2 compared with the $A_{2A}AR$-based model. Structures of $A_3R$ ligands may be built and prepared for docking using the Builder and the LigPrep tools implemented in the Schrödinger suite (Schrödinger Release 2013-3, Schrödinger, LLC, New York, NY, 2013). Molecular docking of the ligands at the $A_3R$ models may be performed by means of the Glide package part of the Schrödinger suite. In particular, a Glide Grid may be centered on the centroid of some key residues of the binding pocket of adenosine receptors, namely, Phe (EL2), Asn (6.55), Trp (6.48), and His (7.43). The Glide Grid may be built using an inner box (ligand diameter midpoint box) of 14 Å×14 Å×14 Å and an outer box (box within which all the ligand atoms must be contained) that extends 25 Å in each direction from the inner one. Docking of ligands may be performed in the rigid binding site using the XP (extra precision) procedure. The top scoring docking conformations for each ligand may be subjected to visual inspection and analysis of protein-ligand interactions to select the proposed binding conformations in agreement with the experimental data.

Data Analysis. Statistical analyses and curve fitting may be performed using Prism 6 (GraphPad Software, San Diego, CA). To quantify signaling bias, agonist concentration-response curves may be analyzed by nonlinear regression using a derivation of the Black-Leff operational model of agonism, as described previously (Kenakin et al., 2012; Wootten et al., 2013; van der Westhuizen et al., 2014). The transduction coefficient, τ/KA [expressed as a logarithm, Log (τ/KA)], may be used to quantify biased agonism. To account for cell-dependent effects on agonist response, the transduction ratio may be normalized to the values obtained for the reference agonist, IB-MECA, to generate A Log(τ/KA). To determine the bias for each agonist at different signaling pathways, the A Log(τ/KA) will be normalized to a reference pathway, pERK1/2, to generate AA Log(τ/KA). Bias may be defined as $10^{AA\ Log(\tau/KA)}$ where a lack of bias will result in values that are not statistically different from 1, or 0 when expressed as a logarithm. All results may be expressed as the mean 6 S.E.M. Statistical analyses would involve an F test or a one-way analysis of variance with a Tukey or Dunnett's post hoc test, with statistical significance determined as P, 0.05.

Example 8: Pharmacokinetics and Binding of MRS4322 Following Intravenous Administration to Neonatal Pigs Purpose This study is designed to determine the plasma, brain and CSF concentrations of test compounds following intravenous administration to neonatal pigs.

Methods

Chemicals. Test compounds are prepared as described above.

Animals. Four-week old female neonatal pigs weighing approximately 7.5 Kg may be used for this study. Animals are equipped with brain microdialysis probes to obtain brain extracellular fluid samples for drug concentration determinations during the study.

Drug Administration: Test compound is solubilized in DMSO and then diluted in saline to prepare dosing solution. A 10 mL volume of dosing solution is administered by intravenous bolus administration to each neonatal pig (n=3).

Tissue Sampling: Blood samples are obtained at 0.25, 0.5, 1, 2, 4 and 6 hours post-dose. Brain extracellular fluid samples are obtained from implanted microdialysis probes at 1, 4 and 6 hours post-dose. Whole blood (1 mL) is obtained at each timepoint and placed in vacutainer tubes containing heparin and immediately centrifuged for preparation of plasma; plasma is stored at −80° C. Brain extracellular and cerebrospinal fluid samples are stored at −80° C. At the time of euthanasia (6 hours post-dose), cerebrospinal fluid samples are obtained and frozen, while brain samples from the cortex and hippocampus are obtained by decapitation, rinsed in ice-cold phosphate-buffered saline and weighed. Brain samples are then immediately flash-frozen in liquid nitrogen and stored at −80° C.

Bioanalysis

Plasma, brain, brain extracellular fluid and cerebrospinal fluid concentrations of test compound are determined by LC-MS/MS utilizing tolbutamide as an internal standard. For each tissue matrix, standard curves are created and LLOQ/ULOQ concentrations determined.

For bioanalysis of brain concentrations of test compounds, brain samples are homogenized in ice-cold phosphate-buffered saline in a 4× dilution. Aliquots of the resulting diluted brain homogenate are treated with acetonitrile and analyzed by LC-MS/MS.

Example 9: Plasma and Brain Binding of Test Compounds in Neonatal Pigs

Purpose

This study is designed to determine the plasma and brain free fraction of test compounds in neonatal pigs.

Methods

Chemicals. Test compounds may be prepared as described above. Analytical-grade sulfamethoxazole and warfarin may be obtained from commercial supplies such as Seventh Wave Laboratories (Maryland Heights, MO). All other chemicals may be obtained from a commercial vendor such as Sigma-Aldrich (St. Louis, MO).

Animals and Tissue Preparation. Plasma and brain samples from female neonatal pigs are obtained and stored at −80° C. until use.

Plasma ultrafiltrate blank samples are prepared by thawing frozen plasma and then pre-warming plasma in a humidified 5% $CO_2$ chamber at 37° C. for 60 minutes. Aliquots of 800 ul are transferred to Centrifree Centrifugal Filters (Ultracel regenerated cellulose (NMWL 30,000 amu) Lot R5JA31736) and centrifuged at 2900 RPM at 37° C. for 10 minutes; plasma water filtrates are collected and used in preparation of standards, blanks and QC standards.

Brains are weighed and homogenized with 1:9 phosphate-buffered saline, pH 7.4 using an Omni tissue homogenizer. Brains from four mice are homogenized, pooled and mixed to form one sample.

Plasma Binding Determination. Test compounds, sulfamethaxazole and warfarin are solubilized in DMSO and then diluted in 1:1 acetonitrile:water to prepare 100 uM dialysis stock solutions. Sulfamethaxazole and warfarin are utilized as study standards with known plasma binding values. Plasma samples are pre-warmed for 60 minutes in a humidified, 5% $CO_2$ incubator maintained at 37° C. Three ml aliquots of pre-warmed plasma are each spiked with test compound, sulfamethazole or warfarin using 100 uM stock solutions for each compound resulting in final test concentrations of 1 uM. Spiked plasma samples are incubated on a rotary mixer in a humidified 5% $CO_2$ chamber at 37° C. for a minimum of 60 minutes. After 60 minutes, three 800 ul aliquots of each sample are added to Centrifree centrifugal filters. The filters are subjected to centrifugation at 2900 rpm for 10 minutes at 37° C. Three 100 ul aliquots of residual plasma are collected along with ultrafiltrate for bioanalysis.

Brain Binding Determination: Test compounds, sulfamethoxazole and warfarin are solubilized in DMSO and diluted in 1:1 acetonitrile:water to prepare 100 uM dialysis stock solutions. Pooled homogenized brains are pre-warmed for 60 minutes in a humidified, 5% $CO_2$ incubator maintained at 37° C. Three ml aliquots of brain homogenate are each spiked with test compound, sulfamethaxazole or warfarin using the 100 uM stock solutions for each compound resulting in final spiked concentrations of 1 uM. Spiked pooled brain homogenates are placed on a Nutator mixer in a humidified, 5% $CO_2$ incubator at 37° C. for 60 minutes. After 60 minutes, three 800 ul aliquots of each sample are added to Centrifree centrifugal filters. The filters are subjected to centrifugation at 2900 rpm for 10 minutes at 37 C. Aliquots of residual brain homogenate and ultrafiltrate are collected for bioanalysis.

Bioanalysis

Plasma and brain concentrations of test compounds in spiked plasma, brain homogenates and associated ultrafiltrates are determined by LC-MS/MS utilizing tolbutamide as an internal standard. Associated concentrations of sulfamethaxazole and warfarin are also determined by LC-MS/MS using standard conditions.

Example 10: Pharmacological Characterization of Test Compounds

Test compounds are investigated in competition binding studies at human and mouse $A_3$ adenosine receptors recombinantly expressed in Chinese hamster ovary (CHO) cells using cell membrane preparations. $[^3H]$NECA is employed as an $A_3$ agonist radioligand. The non-selective agonist NECA could be used because CHO cells do not natively express adenosine receptors. Concentration-dependent displacement of the radioligand by test compounds are determined.

Additionally cAMP experiments are conducted at CHO cells recombinantly expressing human $A_3$ or mouse $A_3$ adenosine receptors, respectively. The non-selective agonist NECA is used as a control.

See Alnouri M. W. et al., "Selectivity is species-dependent: Characterization of standard agonists and antagonists at human, rat, and mouse adenosine receptors," Purinergic Signal. 2015, 11, 389-407. The same cell lines are used in the present and in the published study.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method of preparing a compound of Formula I:

I

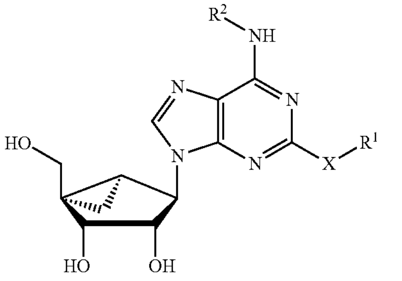

or a pharmaceutically acceptable salt thereof, wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; or X is a covalent bond when $R^1$ is a halogen; and n is 0, 1, 2, or 3;

comprising the steps of:

(a) providing a compound of Formula C:

C

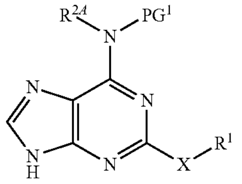

wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^{2A}$ is a suitable amino protecting group or $R^2$; or $R^{2A}$ and $PG^1$ are taken together to form a suitable bivalent nitrogen protecting group;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; or X is a covalent bond when $R^1$ is a halogen;

n is 0, 1, 2, or 3; and $PG^1$ is a suitable amino protecting group or is taken together with $R^{2A}$ to form a suitable bivalent nitrogen protecting group;

(b) coupling said compound of Formula C with a compound of Formula B:

B

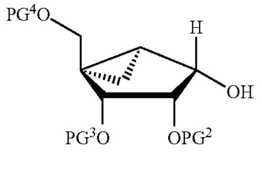

wherein each of $PG^2$, $PG^3$, and $PG^4$ is independently a suitable hydroxyl protecting group; or $PG^2$ and $PG^3$ are taken together with the oxygen atoms to which they are bound to form a cyclic ketal or acetonide;

to form a compound of Formula A:

A

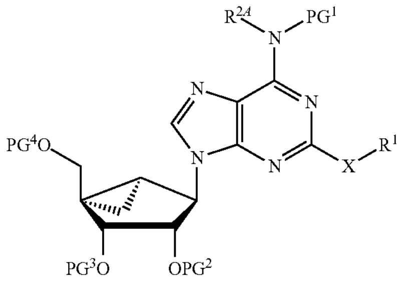

wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$; or $R^1$ is a halogen when X is a covalent bond;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^{2A}$ is a suitable amino protecting group or $R^2$; or $R^{2A}$ and $PG^1$ are taken together to form a suitable bivalent nitrogen protecting group;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; or X is a covalent bond when $R^1$ is a halogen;

n is 0, 1, 2, or 3;

$PG^1$ is a suitable amino protecting group or is taken together with $R^{2A}$ to form a suitable bivalent nitrogen protecting group; and each of $PG^2$, $PG^3$, and $PG^4$ is independently a suitable hydroxyl protecting group; or $PG^2$ and $PG^3$ are taken together with the oxygen atoms to which they are bound to form a cyclic ketal or acetonide;

and (c) deprotecting said compound of Formula A to form said compound of Formula I.

2. The method of claim 1, wherein $PG^2$ and $PG^3$ are taken together with the oxygen atoms to which they are bound to form a cyclic ketal or acetonide.

3. The method of claim 1, wherein $R^1$ is $C_{1-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$.

4. The method of claim 1, wherein $PG^4$ taken with the oxygen atom to which it is bound is a silyl ether or arylalkyl ether or wherein $PG^4$ is trityl.

5. The method of claim 1, wherein X is S.

6. The method of claim 1, wherein the deprotection at step (c) is achieved by treating said compound of Formula A with a suitable acid.

7. The method of claim 6, wherein the method further comprises the step of (d) treating a salt of the compound of Formula I with a suitable base to form the free-base compound of Formula I.

8. The method of claim 1, wherein the coupling at step (b) is achieved in the presence of a suitable phosphine and a suitable azodicarboxylate reagent.

9. A method of preparing a compound of Formula C:

C

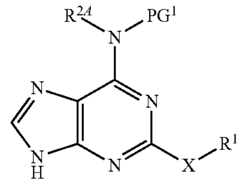

wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^{2A}$ is a suitable amino protecting group or $R^2$; or $R^{2A}$ and $PG^1$ are taken together to form a suitable bivalent nitrogen protecting group;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl-, or —SH;

X is S or O;

n is 0, 1, 2, or 3; and $PG^1$ is a suitable amino protecting group or is taken together with $R^{2A}$ to form a suitable bivalent nitrogen protecting group, comprising the steps of:

(a) providing a compound of Formula E:

E

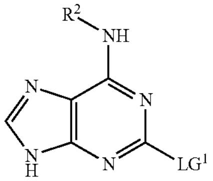

wherein:

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms; and $LG^1$ is a suitable leaving group;

(b) coupling said compound of Formula E to form a compound of Formula D:

D

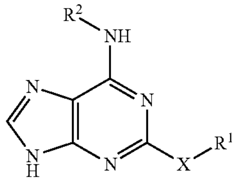

wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O; and n is 0, 1, 2, or 3;

and (c) protecting said compound of Formula D to form said compound of Formula C.

10. The method of claim 9, wherein $R^1$ is $C_{1-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$.

11. The method of claim 9, wherein X is S.

12. A compound of Formula I-A:

I-A

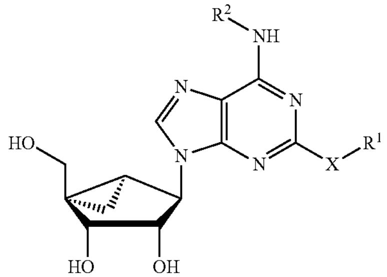

or a pharmaceutically acceptable salt thereof, wherein:

$R^1$ is (i) $C_{1-2}$ alkyl substituted with 1, 2, or 3 instances of $R^3$, or (ii) $C_{3-8}$ alkyl, —($C_{1-4}$ alkylene)-phenyl, —($C_{1-4}$ alkylene)-($C_{3-8}$ cycloalkyl), $C_{2-8}$ alkenyl, $C_{2-8}$ alkynyl, $C_{3-8}$ cycloalkyl, phenyl, or a 5-6 membered monocyclic heteroaromatic ring having 1-4 heteroatoms independently selected from nitrogen, oxygen, and sulfur; each of which is substituted with n instances of $R^3$;

$R^2$ is hydrogen, $C_{1-4}$ alkyl, or $C_{3-5}$ cycloalkyl;

each $R^3$ is independently halogen, —O—($C_{1-4}$ alkyl), —OH, —S—($C_{1-4}$ alkyl), or —SH;

X is S or O; and n is 0, 1, 2, or 3.

13. The compound of claim 12, wherein $R^1$ is (i) $C_{1-2}$ alkyl substituted with 1, 2, or 3 instances of $R^3$, or (ii) $C_{3-8}$ alkyl, —($C_{1-2}$ alkylene)-phenyl, —($C_{1-2}$ alkylene)-($C_{3-5}$ cycloalkyl), or $C_{3-8}$ cycloalkyl; each of which is substituted with n instances of $R^3$.

14. The compound of claim 12, wherein X is S.

15. A compound selected from one of the following:

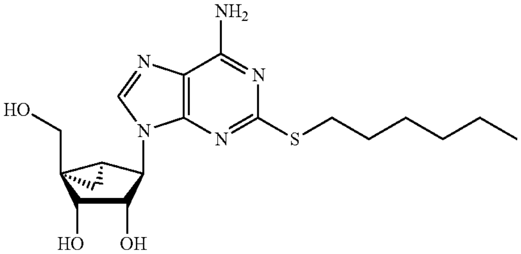

,

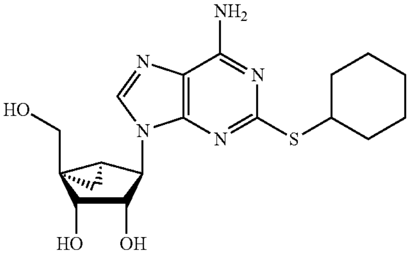

,

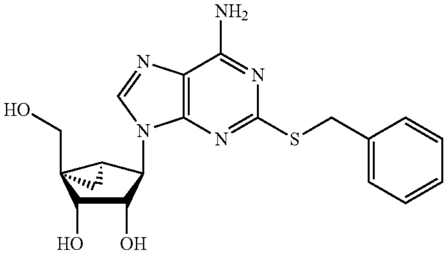

,

-continued
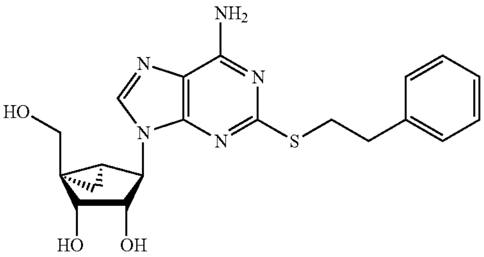
,
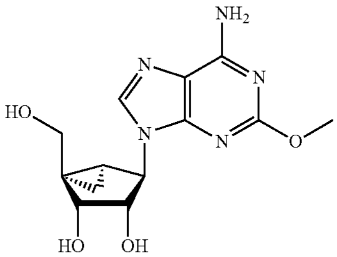
,
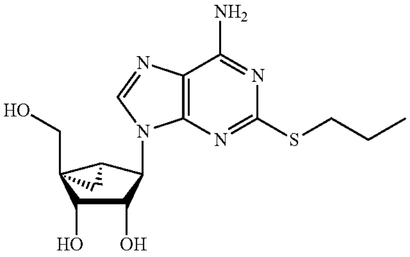
,
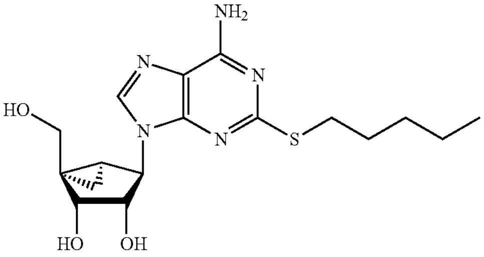
,
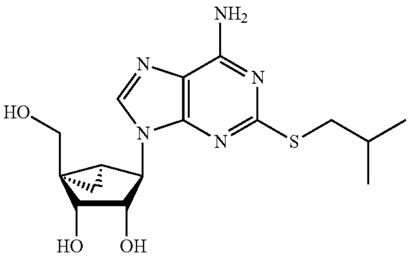
,
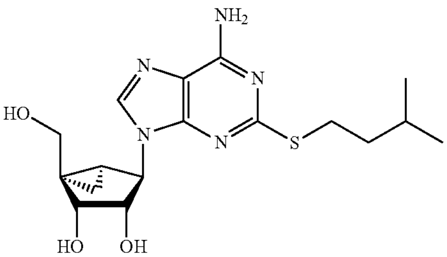
,
-continued
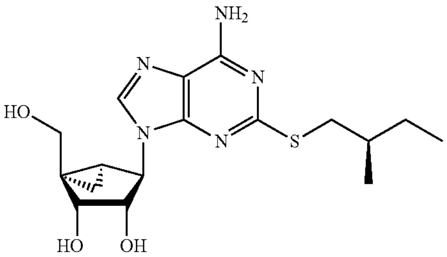
,
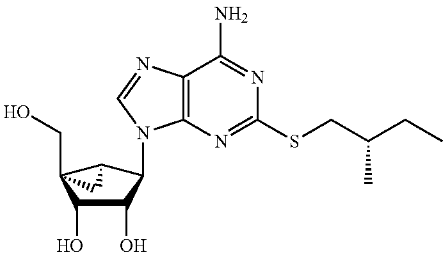
,
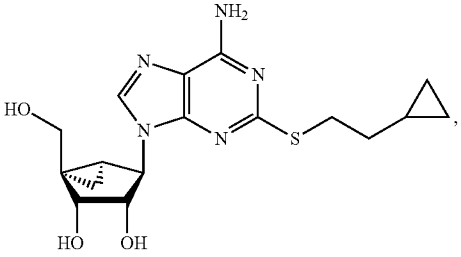
,
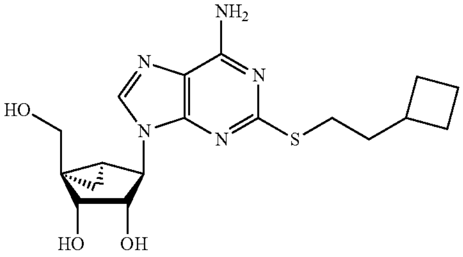
,
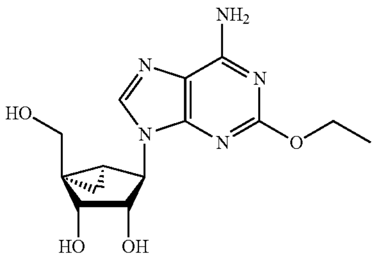
,
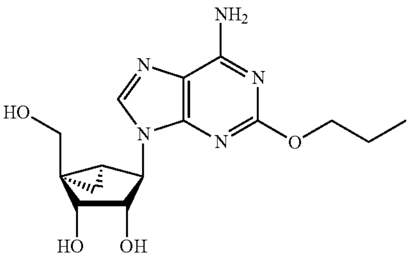
, -continued

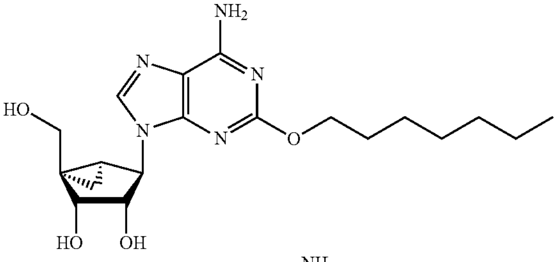
,

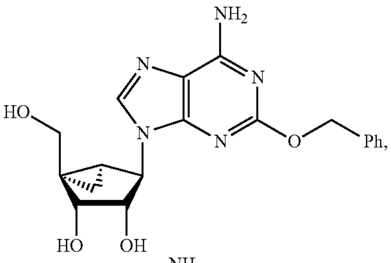
,

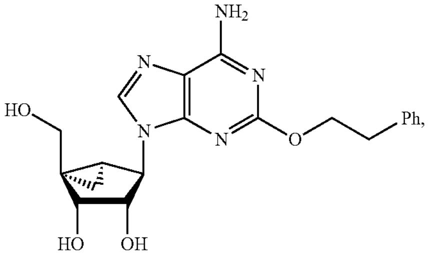
and

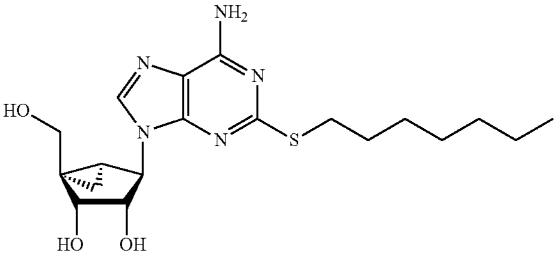
, or a pharmaceutically acceptable salt thereof.

16. A compound of Formula A:

A

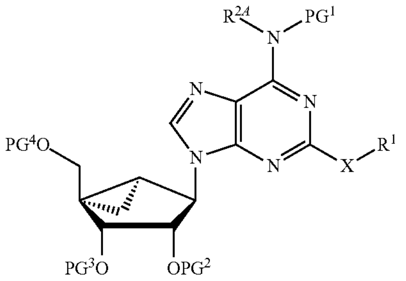

wherein:

$R^1$ is $C_{1-8}$ alkyl, —($C_{1-4}$ alkylene)-Ar, —($C_{1-4}$ alkylene)-Cy, $C_{2-8}$ alkenyl, —($C_{2-4}$ alkenylene)-Ar, —($C_{2-4}$ alkenylene)-Cy, $C_{2-8}$ alkynyl, —($C_{2-4}$ alkynylene)-Ar, —($C_{2-4}$ alkynylene)-Cy, phenyl, Cy, or a 5-6 membered monocyclic heteroaromatic ring having 1, 2, 3, or 4 heteroatoms independently selected from nitrogen, oxygen, and sulfur; each of which is substituted with n instances of $R^3$;

Ar is phenyl or a 5-6 membered monocyclic heteroaromatic ring having 1, 2, 3, or 4 heteroatoms independently selected from nitrogen, oxygen, and sulfur;

Cy is a 3-8 membered saturated or partially unsaturated monocyclic carbocyclic ring, a 7-12 membered saturated or partially unsaturated bicyclic carbocyclic ring, or a 3-6-membered saturated or partially unsaturated monocyclic heterocyclic ring having 1 or 2 heteroatoms independently selected from nitrogen, oxygen, and sulfur;

$R^{2A}$ is a suitable amino protecting group or $R^2$; or $R^{2A}$ and $PG^1$ are taken together to form a suitable bivalent nitrogen protecting group;

$R^2$ is hydrogen, $C_{1-4}$ alkyl, or $C_{3-5}$ cycloalkyl; wherein said $C_{1-4}$ alkyl and $C_{3-5}$ cycloalkyl are optionally substituted with 1, 2, or 3 deuterium or halogen atoms;

each $R^3$ is independently deuterium, halogen, —CN, —O—($C_{1-4}$ alkyl), —OH, —S—($C_{1-4}$ alkyl), or —SH;

X is S or O;

n is 0, 1, 2, or 3;

$PG^1$ is a suitable amino protecting group or is taken together with $R^{2A}$ to form a suitable bivalent nitrogen protecting group; and each of $PG^2$, $PG^3$, and $PG^4$ is independently a suitable hydroxyl protecting group; or $PG^2$ and $PG^3$ are taken together with the oxygen atoms to which they are bound to form a cyclic ketal or acetonide.

17. A pharmaceutical composition comprising a compound of claim 12 and a pharmaceutically acceptable carrier, adjuvant, or vehicle.

18. A method of treating an injury, disease, or condition selected from traumatic brain injury (TBI) and stroke;

comprising administering to a patient in need thereof an effective amount of a compound of claim 12 or a pharmaceutically acceptable salt thereof.

19. A compound of Formula I-B:

I-B

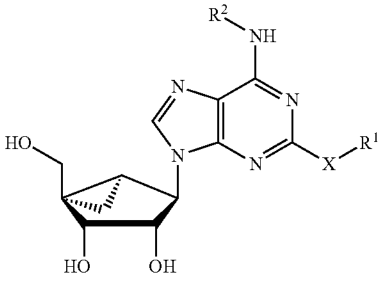

or a pharmaceutically acceptable salt thereof, wherein:

$R^1$ is a halogen;

$R^2$ is $C_{2-4}$ alkyl, or $C_{3-4}$ cycloalkyl; and

X is a covalent bond.

* * * * *